(12) United States Patent
Beuerman et al.

(10) Patent No.: US 8,691,945 B2
(45) Date of Patent: Apr. 8, 2014

(54) ANTIMICROBIAL PEPTIDES

(75) Inventors: Roger Beuerman, Singapore (SG); Lei Zhou, Singapore (SG); Shouping Liu, Singapore (SG); Jing Li, Singapore (SG); Anita Suresh, Evanston, IL (US); Chandra Shekhar Verma, Singapore (SG); Donald Tan, Singapore (SG)

(73) Assignees: Singapore Health Services Pte Ltd., Singapore (SG); Agency for Science, Technology and Research, Singapore (SG)

( * ) Notice: Subject to any disclaimer, the term of this patent is extended or adjusted under 35 U.S.C. 154(b) by 796 days.

(21) Appl. No.: 12/298,702

(22) PCT Filed: Apr. 27, 2007

(86) PCT No.: PCT/SG2007/000121
§ 371 (c)(1),
(2), (4) Date: Oct. 27, 2008

(87) PCT Pub. No.: WO2007/126392
PCT Pub. Date: Nov. 8, 2007

(65) Prior Publication Data
US 2010/0048469 A1    Feb. 25, 2010

Related U.S. Application Data

(60) Provisional application No. 60/795,522, filed on Apr. 27, 2006.

(51) Int. Cl.
| C07K 14/00 | (2006.01) |
| C07K 14/46 | (2006.01) |
| C07K 14/47 | (2006.01) |
| A61K 38/00 | (2006.01) |
| A61K 39/00 | (2006.01) |
| A61K 38/04 | (2006.01) |
| A61K 38/17 | (2006.01) |

(52) U.S. Cl.
CPC .................. *A61K 38/1729* (2013.01)
USPC ........ 530/326; 530/328; 530/300; 424/184.1; 424/185.1

(58) Field of Classification Search
None
See application file for complete search history.

(56) References Cited

U.S. PATENT DOCUMENTS

| 6,420,116 | B1 * | 7/2002  | Olsen et al. ................... 435/6.12 |
| 6,514,727 | B1   | 2/2003  | Selsted et al. |
| 6,576,755 | B1 * | 6/2003  | Adler et al. ................... 536/23.5 |
| 6,809,181 | B2 * | 10/2004 | McCray et al. ............... 530/350 |
| 7,087,407 | B2 * | 8/2006  | Adler et al. ................... 435/69.1 |
| 7,294,613 | B2 * | 11/2007 | Adler et al. ................... 514/2.3 |
| 7,338,936 | B2 * | 3/2008  | Lim et al. ...................... 514/2.6 |
| 7,384,911 | B2 * | 6/2008  | Bulet et al. .................... 514/2.3 |
| 7,419,781 | B1 * | 9/2008  | Christophers et al. ....... 435/6.16 |
| 7,528,107 | B2 * | 5/2009  | Shi et al. ....................... 514/1.1 |
| 7,566,447 | B2 * | 7/2009  | Homan et al. ................ 424/94.1 |
| 7,658,928 | B2 * | 2/2010  | Fritz et al. .................... 424/184.1 |
| 7,674,291 | B2 * | 3/2010  | Centanni et al. ............ 623/15.12 |
| 7,785,828 | B1 * | 8/2010  | Wu et al. ....................... 435/69.1 |
| 7,985,729 | B2 * | 7/2011  | Lim et al. ........................ 514/2.4 |
| 8,092,531 | B2 * | 1/2012  | Centanni et al. ............ 623/15.12 |
| 8,563,689 | B1 * | 10/2013 | Takashi et al. ................ 530/326 |
| 2002/0110553 | A1 | 8/2002 | Fleiszig et al. |
| 2003/0148936 | A1 * | 8/2003 | Svendsen et al. ................ 514/12 |
| 2003/0176652 | A1 | 9/2003 | McCray et al. |
| 2003/0223987 | A1 * | 12/2003 | Paoletti et al. ............. 424/130.1 |
| 2004/0170642 | A1 * | 9/2004 | Fritz et al. ................. 424/185.1 |
| 2004/0224883 | A1 | 11/2004 | Weinberg |
| 2005/0245437 | A1 * | 11/2005 | Bulet et al. ........................ 514/9 |
| 2006/0034820 | A1 * | 2/2006 | Lim et al. .................... 424/94.61 |
| 2008/0051333 | A1 * | 2/2008 | Shi et al. .......................... 514/12 |
| 2009/0221483 | A1 * | 9/2009 | Melgarejo et al. .............. 514/12 |
| 2010/0016546 | A1 * | 1/2010 | Bishop ............................ 530/322 |
| 2010/0022750 | A1 * | 1/2010 | Bishop et al. .................. 530/345 |
| 2010/0048480 | A1 * | 2/2010 | Bommarius et al. ........... 514/12 |
| 2010/0221272 | A1 * | 9/2010 | Napper et al. ............. 424/185.1 |
| 2010/0316643 | A1 * | 12/2010 | Eckert et al. ............... 424/134.1 |
| 2011/0039760 | A1 * | 2/2011 | Beuerman et al. ............. 514/2.3 |
| 2011/0039761 | A1 * | 2/2011 | Eckert et al. ................... 514/2.4 |
| 2011/0039762 | A1 * | 2/2011 | Eckert et al. ................... 514/2.4 |
| 2011/0039763 | A1 * | 2/2011 | Eckert et al. ................... 514/2.4 |

FOREIGN PATENT DOCUMENTS

| WO | 02/40512 A2 | 5/2002 |
| WO | 2004/050132 A2 | 6/2004 |
| WO | WO 2005/012492 A2 * | 2/2005 |
| WO | WO2005012492 B1 | 2/2005 |
| WO | WO 2008/140582 A2 * | 11/2008 |
| WO | WO 2009/131548 A1 * | 10/2009 |

OTHER PUBLICATIONS

Bai et al, Biochemistry, 2009, 48:7229-7239.*
Liu et al, ChemBioChem, 2008, 9:964-973.*
Liu et al, Int. J. Pept. Res. Ther., 2010, 16:199-213.*
Zhou et al, Amino Acids, 2011, 40:123-133.*
Bowie et al. Science, 1990, 247/4948:1306-1310.*
Kumar et al. PNAS 87: 1337-1341 Feb. 1991.*
Thomas E. Creighton, in his book, "Proteins: Structures and Molecular Properties, 1984", (pp. 314-315.*
Hoover, D. M., et al. "Antimicrobial Characterization of Human Beta-Defensin 3 Derivatives". Antimicrobial Agents and Chemotherapy, Sep. 2003, vol. 47, No. 9, p. 2809-2809.
Wu, Z., et al. "Engineered Disulfide Bridges to Dissect Antimicrobial and Chemotactic Activity of Human Beta-Defensin 3". Proceedings of the National Academy of Sciences, Jul. 2003, vol. 100, No. 15, p. 8880-8885.
Kluver, E., et al. "Structure-Activity Relation of Human Beta-Defensin 3: Influence of Disulfide Bonds and Cysteine Substitution of Antimicrobial Activity and Cytotoxicity". Biochemistry, Jun. 2005, vol. 44, No. 28, p. 9804-9816.
Raj, P.A., et al. "Large Scale Synthesis and Functional Elements for Antimicrobial Activity of Defensins". J. Biochem., 2000, 347, p. 633-641.
European Search Report issued in European Patent Application No. EP 10 17 7642, dated Jan. 13, 2011.

(Continued)

*Primary Examiner* — Nita M Minnifield
(74) *Attorney, Agent, or Firm* — Heslin Rothenberg Farley & Mesiti PC; Andrew K. Gonsalves, Esq.

(57) ABSTRACT

There is provided at least one isolated antimicrobial peptide, wherein the peptide is a linear analog of hBD3 or a fragment thereof. In particular, there is provided a linear analog of hBD3 wherein the peptide has a reduced cytotoxicity to at least one cell compared to the wild type hBD3.

16 Claims, 49 Drawing Sheets

(56) References Cited

OTHER PUBLICATIONS

Supplementary European Search Report issued for EP 07 74 8666, dated Feb. 3, 2010.
Dhople et al., "The human beta-defensin-3, an antibacterial peptide with multiple biological functions," *Biochimica et Biophysica Acta*, 1758(9):1499-1512 (2006).
Ganz, T., *Science*, 286:420-421 (1999).
Yang et al., *Journal of Leukocyte Biology*, 69:691-697 (2001).
Kaiser et al., *Journal of Leukocyte Biology*, 68:779-784 (2000).
Schroder, J.M., *Cellular and Molecular Life Sciences*, 56:32-46 (1999).
Garcia et al., *FASEB J.*, 15:1819-1821 (2001).
Harder et al., *Nature*, 387:861 (1997).
Schibli et al., *Journal of Biological Chemistry*, 277(10):8279-8289 (2002).
Harder et al., *Journal of Biological Chemistry*, 276(8):5707-5713 (2001).
Garcia et al., *Cell Tissue Research*, 306:257-264 (2001).
Yeaman et al., *Pharmacological Reviews*, 55(1):27-55 (2003).
Hwang et al., *Biochemistry and Cell Biology*, 76:235-246 (1998).
Zucht et al., *European Journal of Medical Research*, 3:315-323 (1998).
Gordon et al., *Current Eye Research*, 30(7):505-515 (2005).
Wimley et al., *Nature Structural Biology*, 3(10):842-848 (1996).
Hopp et al., *Molecular Immunology*, 20(4):483-489 (1983).
Black et al., *Analytical Biochemistry*, 193:72-82 (1991).
Ilker et al., *Journal of American Chemical Society*, 126(48):15870-15875 (2004).
Sawai et al., *Biochemistry*, 40)13:3810-3816 (2001).
Oren et al., *Biochemistry*, 36(7):1826-1835 (1997).

* cited by examiner

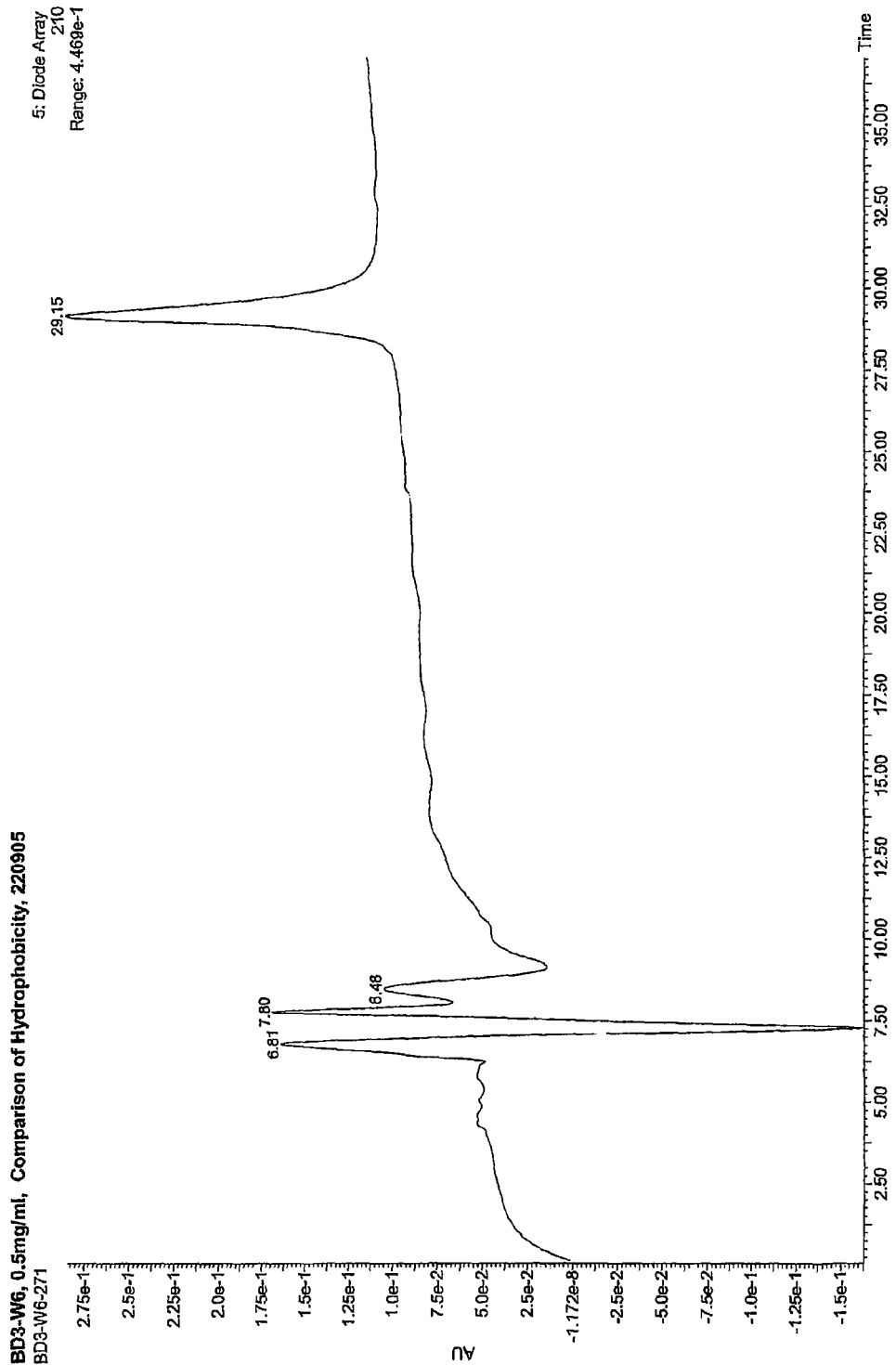
Figure 8A RP-HPLC-UV chromatogram and MS spectrum of W6

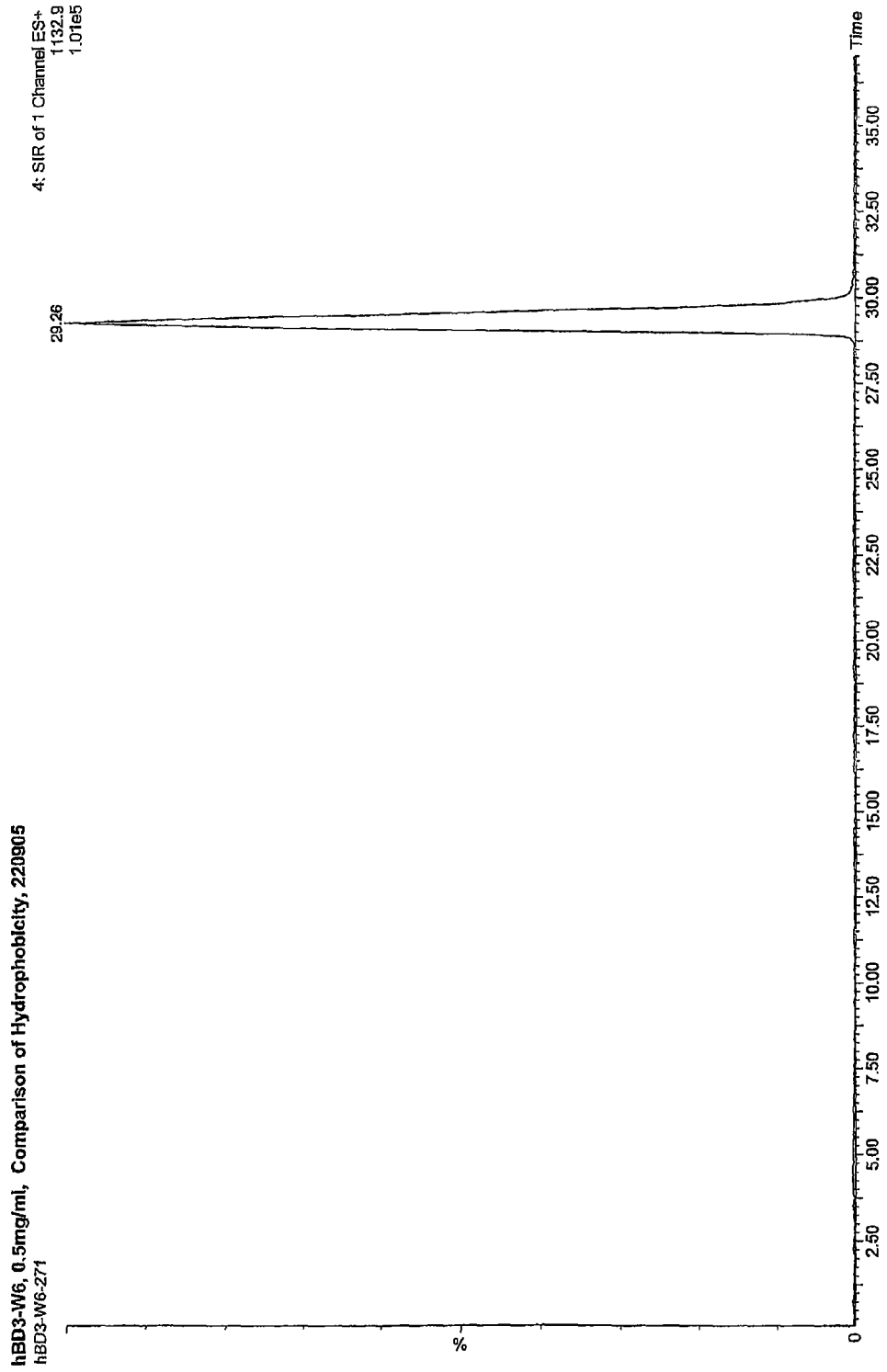
Figure 8B SIR chromatogram at m/z = 1132.9 ($[M+5H]^{5+}$)

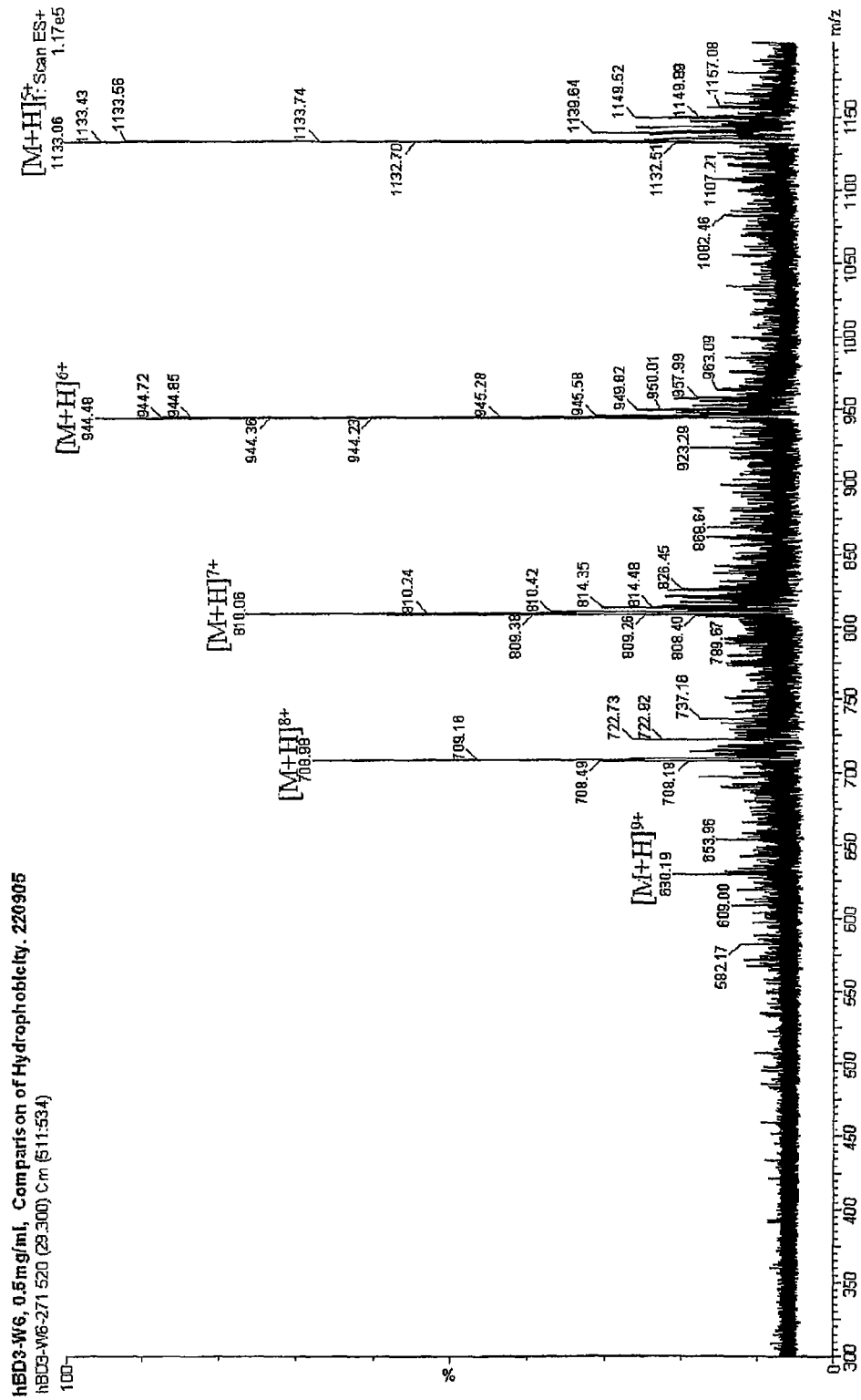
Figure 8C ES+ MS SPECTRUM

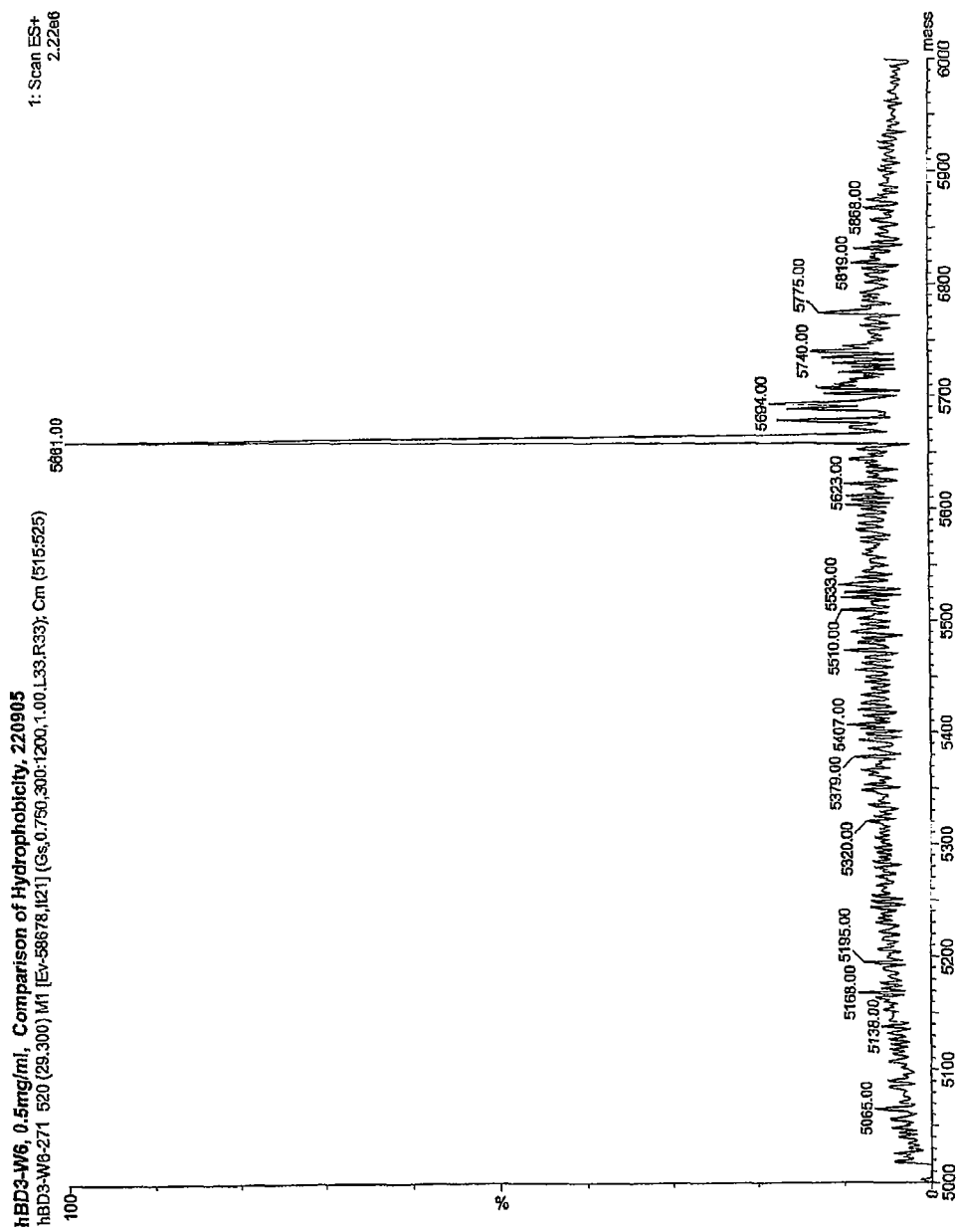
Figure 8D Deconvoluted MS spectrum

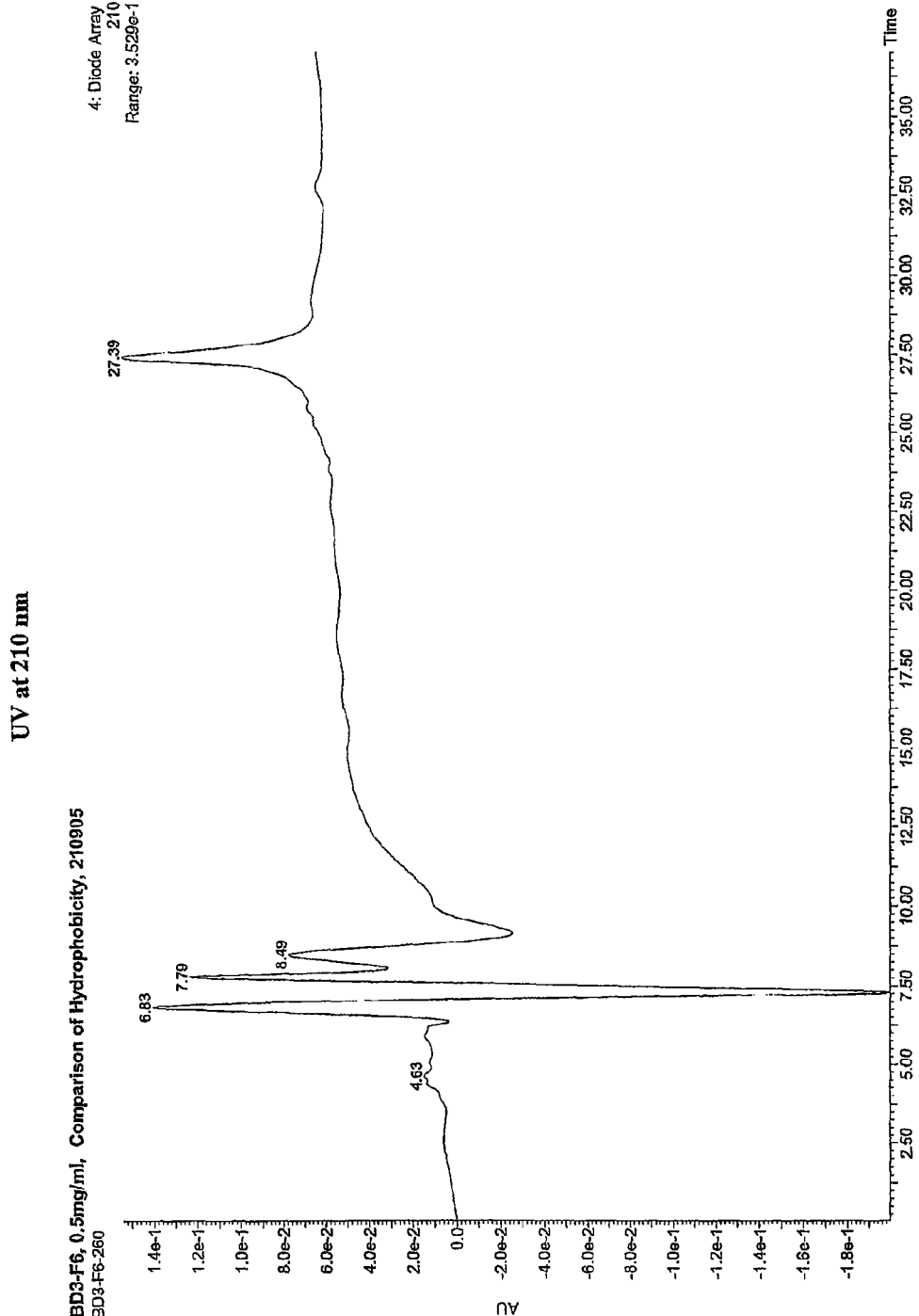
Figure 9A RP-HPLC-UV chromatogram and MS spectrum of F6

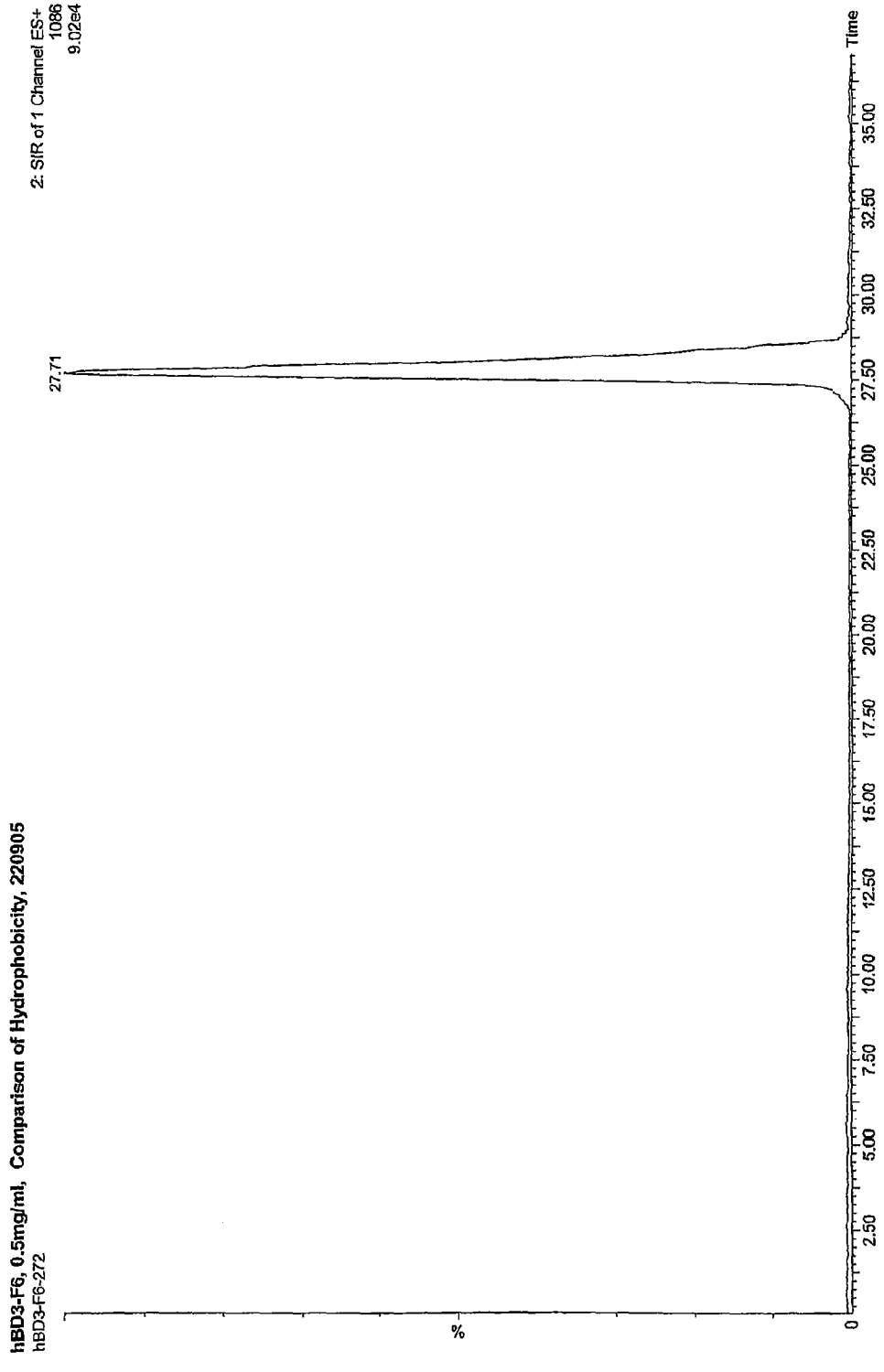
Figure 9B SIR chromatogram at m/z = 1086 ($[M+5H]^{5+}$)

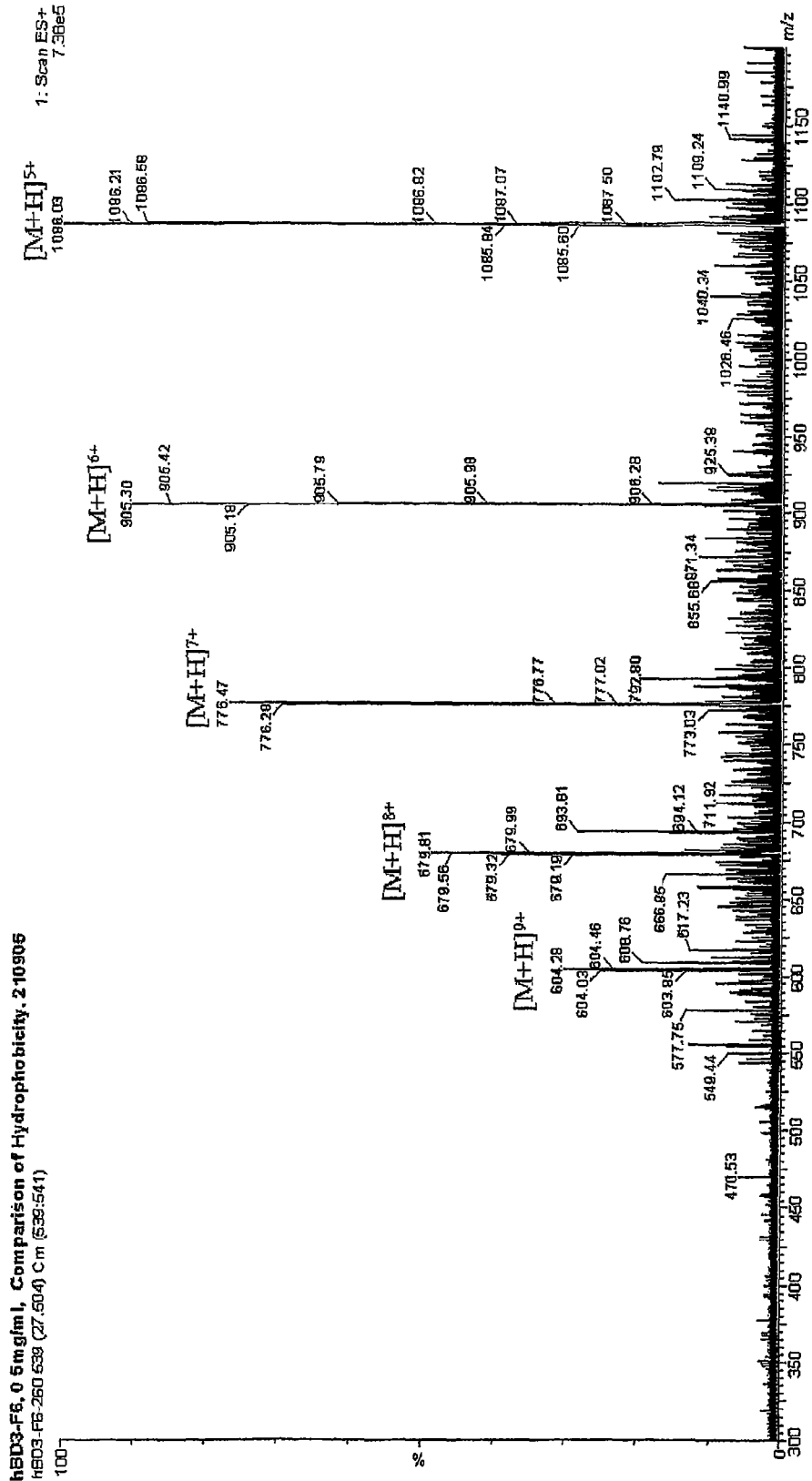
Figure 9C ES+ MS Spectrum

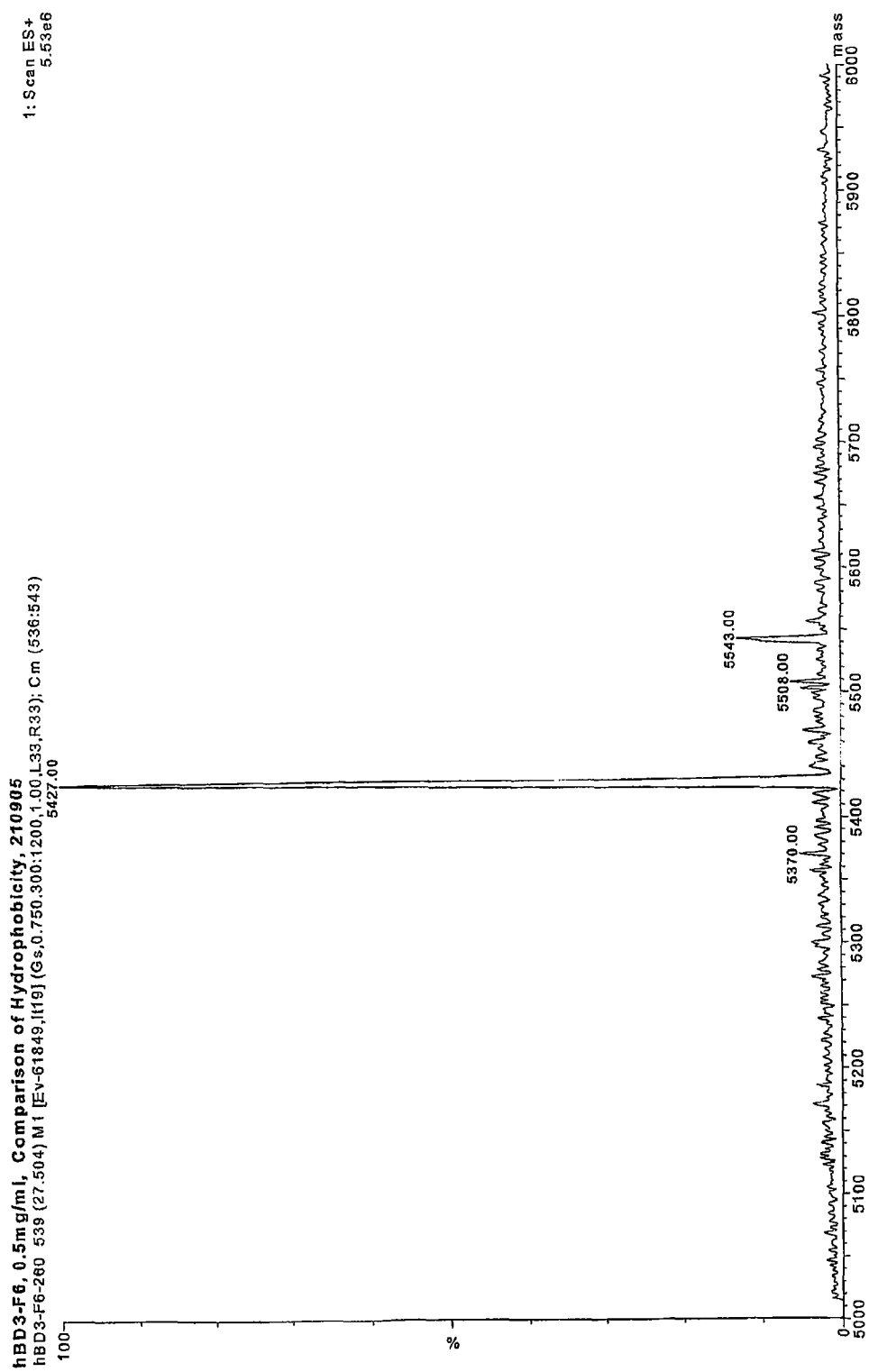
Figure 9D Deconvoluted MS spectrum

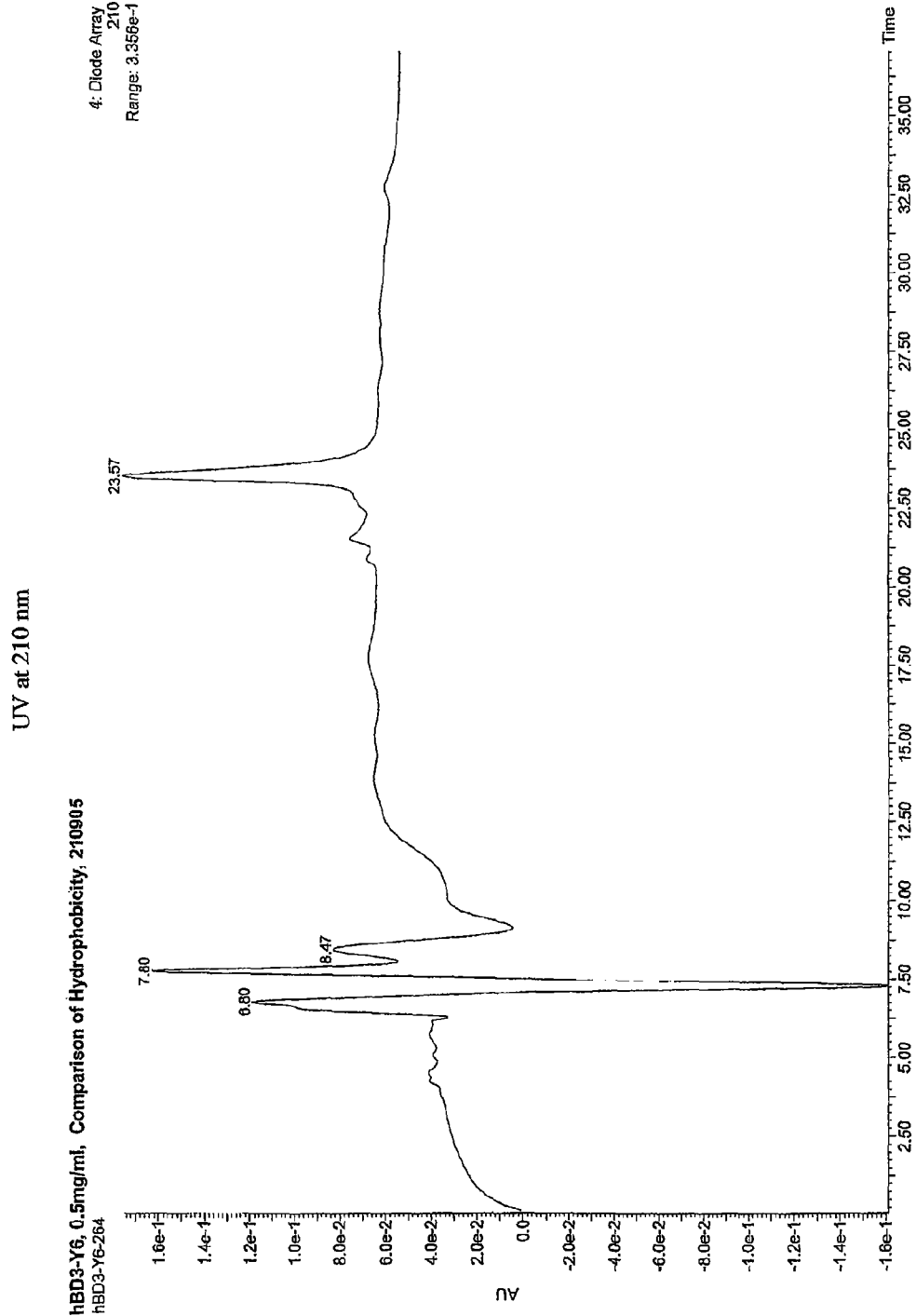
Figure 10A RP-HPLC-UV chromatogram and MS spectrum of Y6

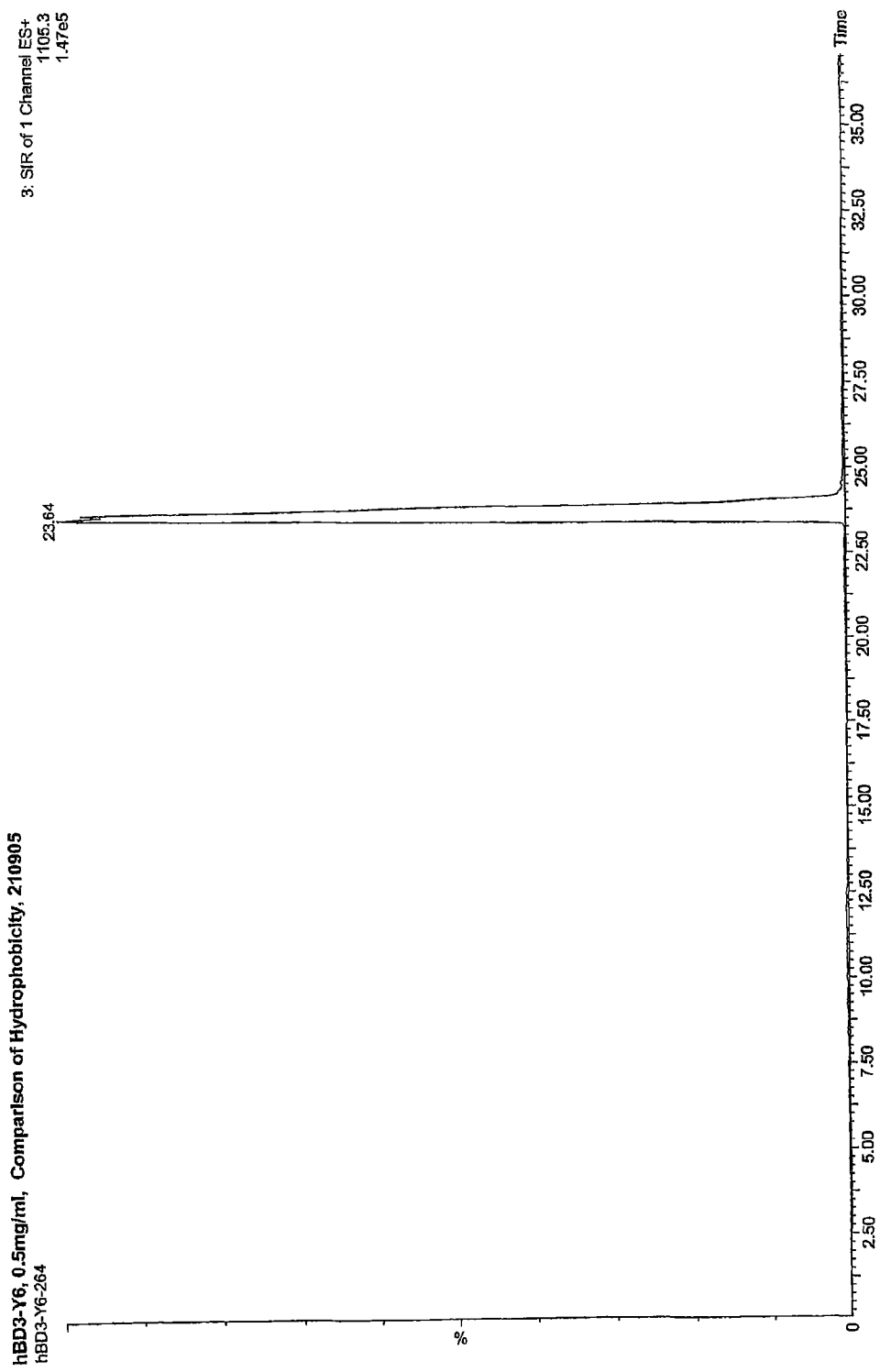
Figure 10B SIR chromatogram at m/z = 1105.3 ($[M+5H]^{5+}$)

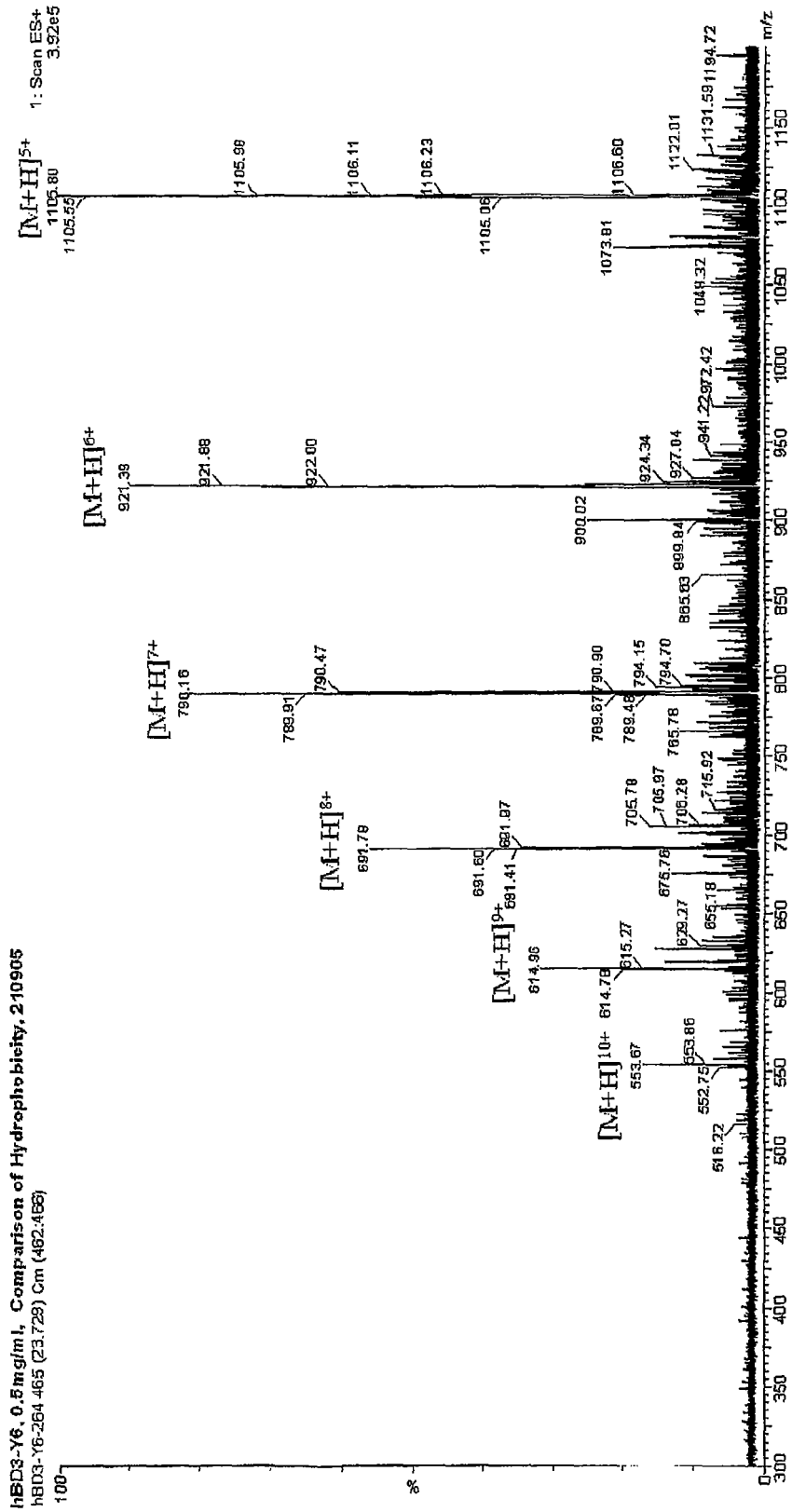
Figure 10C ES + MS Spectrum

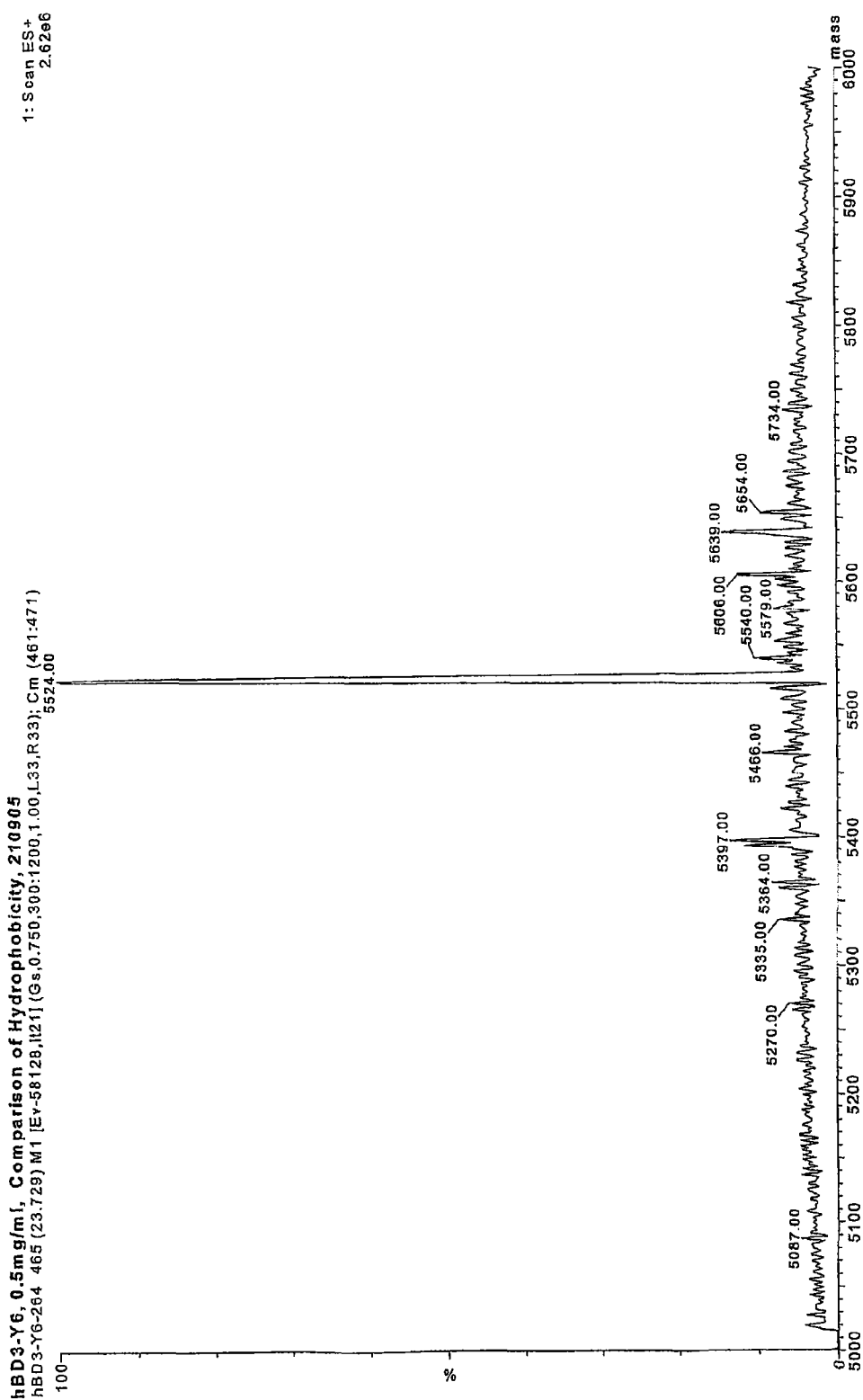
Figure 10D Deconvoluted MS

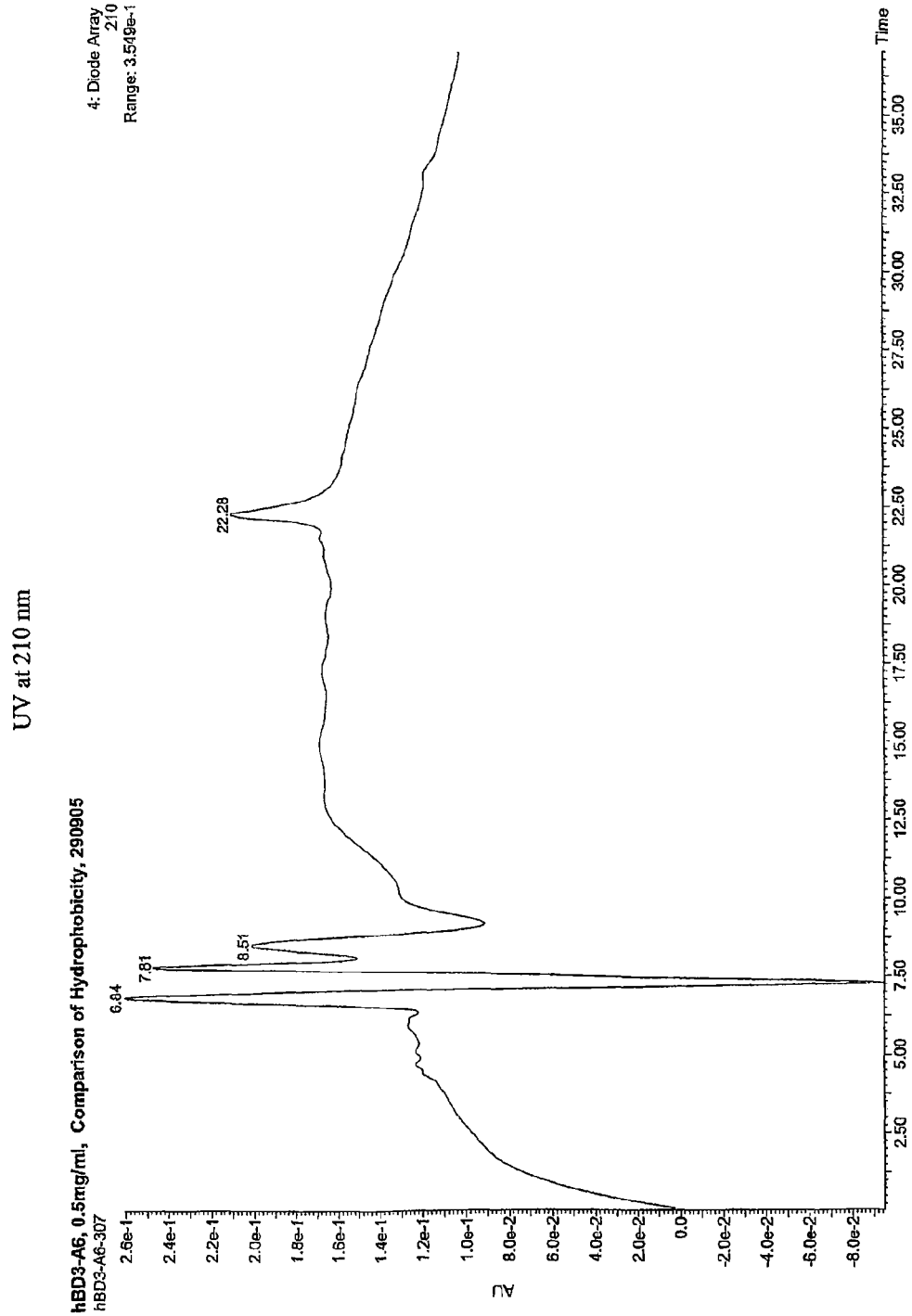
Figure 11A RP-HPLC-UV chromatogram and MS spectrum of A6

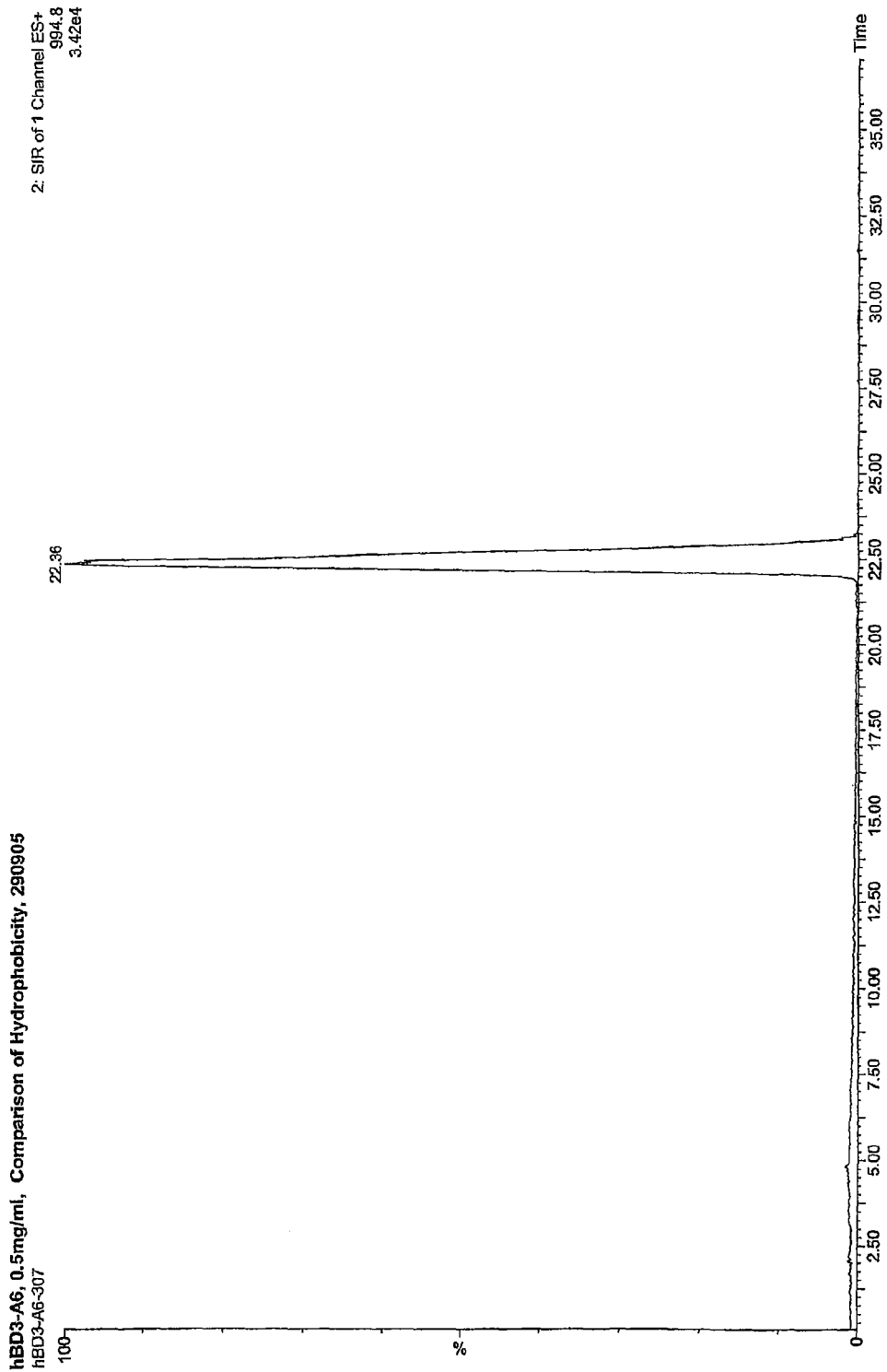
Figure 11B SIR chromatogram at m/z = 994.8 ($[M+5H]^{5+}$)

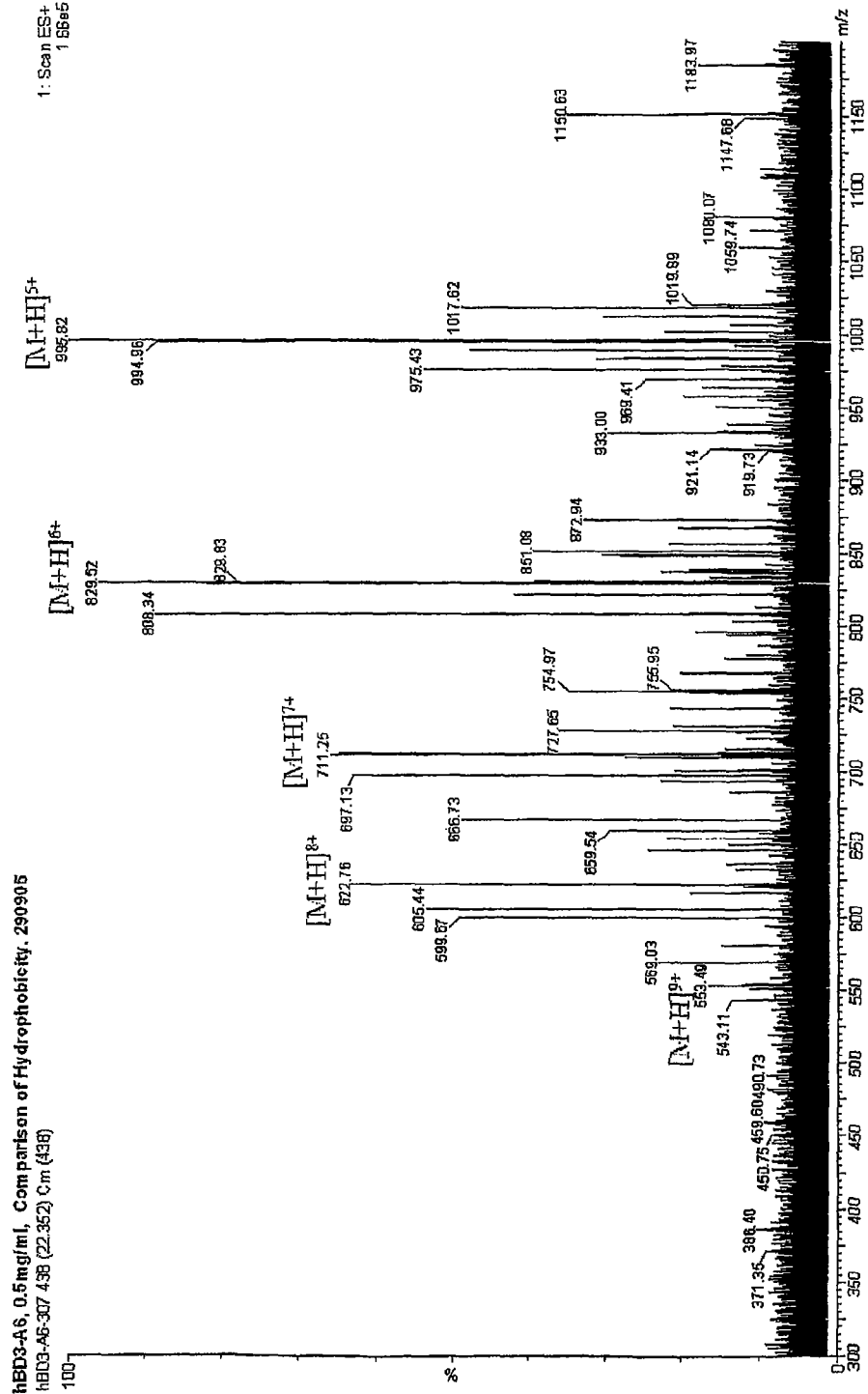
Figure 11C ES + MS specturm

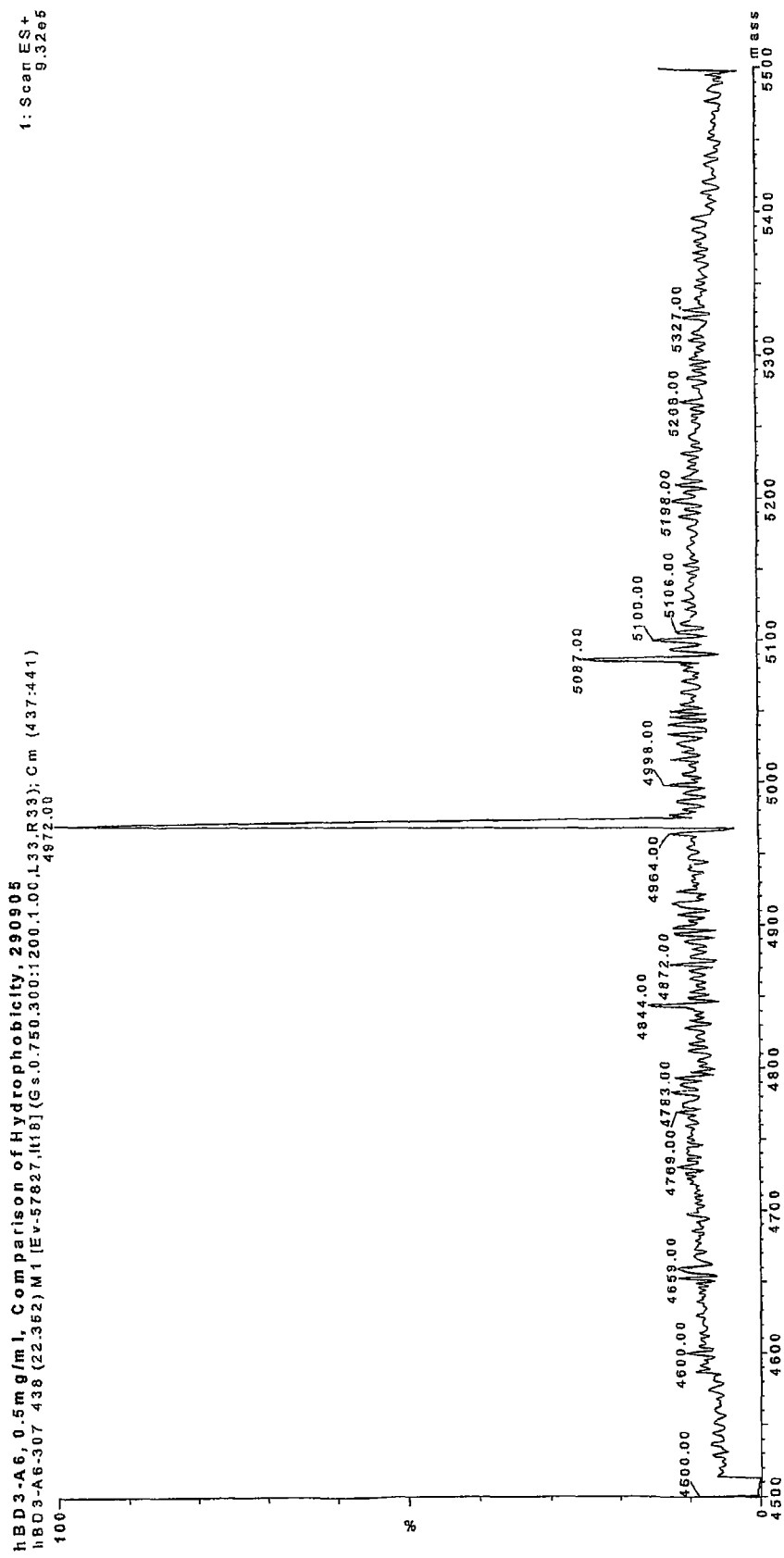
Figure 11D Deconvoluted MS spectrum

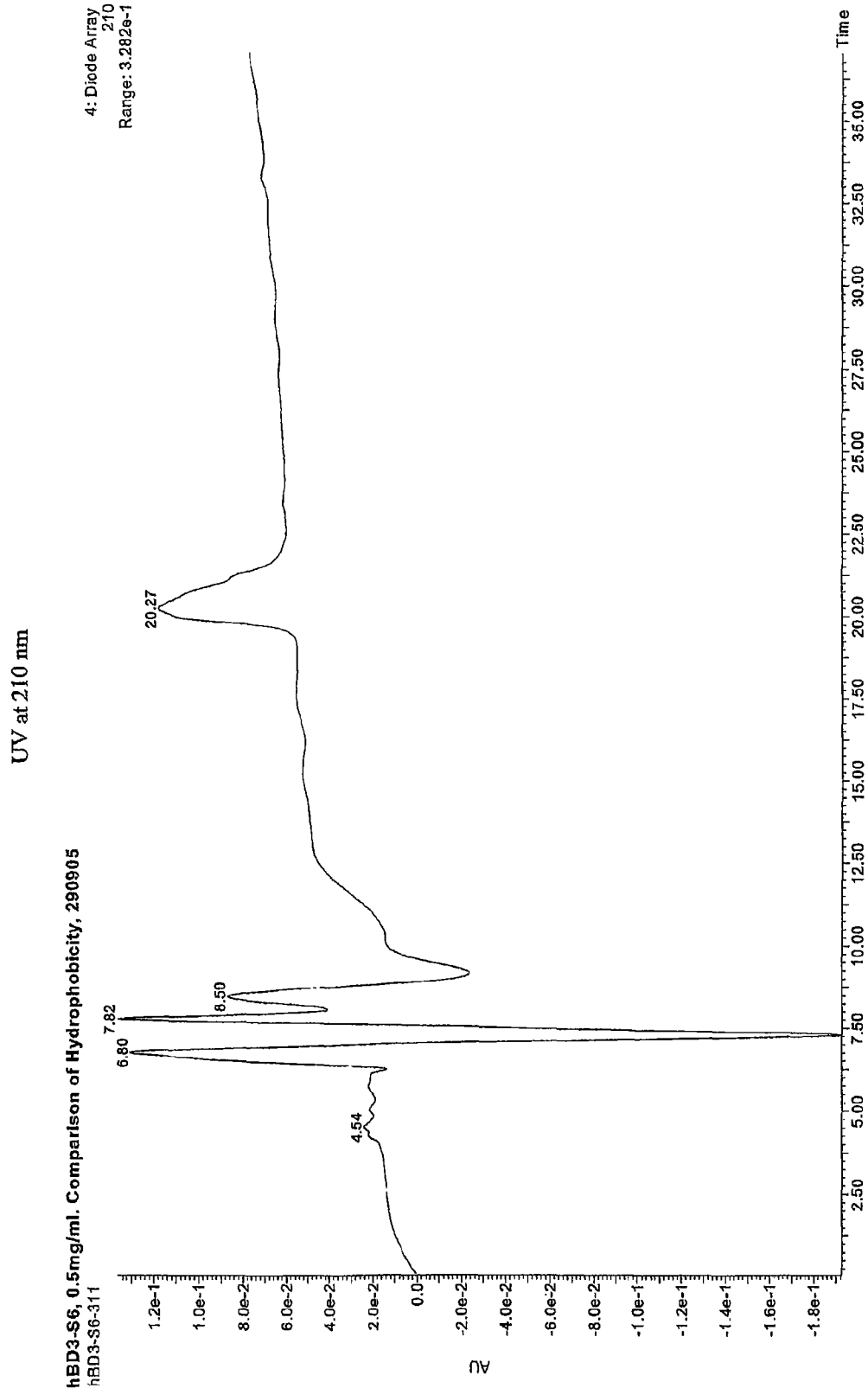
Figure 12A RP-HPLC-UV chromatogram and MS spectrum of S6

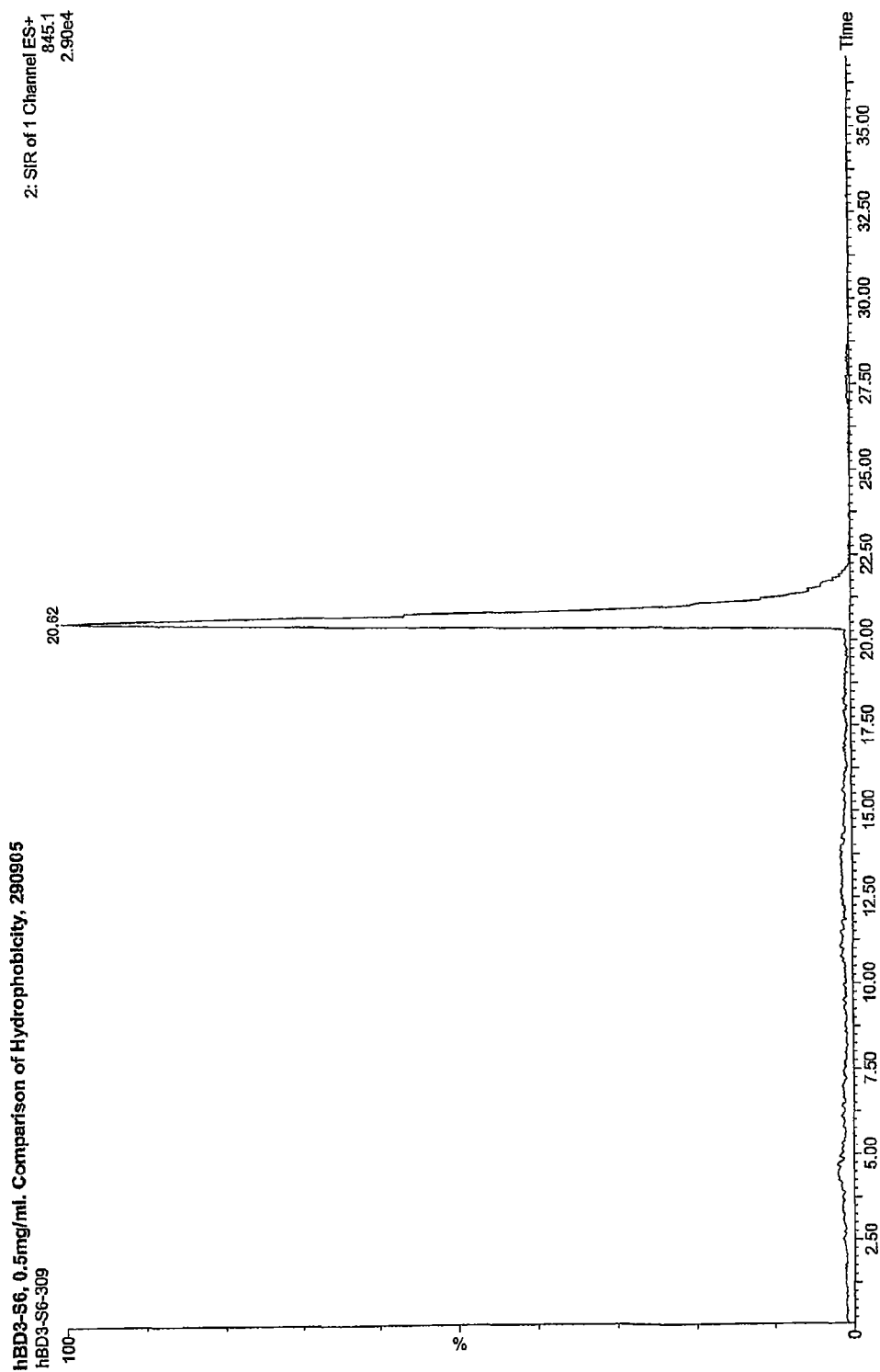
Figure 12B SIR chromatogram at m/z = 845.1 ($[M+6H]^{6+}$)

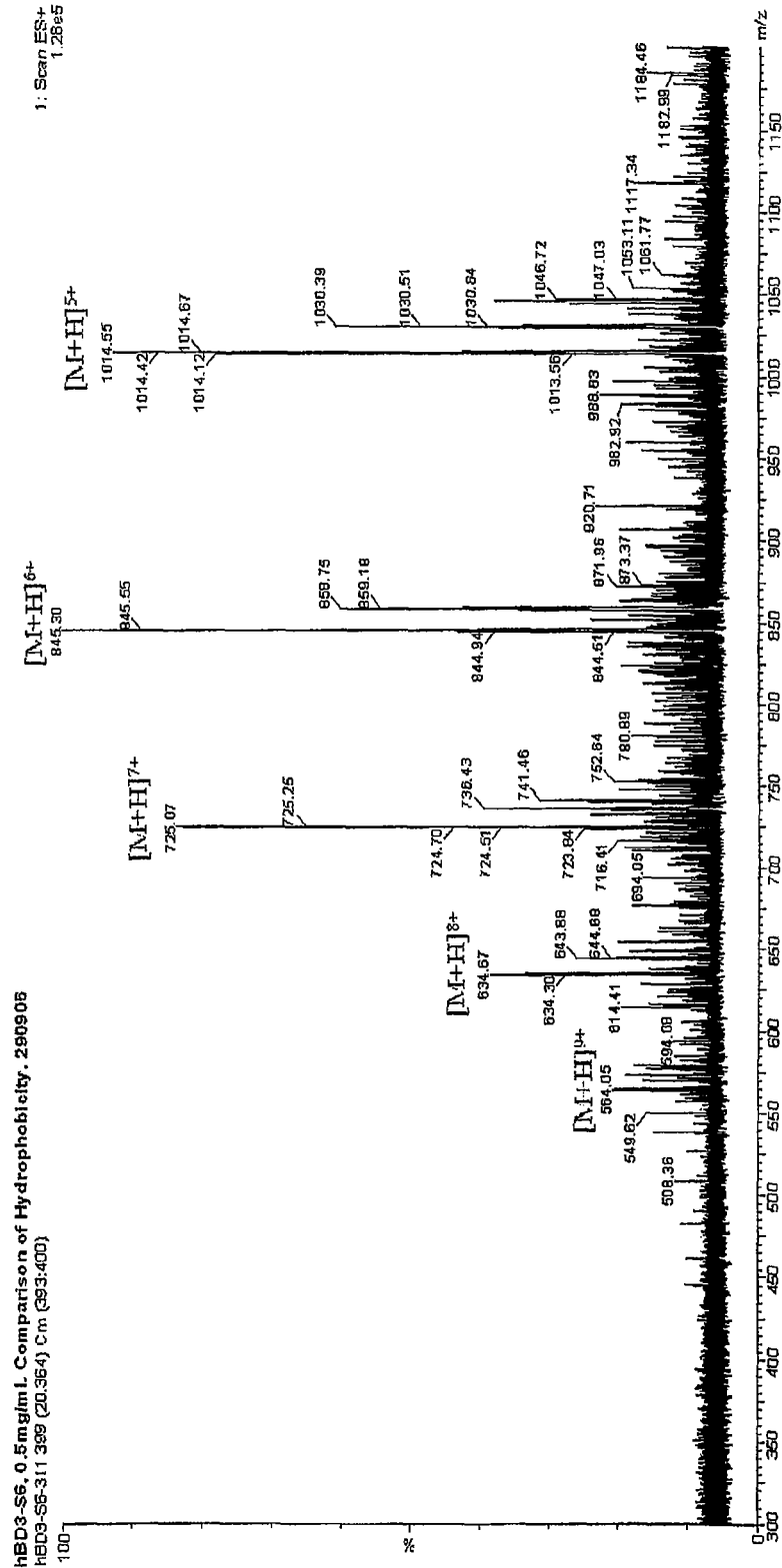
Figure 12C ES + MS spectrum

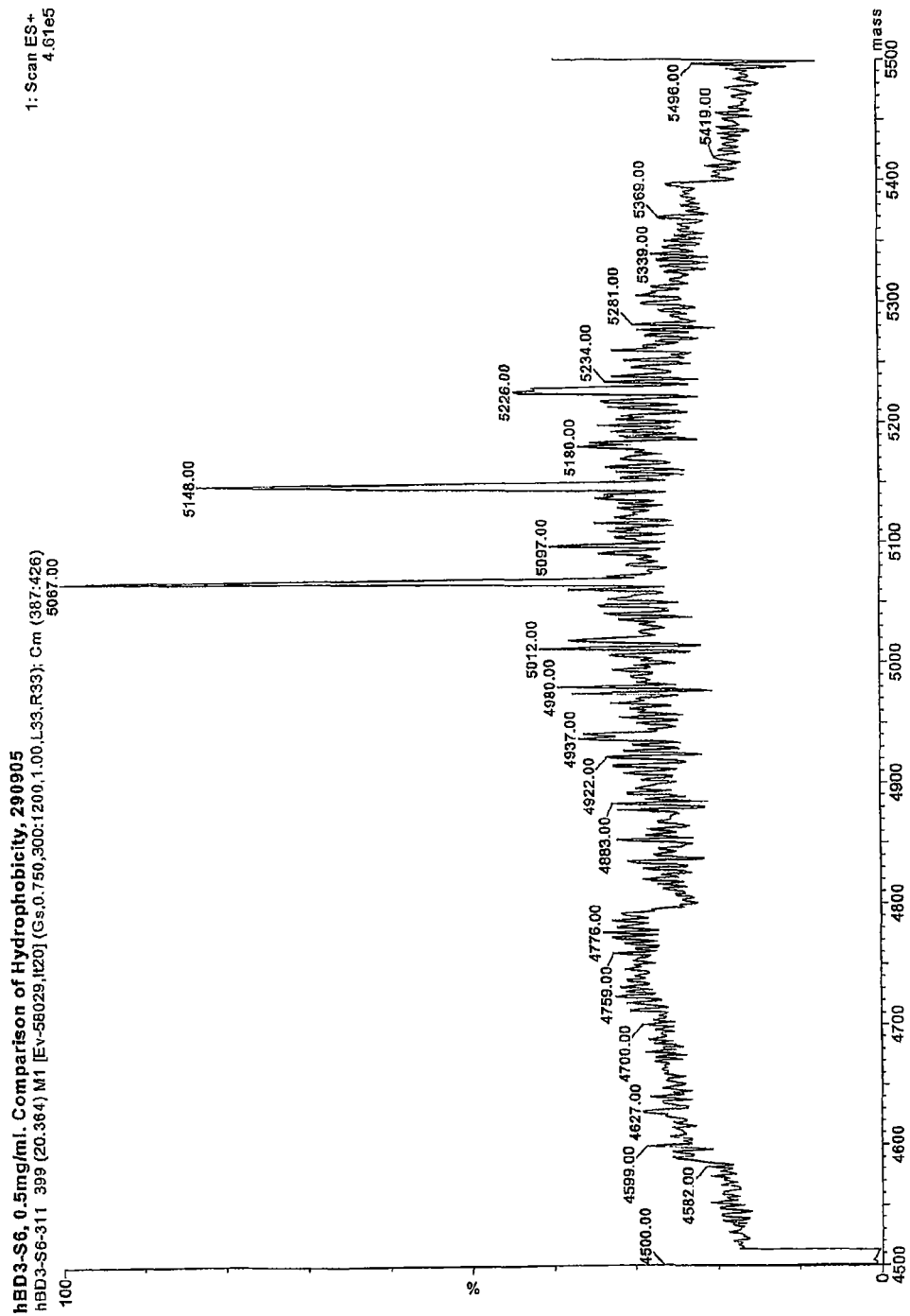
Figure 12D Deconvoluted MS spectrum

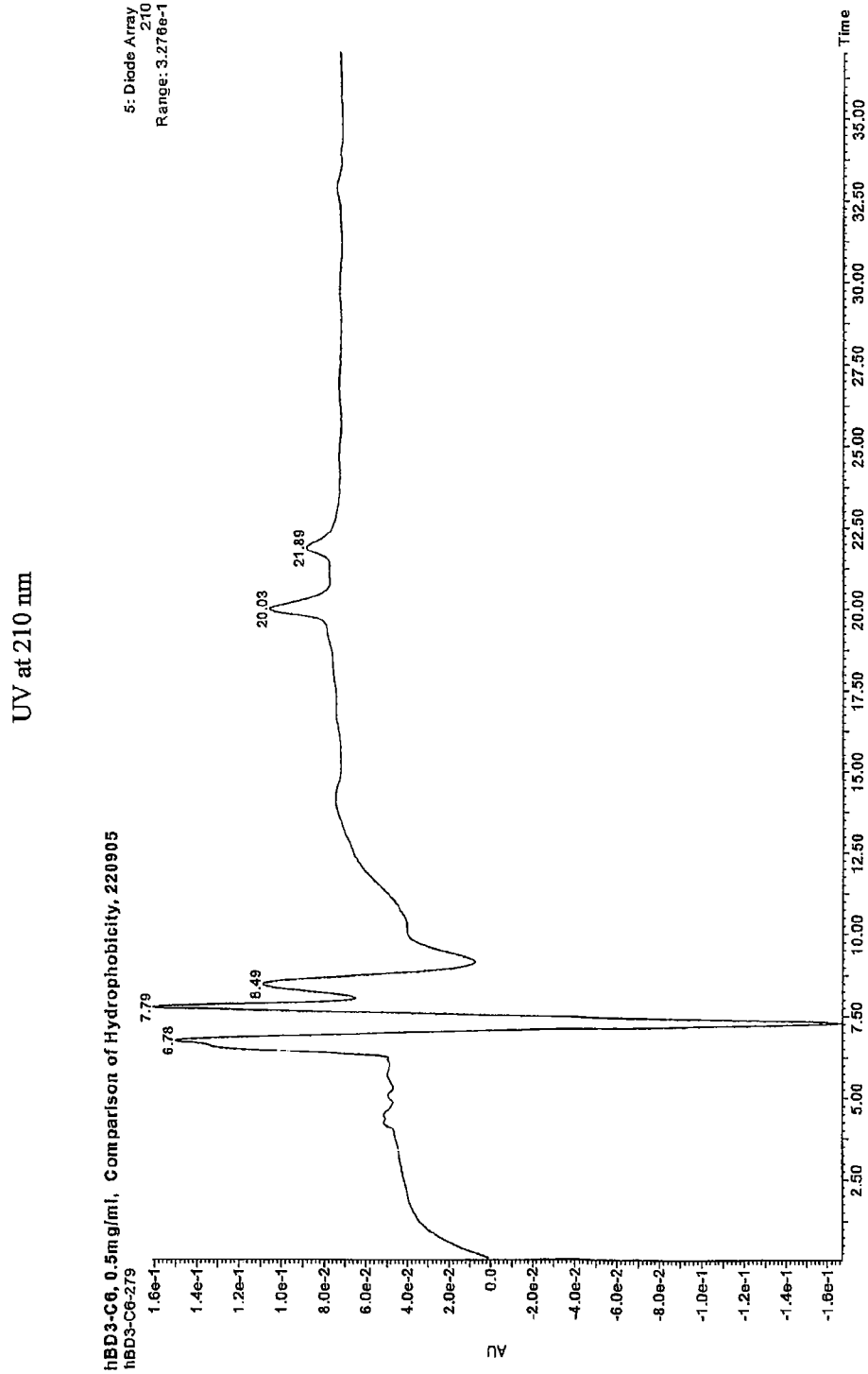
Figure 13A RP-HPLC-UV chromatogram and MS spectrum of C6 (sometimes coded C(Acm)6
UV at 210 nm

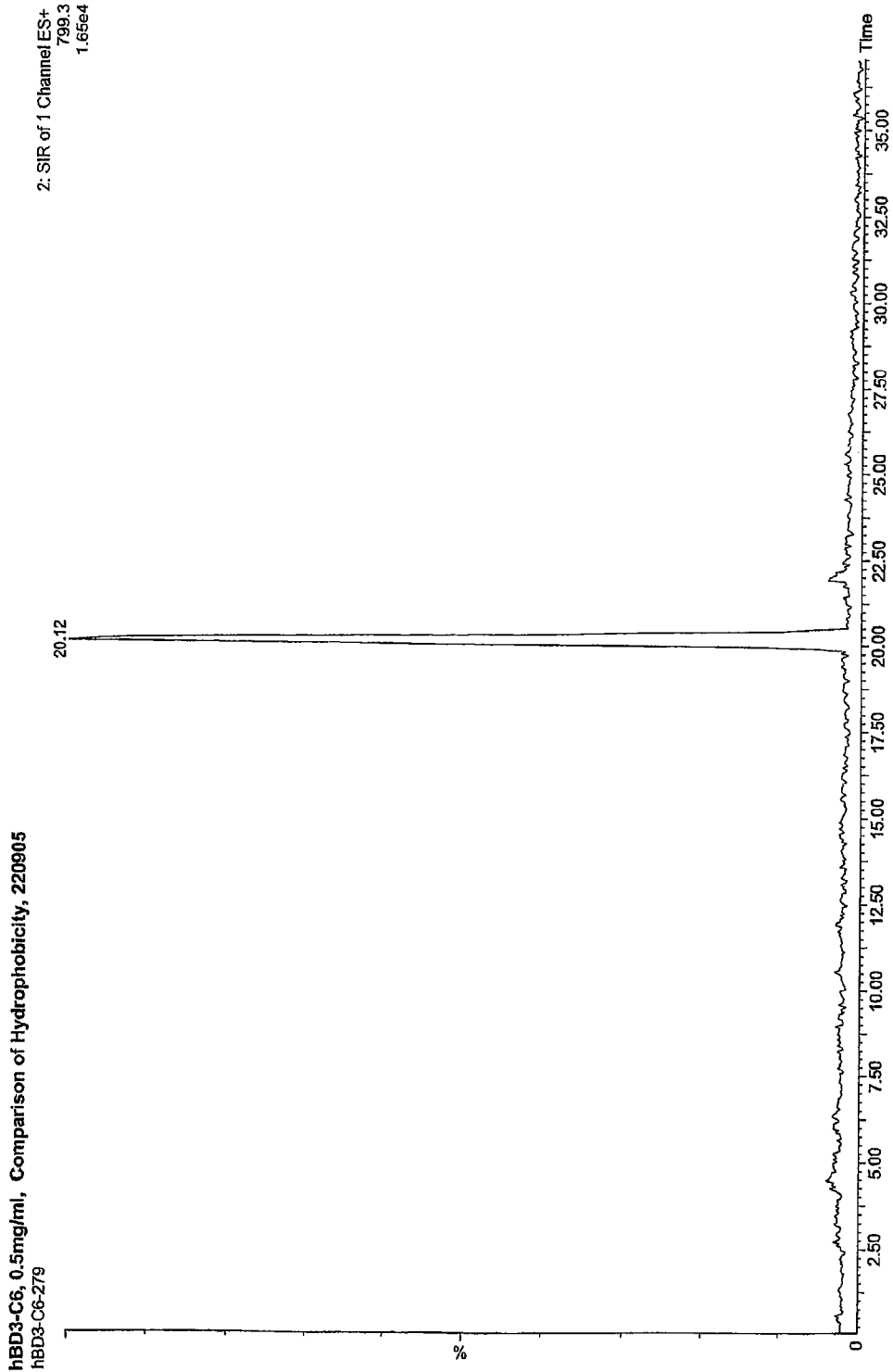
Figure 13B SIR chromatogram at m/z = 799.3 ([M+7H]$^{7+}$)

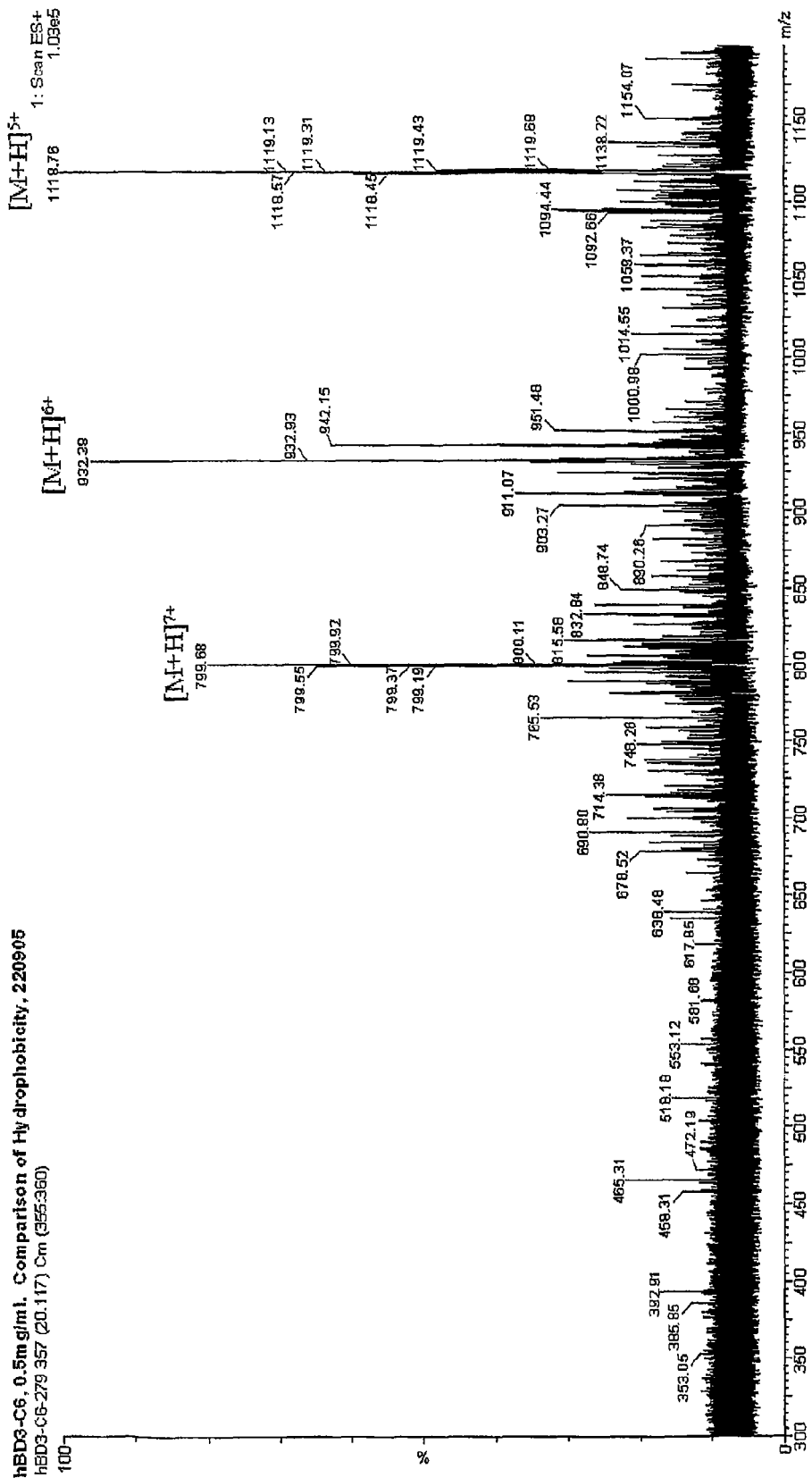
Figure 13C ES + MS spectrum

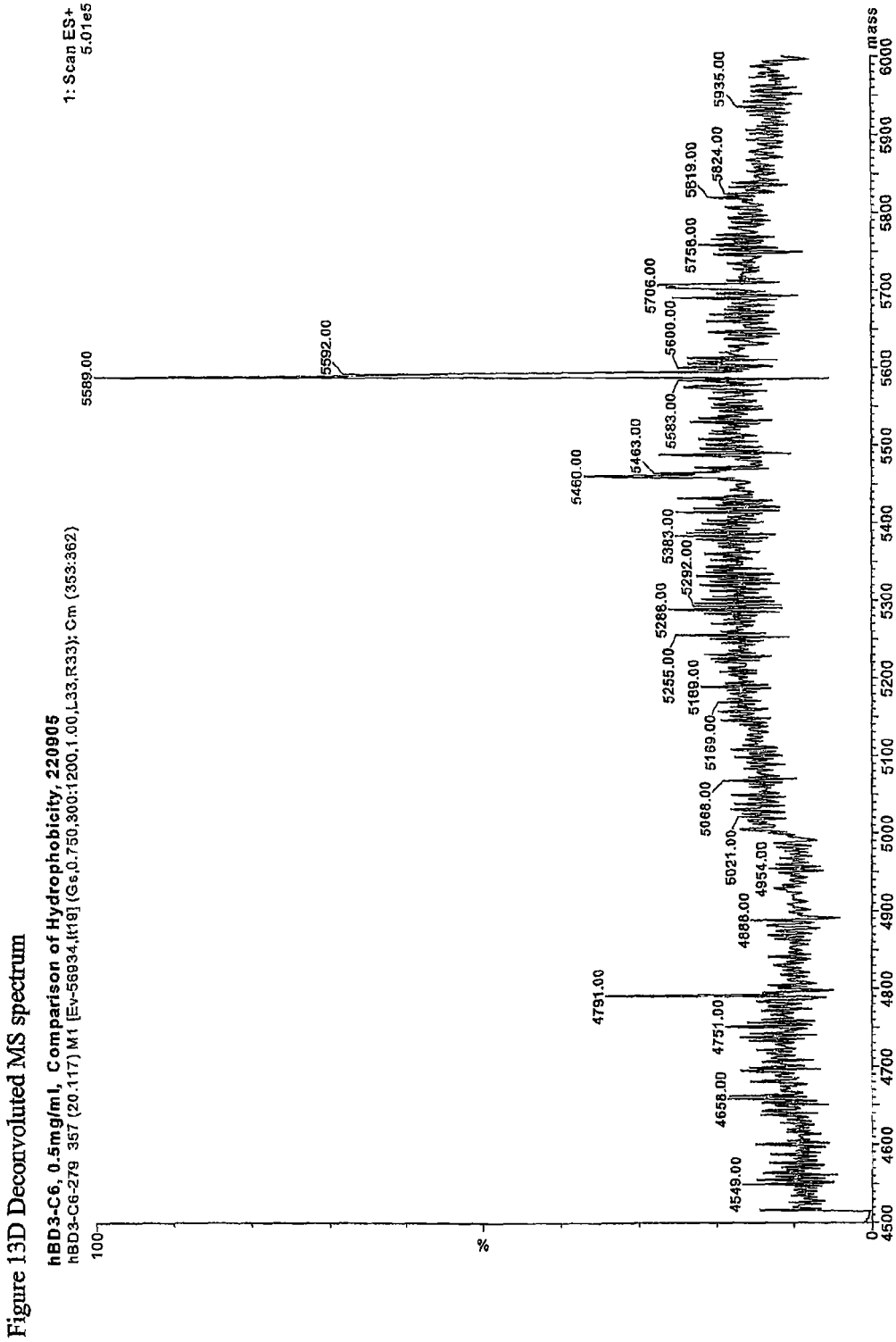
Figure 13D Deconvoluted MS spectrum

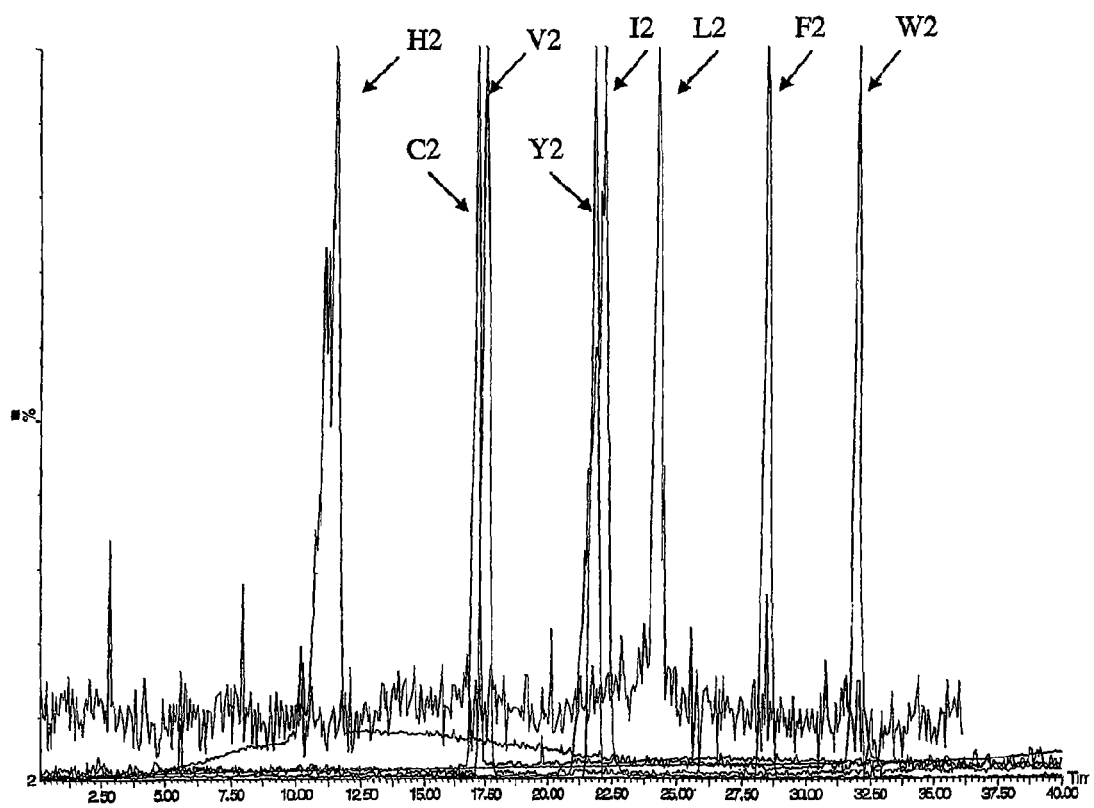
Figure 14 Comparison of overall molecular hydrophobicity of C-Terminus fragment peptides of hBD3 in terms of retention time of SIR chromatogram of charged fragments of peptides Figure 15 Cytotoxicity of peptides vs concentration
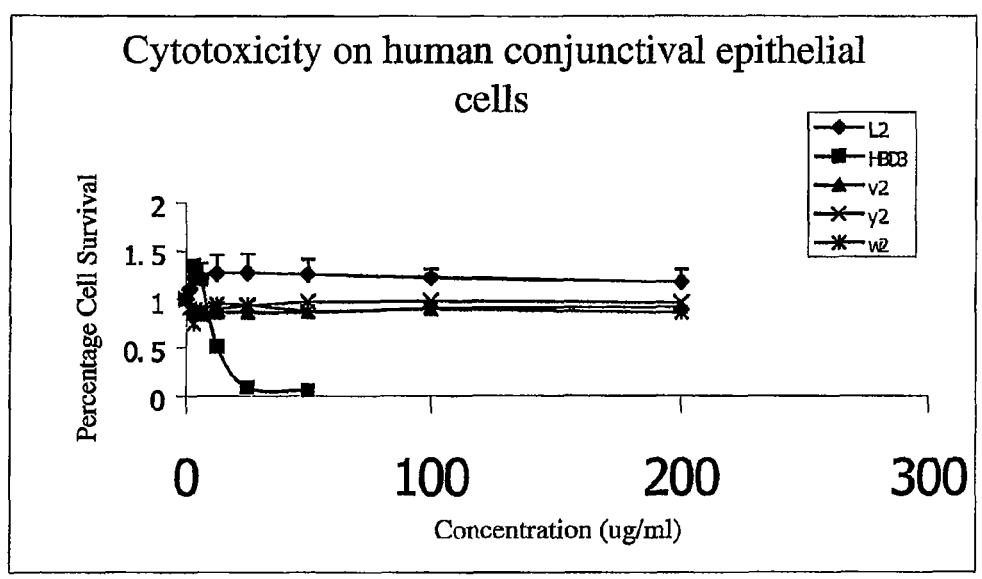

SEQUENCE LISTING

```
<160> NUMBER OF SEQ ID NOS: 45

<210> SEQ ID NO 1
<211> LENGTH: 45
<212> TYPE: PRT
<213> ORGANISM: Homo sapiens

<400> SEQUENCE: 1

Gly Ile Ile Asn Thr Leu Gln Lys Tyr Tyr Cys Arg Val Arg Gly Gly
1               5                   10                  15

Arg Cys Ala Val Leu Ser Cys Leu Pro Lys Glu Glu Gln Ile Gly Lys
            20                  25                  30

Cys Ser Thr Arg Gly Arg Lys Cys Cys Arg Arg Lys Lys
        35                  40                  45

<210> SEQ ID NO 2
<211> LENGTH: 45
<212> TYPE: PRT
<213> ORGANISM: artificial
<220> FEATURE:
<223> OTHER INFORMATION: peptide derived from hBD3, C replaced with X
<220> FEATURE:
<221> NAME/KEY: MISC_FEATURE
<222> LOCATION: (11)..(41)
<223> OTHER INFORMATION: Xaa is an amino acid except cysteine, a
      protected cysteine residue ro derivative thereof except c[Abu]; or
      the amino acid is not present

<400> SEQUENCE: 2

Gly Ile Ile Asn Thr Leu Gln Lys Tyr Tyr Xaa Arg Val Arg Gly Gly
1               5                   10                  15

Arg Xaa Ala Val Leu Ser Xaa Leu Pro Lys Glu Glu Gln Ile Gly Lys
```

```
                    20                  25                  30
Xaa Ser Thr Arg Gly Arg Lys Xaa Xaa Arg Arg Lys Lys
        35                  40                  45

<210> SEQ ID NO 3
<211> LENGTH: 38
<212> TYPE: PRT
<213> ORGANISM: artificial
<220> FEATURE:
<223> OTHER INFORMATION: 38 aa hBD3 derived peptide (C terminus), C
      replaced with X
<220> FEATURE:
<221> NAME/KEY: MISC_FEATURE
<222> LOCATION: (4)..(34)
<223> OTHER INFORMATION: Xaa is an amino acid except cysteine, a
      protected cysteine residue ro derivative thereof except c[Abu]; or
      the amino acid is not present

<400> SEQUENCE: 3

Lys Tyr Tyr Xaa Arg Val Arg Gly Gly Arg Xaa Ala Val Leu Ser Xaa
1               5                   10                  15

Leu Pro Lys Glu Glu Gln Ile Gly Lys Xaa Ser Thr Arg Gly Arg Lys
            20                  25                  30

Xaa Xaa Arg Arg Lys Lys
        35

<210> SEQ ID NO 4
<211> LENGTH: 36
<212> TYPE: PRT
<213> ORGANISM: artificial
<220> FEATURE:
<223> OTHER INFORMATION: 36 aa hBD3 derived peptide (C terminus), C
      replaced with X
<220> FEATURE:
<221> NAME/KEY: MISC_FEATURE
<222> LOCATION: (2)..(32)
<223> OTHER INFORMATION: Xaa is an amino acid except cysteine, a
      protected cysteine residue ro derivative thereof except c[Abu]; or
      the amino acid is not present

<400> SEQUENCE: 4

Tyr Xaa Arg Val Arg Gly Gly Arg Xaa Ala Val Leu Ser Xaa Leu Pro
1               5                   10                  15

Lys Glu Glu Gln Ile Gly Lys Xaa Ser Thr Arg Gly Arg Lys Xaa Xaa
            20                  25                  30

Arg Arg Lys Lys
        35

<210> SEQ ID NO 5
<211> LENGTH: 40
<212> TYPE: PRT
<213> ORGANISM: artificial
<220> FEATURE:
<223> OTHER INFORMATION: 40 aa hBD3 derived peptide (C terminus), C
      replaced with X
<220> FEATURE:
<221> NAME/KEY: MISC_FEATURE
<222> LOCATION: (6)..(36)
<223> OTHER INFORMATION: Xaa is an amino acid except cysteine, a
      protected cysteine residue ro derivative thereof except c[Abu]; or
      the amino acid is not present

<400> SEQUENCE: 5

Leu Gln Lys Tyr Tyr Xaa Arg Val Arg Gly Gly Arg Xaa Ala Val Leu
1               5                   10                  15

Ser Xaa Leu Pro Lys Glu Glu Gln Ile Gly Lys Xaa Ser Thr Arg Gly
            20                  25                  30
```

```
Arg Lys Xaa Xaa Arg Arg Lys Lys
        35              40

<210> SEQ ID NO 6
<211> LENGTH: 29
<212> TYPE: PRT
<213> ORGANISM: artificial
<220> FEATURE:
<223> OTHER INFORMATION: 29 aa hD3 derived peptide (C terminus), C
      replaced with X
<220> FEATURE:
<221> NAME/KEY: MISC_FEATURE
<222> LOCATION: (2)..(25)
<223> OTHER INFORMATION: Xaa is an amino acid except cysteine, a
      protected cysteine residue ro derivative thereof except c[Abu]; or
      the amino acid is not present

<400> SEQUENCE: 6

Arg Xaa Ala Val Leu Ser Xaa Leu Pro Lys Glu Glu Gln Ile Gly Lys
1               5                   10                  15

Xaa Ser Thr Arg Gly Arg Lys Xaa Xaa Arg Arg Lys Lys
            20                  25

<210> SEQ ID NO 7
<211> LENGTH: 20
<212> TYPE: PRT
<213> ORGANISM: artificial
<220> FEATURE:
<223> OTHER INFORMATION: 20 aa hBD3 derived peptide (C terminus), C
      replaced with X
<220> FEATURE:
<221> NAME/KEY: MISC_FEATURE
<222> LOCATION: (8)..(16)
<223> OTHER INFORMATION: Xaa is any amino acid except cysteine; a
      protected cysteine residue or derivative thereof except C[Abu]; or
      the amino acid is not present.

<400> SEQUENCE: 7

Lys Glu Glu Gln Ile Gly Lys Xaa Ser Thr Arg Gly Arg Lys Xaa Xaa
1               5                   10                  15

Arg Arg Lys Lys
            20

<210> SEQ ID NO 8
<211> LENGTH: 14
<212> TYPE: PRT
<213> ORGANISM: artificial
<220> FEATURE:
<223> OTHER INFORMATION: 14 aa hBD3 derived peptide (C terminus), C
      replaced with X
<220> FEATURE:
<221> NAME/KEY: MISC_FEATURE
<222> LOCATION: (2)..(10)
<223> OTHER INFORMATION: Xaa is any amino acid except cysteine; a
      protected cysteine residue or derivative thereof except C[Abu]; or
      the amino acid is not present.

<400> SEQUENCE: 8

Lys Xaa Ser Thr Arg Gly Arg Lys Xaa Xaa Arg Arg Lys Lys
1               5                   10

<210> SEQ ID NO 9
<211> LENGTH: 10
<212> TYPE: PRT
<213> ORGANISM: artificial
<220> FEATURE:
<223> OTHER INFORMATION: 10 aa hBD3 derived peptide (C terminus), C
      replaced with X
<220> FEATURE:
<221> NAME/KEY: MISC_FEATURE
<222> LOCATION: (5)..(6)
```

```
<223> OTHER INFORMATION: Xaa is any amino acid except cysteine; a
      protected cysteine residue or derivative thereof except C[Abu]; or
      the amino acid is not present.

<400> SEQUENCE: 9

Arg Gly Arg Lys Xaa Xaa Arg Arg Lys Lys
1               5                   10

<210> SEQ ID NO 10
<211> LENGTH: 9
<212> TYPE: PRT
<213> ORGANISM: artificial
<220> FEATURE:
<223> OTHER INFORMATION: 9 aa hBD3 derived peptide (C terminus), C
      replaced with X
<220> FEATURE:
<221> NAME/KEY: MISC_FEATURE
<222> LOCATION: (5)..(6)
<223> OTHER INFORMATION: Xaa is any amino acid except cysteine; a
      protected cysteine residue or derivative thereof except C[Abu]; or
      the amino acid is not present.

<400> SEQUENCE: 10

Arg Gly Arg Lys Xaa Xaa Arg Arg Lys
1               5

<210> SEQ ID NO 11
<211> LENGTH: 19
<212> TYPE: PRT
<213> ORGANISM: artificial
<220> FEATURE:
<223> OTHER INFORMATION: 19 aa hBD3 derived peptide (aa 8 to 26), C
      replaced with X
<220> FEATURE:
<221> NAME/KEY: MISC_FEATURE
<222> LOCATION: (4)..(16)
<223> OTHER INFORMATION: Xaa is any any amino acid except cysteine; a
      protected cysteine residue or derivative thereof except C[Abu]; or
      the amino acid is not present.

<400> SEQUENCE: 11

Lys Tyr Tyr Xaa Arg Val Arg Gly Gly Arg Xaa Ala Val Leu Ser Xaa
1               5                   10                  15

Leu Pro Lys

<210> SEQ ID NO 12
<211> LENGTH: 17
<212> TYPE: PRT
<213> ORGANISM: artificial
<220> FEATURE:
<223> OTHER INFORMATION: 17 aa hBD3 derived peptide (N terminus), C
      replaced with X
<220> FEATURE:
<221> NAME/KEY: MISC_FEATURE
<222> LOCATION: (11)..(11)
<223> OTHER INFORMATION: Xaa is any amino acid except cysteine; a
      protected cysteine residue or derivative thereof except C[Abu]; or
      the amino acid is not present.

<400> SEQUENCE: 12

Gly Ile Ile Asn Thr Leu Gln Lys Tyr Tyr Xaa Arg Val Arg Gly Gly
1               5                   10                  15

Arg

<210> SEQ ID NO 13
<211> LENGTH: 45
<212> TYPE: PRT
<213> ORGANISM: artificial
<220> FEATURE:
<223> OTHER INFORMATION: hBD3 derived peptide, C replaced with W
```

```
<400> SEQUENCE: 13

Gly Ile Ile Asn Thr Leu Gln Lys Tyr Tyr Trp Arg Val Arg Gly Gly
1               5                   10                  15

Arg Trp Ala Val Leu Ser Trp Leu Pro Lys Glu Glu Gln Ile Gly Lys
            20                  25                  30

Trp Ser Thr Arg Gly Arg Lys Trp Trp Arg Arg Lys Lys
        35                  40                  45

<210> SEQ ID NO 14
<211> LENGTH: 45
<212> TYPE: PRT
<213> ORGANISM: artificial
<220> FEATURE:
<223> OTHER INFORMATION: hBD3 derived peptide, C replaced with F

<400> SEQUENCE: 14

Gly Ile Ile Asn Thr Leu Gln Lys Tyr Tyr Phe Arg Val Arg Gly Gly
1               5                   10                  15

Arg Phe Ala Val Leu Ser Phe Leu Pro Lys Glu Glu Gln Ile Gly Lys
            20                  25                  30

Phe Ser Thr Arg Gly Arg Lys Phe Phe Arg Arg Lys Lys
        35                  40                  45

<210> SEQ ID NO 15
<211> LENGTH: 45
<212> TYPE: PRT
<213> ORGANISM: artificial
<220> FEATURE:
<223> OTHER INFORMATION: hBD3 derived peptide, C replaced with Y

<400> SEQUENCE: 15

Gly Ile Ile Asn Thr Leu Gln Lys Tyr Tyr Tyr Arg Val Arg Gly Gly
1               5                   10                  15

Arg Tyr Ala Val Leu Ser Tyr Leu Pro Lys Glu Glu Gln Ile Gly Lys
            20                  25                  30

Tyr Ser Thr Arg Gly Arg Lys Tyr Tyr Arg Arg Lys Lys
        35                  40                  45

<210> SEQ ID NO 16
<211> LENGTH: 45
<212> TYPE: PRT
<213> ORGANISM: artificial
<220> FEATURE:
<223> OTHER INFORMATION: hBD3 derived peptide, C replaced with S

<400> SEQUENCE: 16

Gly Ile Ile Asn Thr Leu Gln Lys Tyr Tyr Ser Arg Val Arg Gly Gly
1               5                   10                  15

Arg Ser Ala Val Leu Ser Ser Leu Pro Lys Glu Glu Gln Ile Gly Lys
            20                  25                  30

Ser Ser Thr Arg Gly Arg Lys Ser Ser Arg Arg Lys Lys
        35                  40                  45

<210> SEQ ID NO 17
<211> LENGTH: 45
<212> TYPE: PRT
<213> ORGANISM: artificial
<220> FEATURE:
<223> OTHER INFORMATION: hBD3 derived peptide, C replaced with A

<400> SEQUENCE: 17

Gly Ile Ile Asn Thr Leu Gln Lys Tyr Tyr Ala Arg Val Arg Gly Gly
```

```
                  1               5                  10                 15
Arg Ala Ala Val Leu Ser Ala Leu Pro Lys Glu Glu Gln Ile Gly Lys
             20                  25                 30

Ala Ser Thr Arg Gly Arg Lys Ala Ala Arg Arg Lys Lys
         35                  40                 45

<210> SEQ ID NO 18
<211> LENGTH: 45
<212> TYPE: PRT
<213> ORGANISM: artificial
<220> FEATURE:
<223> OTHER INFORMATION: hBD3 derived peptide, C replaced with C(Acm)
<220> FEATURE:
<221> NAME/KEY: MISC_FEATURE
<222> LOCATION: (11)..(41)
<223> OTHER INFORMATION: Xaa is C(Acm)

<400> SEQUENCE: 18

Gly Ile Ile Asn Thr Leu Gln Lys Tyr Tyr Xaa Arg Val Arg Gly Gly
1               5                   10                  15

Arg Xaa Ala Val Leu Ser Xaa Leu Pro Lys Glu Glu Gln Ile Gly Lys
            20                  25                  30

Xaa Ser Thr Arg Gly Arg Lys Xaa Xaa Arg Arg Lys Lys
        35                  40                  45

<210> SEQ ID NO 19
<211> LENGTH: 45
<212> TYPE: PRT
<213> ORGANISM: artificial
<220> FEATURE:
<223> OTHER INFORMATION: hBD3 derived peptide, C replaced with C(But)
<220> FEATURE:
<221> NAME/KEY: MISC_FEATURE
<222> LOCATION: (11)..(41)
<223> OTHER INFORMATION: Xaa is C(But)

<400> SEQUENCE: 19

Gly Ile Ile Asn Thr Leu Gln Lys Tyr Tyr Xaa Arg Val Arg Gly Gly
1               5                   10                  15

Arg Xaa Ala Val Leu Ser Xaa Leu Pro Lys Glu Glu Gln Ile Gly Lys
            20                  25                  30

Xaa Ser Thr Arg Gly Arg Lys Xaa Xaa Arg Arg Lys Lys
        35                  40                  45

<210> SEQ ID NO 20
<211> LENGTH: 45
<212> TYPE: PRT
<213> ORGANISM: artificial
<220> FEATURE:
<223> OTHER INFORMATION: hBD3 derived peptide, C replaced with
      C(t-Buthio)
<220> FEATURE:
<221> NAME/KEY: MISC_FEATURE
<222> LOCATION: (11)..(41)
<223> OTHER INFORMATION: Xaa is C(t-Buthio)

<400> SEQUENCE: 20

Gly Ile Ile Asn Thr Leu Gln Lys Tyr Tyr Xaa Arg Val Arg Gly Gly
1               5                   10                  15

Arg Xaa Ala Val Leu Ser Xaa Leu Pro Lys Glu Glu Gln Ile Gly Lys
            20                  25                  30

Xaa Ser Thr Arg Gly Arg Lys Xaa Xaa Arg Arg Lys Lys
        35                  40                  45

<210> SEQ ID NO 21
```

```
<211> LENGTH: 45
<212> TYPE: PRT
<213> ORGANISM: artificial
<220> FEATURE:
<223> OTHER INFORMATION: hBD3 derived peptide, C replaced with C(Bzl)
<220> FEATURE:
<221> NAME/KEY: MISC_FEATURE
<222> LOCATION: (11)..(41)
<223> OTHER INFORMATION: Xaa is C(Bzl)

<400> SEQUENCE: 21

Gly Ile Ile Asn Thr Leu Gln Lys Tyr Tyr Xaa Arg Val Arg Gly Gly
1               5                   10                  15

Arg Xaa Ala Val Leu Ser Xaa Leu Pro Lys Glu Glu Gln Ile Gly Lys
            20                  25                  30

Xaa Ser Thr Arg Gly Arg Lys Xaa Xaa Arg Arg Lys Lys
        35                  40                  45

<210> SEQ ID NO 22
<211> LENGTH: 45
<212> TYPE: PRT
<213> ORGANISM: artificial
<220> FEATURE:
<223> OTHER INFORMATION: hBD3 derived peptide, C replaced with
      C(4-MeBzl)
<220> FEATURE:
<221> NAME/KEY: MISC_FEATURE
<222> LOCATION: (11)..(41)
<223> OTHER INFORMATION: Xaa is C(4-MeBzl)

<400> SEQUENCE: 22

Gly Ile Ile Asn Thr Leu Gln Lys Tyr Tyr Xaa Arg Val Arg Gly Gly
1               5                   10                  15

Arg Xaa Ala Val Leu Ser Xaa Leu Pro Lys Glu Glu Gln Ile Gly Lys
            20                  25                  30

Xaa Ser Thr Arg Gly Arg Lys Xaa Xaa Arg Arg Lys Lys
        35                  40                  45

<210> SEQ ID NO 23
<211> LENGTH: 45
<212> TYPE: PRT
<213> ORGANISM: artificial
<220> FEATURE:
<223> OTHER INFORMATION: hBD3 derived peptide, C replaced with
      C(4-MeBzl)
<220> FEATURE:
<221> NAME/KEY: MISC_FEATURE
<222> LOCATION: (11)..(41)
<223> OTHER INFORMATION: Xaa is C(4-MeO-Bzl)

<400> SEQUENCE: 23

Gly Ile Ile Asn Thr Leu Gln Lys Tyr Tyr Xaa Arg Val Arg Gly Gly
1               5                   10                  15

Arg Xaa Ala Val Leu Ser Xaa Leu Pro Lys Glu Glu Gln Ile Gly Lys
            20                  25                  30

Xaa Ser Thr Arg Gly Arg Lys Xaa Xaa Arg Arg Lys Lys
        35                  40                  45

<210> SEQ ID NO 24
<211> LENGTH: 45
<212> TYPE: PRT
<213> ORGANISM: artificial
<220> FEATURE:
<223> OTHER INFORMATION: hBD3 derived peptide, C replaced with C(MMt)
<220> FEATURE:
<221> NAME/KEY: MISC_FEATURE
<222> LOCATION: (11)..(41)
<223> OTHER INFORMATION: Xaa is C(Mmt)
```

```
<400> SEQUENCE: 24

Gly Ile Ile Asn Thr Leu Gln Lys Tyr Tyr Xaa Arg Val Arg Gly Gly
1               5                   10                  15

Arg Xaa Ala Val Leu Ser Xaa Leu Pro Lys Glu Glu Gln Ile Gly Lys
            20                  25                  30

Xaa Ser Thr Arg Gly Arg Lys Xaa Xaa Arg Arg Lys Lys
        35                  40                  45

<210> SEQ ID NO 25
<211> LENGTH: 45
<212> TYPE: PRT
<213> ORGANISM: artificial
<220> FEATURE:
<223> OTHER INFORMATION: hBD3 derived peptide, C replaced with C(Cam)
<220> FEATURE:
<221> NAME/KEY: MISC_FEATURE
<222> LOCATION: (11)..(41)
<223> OTHER INFORMATION: Xaa is C(Cam)

<400> SEQUENCE: 25

Gly Ile Ile Asn Thr Leu Gln Lys Tyr Tyr Xaa Arg Val Arg Gly Gly
1               5                   10                  15

Arg Xaa Ala Val Leu Ser Xaa Leu Pro Lys Glu Glu Gln Ile Gly Lys
            20                  25                  30

Xaa Ser Thr Arg Gly Arg Lys Xaa Xaa Arg Arg Lys Lys
        35                  40                  45

<210> SEQ ID NO 26
<211> LENGTH: 45
<212> TYPE: PRT
<213> ORGANISM: artificial
<220> FEATURE:
<223> OTHER INFORMATION: hBD3 derived peptide, 1st and 5th Cs replaced
      with C(Acm)
<220> FEATURE:
<221> NAME/KEY: MISC_FEATURE
<222> LOCATION: (11)..(40)
<223> OTHER INFORMATION: X is C(Acm)

<400> SEQUENCE: 26

Gly Ile Ile Asn Thr Leu Gln Lys Tyr Tyr Xaa Arg Val Arg Gly Gly
1               5                   10                  15

Arg Cys Ala Val Leu Ser Cys Leu Pro Lys Glu Glu Gln Ile Gly Lys
            20                  25                  30

Cys Ser Thr Arg Gly Arg Lys Xaa Cys Arg Arg Lys Lys
        35                  40                  45

<210> SEQ ID NO 27
<211> LENGTH: 45
<212> TYPE: PRT
<213> ORGANISM: artificial
<220> FEATURE:
<223> OTHER INFORMATION: hBD3 derived peptide, 1st and 6th Cs replaced
      with C(Acm)
<220> FEATURE:
<221> NAME/KEY: MISC_FEATURE
<222> LOCATION: (11)..(41)
<223> OTHER INFORMATION: Xaa is C(Acm)

<400> SEQUENCE: 27

Gly Ile Ile Asn Thr Leu Gln Lys Tyr Tyr Xaa Arg Val Arg Gly Gly
1               5                   10                  15

Arg Cys Ala Val Leu Ser Cys Leu Pro Lys Glu Glu Gln Ile Gly Lys
            20                  25                  30
```

```
Cys Ser Thr Arg Gly Arg Lys Cys Xaa Arg Arg Lys Lys
            35                  40                  45

<210> SEQ ID NO 28
<211> LENGTH: 45
<212> TYPE: PRT
<213> ORGANISM: artificial
<220> FEATURE:
<223> OTHER INFORMATION: hBD3 derived peptide, C replaced with C(Abu)
<220> FEATURE:
<221> NAME/KEY: MISC_FEATURE
<222> LOCATION: (11)..(41)
<223> OTHER INFORMATION: Xaa is C[Abu]

<400> SEQUENCE: 28

Gly Ile Ile Asn Thr Leu Gln Lys Tyr Tyr Xaa Arg Val Arg Gly Gly
1               5                   10                  15

Arg Xaa Ala Val Leu Ser Xaa Leu Pro Lys Glu Glu Gln Ile Gly Lys
            20                  25                  30

Xaa Ser Thr Arg Gly Arg Lys Xaa Xaa Arg Arg Lys Lys
            35                  40                  45

<210> SEQ ID NO 29
<211> LENGTH: 38
<212> TYPE: PRT
<213> ORGANISM: artificial
<220> FEATURE:
<223> OTHER INFORMATION: 38 aa hBD3 derived peptide (C terminus)

<400> SEQUENCE: 29

Lys Tyr Tyr Cys Arg Val Arg Gly Gly Arg Cys Ala Val Leu Ser Cys
1               5                   10                  15

Leu Pro Lys Glu Glu Gln Ile Gly Lys Cys Ser Thr Arg Gly Arg Lys
            20                  25                  30

Cys Cys Arg Arg Lys Lys
            35

<210> SEQ ID NO 30
<211> LENGTH: 36
<212> TYPE: PRT
<213> ORGANISM: artificial
<220> FEATURE:
<223> OTHER INFORMATION: 36 aa hBD3 derived peptide (C terminus)

<400> SEQUENCE: 30

Tyr Cys Arg Val Arg Gly Gly Arg Cys Ala Val Leu Ser Cys Leu Pro
1               5                   10                  15

Lys Glu Glu Gln Ile Gly Lys Cys Ser Thr Arg Gly Arg Lys Cys Cys
            20                  25                  30

Arg Arg Lys Lys
            35

<210> SEQ ID NO 31
<211> LENGTH: 20
<212> TYPE: PRT
<213> ORGANISM: artificial
<220> FEATURE:
<223> OTHER INFORMATION: 20 aa hBD3 derived peptide (C terminus), C
      replaced with C

<400> SEQUENCE: 31

Lys Glu Glu Gln Ile Gly Lys Ser Ser Thr Arg Gly Arg Lys Ser Ser
1               5                   10                  15

Arg Arg Lys Lys
            20
```

```
<210> SEQ ID NO 32
<211> LENGTH: 14
<212> TYPE: PRT
<213> ORGANISM: artificial
<220> FEATURE:
<223> OTHER INFORMATION: 14 aa hBD3 derived peptide (C terminus), C
      replaced with S

<400> SEQUENCE: 32

Lys Ser Ser Thr Arg Gly Arg Lys Ser Ser Arg Arg Lys Lys
1               5                   10

<210> SEQ ID NO 33
<211> LENGTH: 10
<212> TYPE: PRT
<213> ORGANISM: artificial
<220> FEATURE:
<223> OTHER INFORMATION: 10 aa hBD3 derived peptide (C terminus), C
      replaced with S

<400> SEQUENCE: 33

Arg Gly Arg Lys Ser Ser Arg Arg Lys Lys
1               5                   10

<210> SEQ ID NO 34
<211> LENGTH: 9
<212> TYPE: PRT
<213> ORGANISM: artificial
<220> FEATURE:
<223> OTHER INFORMATION: 9 aa hBD3 derived peptide (C terminus), C
      replaced with S

<400> SEQUENCE: 34

Arg Gly Arg Lys Ser Ser Arg Arg Lys
1               5

<210> SEQ ID NO 35
<211> LENGTH: 19
<212> TYPE: PRT
<213> ORGANISM: artificial
<220> FEATURE:
<223> OTHER INFORMATION: 19 aa hBD3 derived peptide (aa 4 to 26), C
      replaced with S

<400> SEQUENCE: 35

Lys Tyr Tyr Ser Arg Val Arg Gly Gly Arg Ser Ala Val Leu Ser Ser
1               5                   10                  15

Leu Pro Lys

<210> SEQ ID NO 36
<211> LENGTH: 17
<212> TYPE: PRT
<213> ORGANISM: artificial
<220> FEATURE:
<223> OTHER INFORMATION: 17 aa hBD3 derived peptide (N terminus), C
      replaced with S

<400> SEQUENCE: 36

Gly Ile Ile Asn Thr Leu Gln Lys Tyr Tyr Ser Arg Val Arg Gly Gly
1               5                   10                  15

Arg

<210> SEQ ID NO 37
<211> LENGTH: 10
<212> TYPE: PRT
<213> ORGANISM: artificial
```

```
<220> FEATURE:
<223> OTHER INFORMATION: 10 aa hBD3 derived peptide (C-terminus)

<400> SEQUENCE: 37

Arg Gly Arg Lys Cys Cys Arg Arg Lys Lys
1               5                   10

<210> SEQ ID NO 38
<211> LENGTH: 10
<212> TYPE: PRT
<213> ORGANISM: artificial
<220> FEATURE:
<223> OTHER INFORMATION: 10 aa hBD3 derived peptide (C terminus), C
      replaced with W

<400> SEQUENCE: 38

Arg Gly Arg Lys Trp Trp Arg Arg Lys Lys
1               5                   10

<210> SEQ ID NO 39
<211> LENGTH: 10
<212> TYPE: PRT
<213> ORGANISM: artificial
<220> FEATURE:
<223> OTHER INFORMATION: 10 aa hBD3 derived peptide (C terminus), C
      replaced with F

<400> SEQUENCE: 39

Arg Gly Arg Lys Phe Phe Arg Arg Lys Lys
1               5                   10

<210> SEQ ID NO 40
<211> LENGTH: 10
<212> TYPE: PRT
<213> ORGANISM: artificial
<220> FEATURE:
<223> OTHER INFORMATION: 10 aa hBD3 derived peptide (C terminus), C
      replaced with Y

<400> SEQUENCE: 40

Arg Gly Arg Lys Tyr Tyr Arg Arg Lys Lys
1               5                   10

<210> SEQ ID NO 41
<211> LENGTH: 10
<212> TYPE: PRT
<213> ORGANISM: artificial
<220> FEATURE:
<223> OTHER INFORMATION: 10 aa hBD3 derived peptide (C terminus), C
      replaced with L

<400> SEQUENCE: 41

Arg Gly Arg Lys Leu Leu Arg Arg Lys Lys
1               5                   10

<210> SEQ ID NO 42
<211> LENGTH: 10
<212> TYPE: PRT
<213> ORGANISM: artificial
<220> FEATURE:
<223> OTHER INFORMATION: 10 aa hBD3 derived peptide (C terminus), C
      replaced with I

<400> SEQUENCE: 42

Arg Gly Arg Lys Ile Ile Arg Arg Lys Lys
1               5                   10

<210> SEQ ID NO 43
```

```
<211> LENGTH: 10
<212> TYPE: PRT
<213> ORGANISM: artificial
<220> FEATURE:
<223> OTHER INFORMATION: 10 aa hBD3 derived peptide (C terminus), C
      replaced with V

<400> SEQUENCE: 43

Arg Gly Arg Lys Val Val Arg Arg Lys Lys
1               5                   10

<210> SEQ ID NO 44
<211> LENGTH: 10
<212> TYPE: PRT
<213> ORGANISM: artificial
<220> FEATURE:
<223> OTHER INFORMATION: 10 aa hBD3 derived peptide (C terminus), C
      replaced with H

<400> SEQUENCE: 44

Arg Gly Arg Lys His His Arg Arg Lys Lys
1               5                   10

<210> SEQ ID NO 45
<211> LENGTH: 10
<212> TYPE: PRT
<213> ORGANISM: artificial
<220> FEATURE:
<223> OTHER INFORMATION: 10 aa hBD3 derived peptide (C terminus), C
      replaced with C(Acm)
<220> FEATURE:
<221> NAME/KEY: MISC_FEATURE
<222> LOCATION: (5)..(6)
<223> OTHER INFORMATION: Xaa is C(Acm)

<400> SEQUENCE: 45

Arg Gly Arg Lys Xaa Xaa Arg Arg Lys Lys
1               5                   10
```

ANTIMICROBIAL PEPTIDES

FIELD OF THE INVENTION

The present invention relates to antimicrobial peptide(s). In particular, the invention relates to analogs of hBD3, their derivatives or fragments thereof.

BACKGROUND OF THE INVENTION

Defensins are small 3-5 kDa cationic endogenous proteins constrained by three disulfide bonds and are primarily known for their antimicrobial activity (Raj P. A. and A. R. Dentino, 2002). Defensins have been shown to be key elements in the innate immune system of many organisms, the first line of defense against invading pathogens. They also act as chemoattractant agents for monocytes and dendritic cells in mammals (Yang et al, 2001). In humans, there are currently six α-defensins, human neutrophil peptides (hNP1 to hNP6) and four β-defensins (hBD1 to hBD4).

As a class of peptides, defensins have broad anti-microbial activity against Gram-negative and Gram-positive bacteria, yeast, and some enveloped viruses including HIV, although specific defensins often have defined spectra of activity (Schroder J. M., 1999). hBD3 has a broad spectrum antimicrobial activity against gram-negative and gram-positive bacteria, fungi, and adenovirus with hBD3 consistently being the most potent. Additionally, hBD3 has significant bactericidal activity against multi-drug-resistant *Staphylococcus aureus* at physiological salt concentrations (David et al, 2002), and has shown activity against vancomycin-resistant *Enterococcus faecium, Burkholderia cepacia* and the yeast *Candida albicans* (Harder et al, 2001; Garcia et al, 2001).

It is generally assumed that the antimicrobial activity of defensins is determined by the existence of an amphiphilic molecular structure and the extent and distribution of cationic and hydrophobic regions on the folded peptide surface (Yeaman and Yount, 2003; Hwang and Vogel, 1998). The presence and the position of disulfide bridges and N-terminal sequence variations/fragments seem to have a marginal influence on the antibacterial effect of β-defensins (Zucht et al, 1998). Only little is known about the influence of structural factors of β-defensins on the interaction with eukaryotic membranes.

Selectivity of effects of antibacterial peptides including β-defensins on bacterial and eukaryotic cells may be determined by the balance of positively charged and hydrophobic surface regions. Disulfide bonds in hBD3, although required for binding and activation of chemokine receptor CCR6 for chemotaxis, appear to be dispensable for its antibacterial function, and a linear structure of [Abu]-hBD3 appears to have abolished the chemotactic activity of hBD3, but the bacterial activity remained unaffected in the absence of any disulfide bond. Despite the significant progress in recent years, the structure-activity relationships for human defensins remain largely unexplored. The sequence rules and structural determinants in human defensins that govern a great variety of biological functions and mechanisms of their action continue to remain poorly understood.

Gordon, Y. Jerold, et al (in Current Eye Research, 2005, 30, 505-15) commented that, among disadvantages, systemic and local toxicity and high manufacturing costs are two major disadvantages for development of antimicrobial peptides as anti-infective drugs. Efforts to develop better defensins have yielded some results suggesting that it is feasible to increase the killing ability, but host cytotoxicity may also increase under these circumstances Accordingly, cytotoxicity may be considered a major challenge for ophthalmic development.

Accordingly, there is a need in this field of technology of further investigation and development of effective, improved and less cytotoxic products.

SUMMARY OF THE INVENTION

The present invention seeks to address the problems above. In particular, the invention provides an isolated antimicrobial peptide and uses thereof.

According to a first aspect, the present invention provides an isolated antimicrobial peptide, wherein the peptide is a linear analog of hBD3 or a fragment thereof, provided that the analog is not SEQ ID NO:28 and the fragment is not any one of SEQ ID NOs:31 to 36.

Any one of the cysteine residues of hBD3 may be replaced with any other amino acid or a derivative thereof, or may be replaced with a protected cysteine residue or derivative thereof, or the cysteine residue may be deleted. The isolated peptide may comprise the amino acid sequence of any one of SEQ ID NOs:2 to 12 or a fragment thereof, wherein any one of $X^1$, $X^2$, $X^3$, $X^4$, $X^5$ and $X^6$ is: any amino acid except cysteine; a protected cysteine residue or derivative thereof except C[Abu]; or the amino acid is not present.

According to a second aspect, the present invention provides an isolated antimicrobial peptide, wherein the peptide is a linear analog of hBD3 or a fragment thereof and comprises the amino acid sequence of any one of: SEQ ID NOs:2 to 12 or a fragment thereof, wherein any one of $X^1$, $X^2$, $X^3$, $X^4$, $X^5$ and $X^6$ is: any amino acid except cysteine; a protected cysteine residue or derivative thereof except C[Abu]; or the amino acid is not present The isolated peptide according to any aspect of the present invention may comprise the amino acid sequence of any one of SEQ ID NOs:13 to 25, or a fragment thereof. In particular, the isolated peptide comprises the amino acid sequence of any one of SEQ ID NOs:13 to 18, or a fragment thereof. The protected cysteine residue may be any one of C(Acm), C(But), C(t-Buthio), C(Bzl), C(4-Me-Bzl), C(4-MeO-Bzl), C(Mmt) or C(Cam). The isolated peptide may also comprises the amino acid sequence of any one of: SEQ ID NOs: 39 to 45 or a fragment thereof.

The isolated peptide may have reduced cytotoxicity to at least one cell of any cell type compared to the wild type hBD3.

The present invention also provides an isolated polynucleotide, wherein the polynucleotide encodes at least one peptide or fragment thereof according to any aspect of the present invention. The polynucleotide may be comprised in a vector. Accordingly, the present invention also provides a vector comprising a polynucleotide according to any aspect.

Another aspect of the present invention is a host cell comprising a polynucleotide according to any aspect of the invention, or a host cell comprising a vector as provided by any aspect of the invention.

The present invention also provides a pharmaceutical composition comprising at least one antimicrobial peptide or fragment thereof according to any aspect of the present invention. The pharmaceutical composition may be formulated for topical, oral or parental administration. In particular, the pharmaceutical composition is formulated for administration by injection, inhalation and/or topical application.

The pharmaceutical composition may be an antimicrobial composition. Accordingly, the present invention provides an antimicrobial composition comprising at least one peptide or fragment thereof according to any aspect of the invention and at least one non-peptide antimicrobial agent.

The composition according to any aspect of the present invention may be for topical administration and may also be suitable for treatment of skin and/or mucous membrane(s). The composition may be in the form eye drop(s) composition or solution.

The present invention also provides a contact lens solution comprising at least one pharmaceutical composition according to any aspect of the present invention, at least one antimicrobial composition according to any aspect of the invention or at least one peptide and/or fragment thereof according to any aspect of the invention.

Another aspect of the present invention is a contact lens comprising at least one polymer and at least one peptide, at least one pharmaceutical composition, and/or at least one antimicrobial composition, each as described herein.

The present invention further provides a device coating, wherein the coating comprises at least one pharmaceutical composition, at least one antimicrobial composition, and/or at least one peptide or fragment thereof, each as described herein. The device coating may be a medical device coating. Also provided by the present invention is a device coated with at least one coating as described herein. The device may be but is not limited to a catheter, a needle, a sheath, a stent, a contact lens and/or a dressing.

According to another aspect, the present invention provides a kit comprising at least one antimicrobial peptide, at least one pharmaceutical composition, and/or at least one antimicrobial composition, each described herein, disposed in at lease one suitable container. The kit may further comprise at least one additional antimicrobial agent.

The present invention also provides a method of inhibiting and/or reducing the growth of at least one microorganism comprising contacting the microorganism with at least one antimicrobial peptide according to any aspect of the invention, at least one pharmaceutical composition according to any aspect of the invention, and/or at least one antimicrobial composition according to any aspect of the invention.

There is also provided a method of inhibiting and/or reducing the growth in a host of at least one microorganism, the method comprising administering to or applying onto the host at least one antimicrobial peptide at least one pharmaceutical composition, and/or at least one antimicrobial composition, according to any aspect of the invention.

The present invention also provides a method of treating at least one microbial infection comprising administering to a subject at least one antimicrobial peptide, at least one pharmaceutical composition, and/or at least one antimicrobial composition, according to any aspect of the invention.

Another aspect of the present invention is a method of treating at least one multi-drug resistant microorganism comprising treating the microorganism with at least one antimicrobial peptide, at least one pharmaceutical composition, and/or at least one antimicrobial composition, according to any aspect of the invention.

Accordingly, the microorganism in any one of the methods described may be *B. pseudomallei, Staphylococcus aureus, Escherichia coli, Pseudomonas aeruginosa, Bacillus cereus*, a virus and/or a fungus.

The present invention also provides a drug screening method comprising administering at least one analog of hBD3 or a fragment thereof to at least one cell of any cell type, and determining whether the analog or fragment thereof has reduced cytotoxicity to the cell of any cell type compared to the wild type hBD3.

Another aspect of the present invention is a method of designing a peptide analog or fragment thereof comprising deleting any residue of cysteine, replacing any residue of cysteine with any other amino acid or a derivative thereof or with a protected cysteine residue or derivative thereof, administering to a cell, and determining a reduced cytotoxicity.

BRIEF DESCRIPTION OF THE FIGURES

FIG. 8A. UV chromatogram of purified W6 on C18 (150 mm×3.9 mm, 5 μm, 100 Å), flow rate 0.2 ml/min; gradient 18-38% of eluant B in 32 min.

FIG. 8B. SIR chromatogram at m/z=1132.9 ($[M+5H]^{5+}$) in ESI-MS analysis of purified W6 on C18 (150 mm×3.9 mm, 5 μm, 100 Å), flow rate 0.2 ml/min; gradient 18-38% of eluant B in 32 min.

FIG. 8C. ESI-MS analysis of purified W6 on C18 (150 mm×3.9 mm, 5 μm, 100 Å), flow rate 0.2 ml/min; gradient 18-38% of eluant B in 32 min FIG. 8D. Deconvoluted MS spectrum in ESI-MS analysis of purified W6 on C18 (150 mm×3.9 mm, 5 μm, 100 Å), flow rate 0.2 ml/min; gradient 18-38% of eluant B in 32 min.

FIG. 9A. UV chromatogram of purified F6 on C18 (150 mm×3.9 mm, 5 μm, 100 Å), flow rate 0.2 ml/min; gradient 18-38% of eluant B in 32 min.

FIG. 9B. SIR chromatogram at m/z=1086 ($[M+5H]^{5+}$) in ESI-MS analysis of purified F6 on C18 (150 mm×3.9 mm, 5 μm, 100 Å), flow rate 0.2 ml/min; gradient 18-38% of eluant B in 32 min.

FIG. 9C. ESI-MS analysis of purified F6 on C18 (150 mm×3.9 mm, 5 μm, 100 Å), flow rate 0.2 ml/min; gradient 18-38% of eluant B in 32 min.

FIG. 9D. Deconvoluted MS spectrum in ESI-MS analysis of purified F6 on C18 (150 mm×3.9 mm, 5 μm, 100 Å), flow rate 0.2 ml/min; gradient 18-38% of eluant B in 32 min.

FIG. 10A. UV chromatogram of purified Y6 on C18 (150 mm×3.9 mm, 5 μm, 100 Å), flow rate 0.2 ml/min; gradient 18-38% of eluant B in 32 min.

FIG. 10B. SIR chromatogram at m/z=1105.3 ($[M+5H]^{5+}$) in ESI-MS analysis of purified Y6 on C18 (150 mm×3.9 mm, 5 μm, 100 Å), flow rate 0.2 ml/min; gradient 18-38% of eluant B in 32 min.

FIG. 10C. ESI-MS analysis of purified Y6 on C18 (150 mm×3.9 mm, 5 μm, 100 Å), flow rate 0.2 ml/min; gradient 18-38% of eluant B in 32 min.

FIG. 10D. Deconvoluted MS spectrum in ESI-MS analysis of purified Y6 on C18 (150 mm×3.9 mm, 5 μm, 100 Å), flow rate 0.2 ml/min; gradient 18-38% of eluant B in 32 min.

FIG. 11A. UV chromatogram of purified A6 on C18 (150 mm×3.9 mm, 5 μm, 100 Å), flow rate 0.2 ml/min; gradient 18-38% of eluant B in 32 min.

FIG. 11B. SIR chromatogram at m/z=994.8 ([M+5H]$^{5+}$) in ESI-MS analysis of purified A6 on C18 (150 mm×3.9 mm, 5 μm, 100 Å), flow rate 0.2 ml/min; gradient 18-38% of eluant B in 32 min.

FIG. 11C. ESI-MS analysis of purified A6 on C18 (150 mm×3.9 mm, 5 μm, 100 Å), flow rate 0.2 ml/min; gradient 18-38% of eluant B in 32 min.

FIG. 11D. Deconvoluted MS spectrum in ESI-MS analysis of purified A6 on C18 (150 mm×3.9 mm, 5 μm, 100 Å), flow rate 0.2 ml/min; gradient 18-38% of eluant B in 32 min.

FIG. 12A. UV chromatogram of purified S6 on C18 (150 mm×3.9 mm, 5 μm, 100 Å), flow rate 0.2 ml/min; gradient 18-38% of eluant B in 32 min.

FIG. 12B. SIR chromatogram at m/z=845.1 ([M+6H]$^{6+}$) in ESI-MS analysis of purified S6 on C18 (150 mm×3.9 mm, 5 μm, 100 Å), flow rate 0.2 ml/min; gradient 18-38% of eluant B in 32 min.

FIG. 12C. ESI-MS analysis of purified S6 on C18 (150 mm×3.9 mm, 5 μm, 100 Å), flow rate 0.2 ml/min; gradient 18-38% of eluant B in 32 min.

FIG. 12D. Deconvoluted MS spectrum in ESI-MS analysis of purified S6 on C18 (150 mm×3.9 mm, 5 μm, 100 Å), flow rate 0.2 ml/min; gradient 18-38% of eluant B in 32 min.

FIG. 13A. UV chromatogram of purified C6 on C18 (150 mm×3.9 mm, 5 μm, 100 Å), flow rate 0.2 ml/min; gradient 18-38% of eluant B in 32 min.

FIG. 13B. SIR chromatogram at m/z=799.3 ([M+7H]$^{7+}$) in ESI-MS analysis of purified C6 on C18 (150 mm×3.9 mm, 5 μm, 100 Å), flow rate 0.2 ml/min; gradient 18-38% of eluant B in 32 min.

FIG. 13C. ESI-MS analysis of purified C6 on C18 (150 mm×3.9 mm, 5 μm, 100 Å), flow rate 0.2 ml/min; gradient 18-38% of eluant B in 32 min.

FIG. 13D. Deconvoluted MS spectrum in ESI-MS analysis of purified C6 on C18 (150 mm×3.9 mm, 5 μm, 100 Å), flow rate 0.2 ml/min; gradient 18-38% of eluant B in 32 min.

FIG. 14 Comparison of overall molecular hydrophobicity of C-Terminus fragment peptides of hBD3 in terms of retention time of SIR chromatogram of charged fragments of peptides FIG. 15 Cytotoxicity of C-Terminus peptides vs concentration

LIST OF SEQUENCES

Sequences Disclosed in the Prior Art

Figure 1:
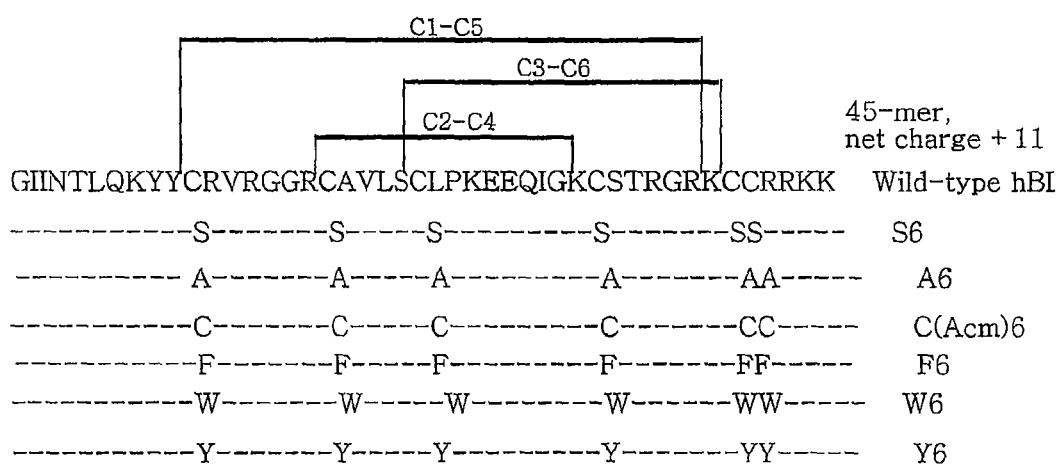
FIG. 1 shows new analogs of human β-defensin 3 not previously reported: W6, F6, Y6, S6, A6 and C(Acm)6.

```
Wild type hBD3:
                                              SEQ ID NO: 1
GIINTLQKYYCRVRGGRCAVLSCLPKEEQIGKCSTRGRKCCRRKK (Wu et al., 2003) C(Acm)1-5
                                              SEQ ID NO: 26
GIINTLQKYYC(Acm)RVRGGRCAVLSCLPKEEQIGKC(Acm)STRGRKC(Acm)
CRRKK (Wu et al., 2003) C(Acm)1-6
                                              SEQ ID NO: 27
GIINTLQKYYC(Acm)RVRGGRCAVLSCLPKEEQIGKCSTRGRKCC
(Acm)RRKK
```

-continued
```
(Wu et al., 2003) [Abu]-BD3
                                              SEQ ID NO: 28
GIINTLQKYYC[Abu]RVRGGRC[Abu]AVLSC[Abu]LPKEEQIGKC
[Abu]STRGRKC[Abu]C[Abu]RRKK (Hoover et al., 2003) hBD3delta8
                                              SEQ ID NO: 29
KYYCRVRGGRCAVLSCLPKEEQIGKCSTRGRKCCRRKK (Hoover et al., 2003) hBD3delta10
                                              SEQ ID NO: 30
YCRVRGGRCAVLSCLPKEEQIGKCSTRGRKCCRRKK (Hoover et al., 2003)
                                              SEQ ID NO: 31
KEEQIGKSSTRGRKSSRRKK (Hoover et al., 2003)
                                              SEQ ID NO: 32
KSSTRGRKSSRRKK (Hoover et al., 2003)
                                              SEQ ID NO: 33
RGRKSSRRKK (Hoover et al., 2003)
                                              SEQ ID NO: 34
RGRKSSRRK (Hoover et al., 2003)
                                              SEQ ID NO: 35
KYYSRVRGGRSAVLSSLPK (Hoover et al., 2003)
                                              SEQ ID NO: 36
GIINTLQKYYSRVRGGR
```

Sequences According to the Present Invention

```
SEQ ID NO: 2:
GIINTLQKYYX¹RVRGGRX²AVLSX³LPKEEQIGKX⁴STRGRKX⁵X⁶RR
KK
```

Any one of $X^1$, $X^2$, $X^3$, $X^4$, $X^5$ and $X^6$ is: any amino acid except cysteine; a protected cysteine residue or derivative thereof except C[Abu]; or the amino acid is not present. The same meaning of $X^n$ applies to the followings sequences.

```
                                              SEQ ID NO: 3
KYYX¹RVRGGRX²AVLSX³LPKEEQIGKX⁴STRGRKX⁵X⁶RRKK

SEQ ID NO: 4
YX¹RVRGGRX²AVLSX³LPKEEQIGKX⁴STRGRKX⁵X⁶RRKK

SEQ ID NO: 5
LQKYYX¹RVRGGRX²AVLSX³LPKEEQIGKX⁴STRGRKX⁵X⁶RRKK

SEQ ID NO: 6
RX²AVLSX³LPKEEQIGKX⁴STRGRKX⁵X⁶RRKK

SEQ ID NO: 7
KEEQIGKX⁴STRGRKX⁵X⁶RRKK

SEQ ID NO: 8
KX⁴STRGRKX⁵X⁶RRKK

SEQ ID NO: 9
RGRKX⁵X⁶RRKK

SEQ ID NO: 10
RGRKX⁵X⁶RRK

SEQ ID NO: 11
KYYX¹RVRGGRX²AVLSX³LPK
```

```
                                           SEQ ID NO: 12
GIINTLQKYYX¹RVRGGR

W6:
                                           SEQ ID NO: 13
GIINTLQKYYWRVRGGRWAVLSWLPKEEQIGKWSTRGRKWWRRKK

F6:
                                           SEQ ID NO: 14
GIINTLQKYYFRVRGGRFAVLSFLPKEEQIGKFSTRGRKFFRRKK

Y6:
                                           SEQ ID NO: 15
GIINTLQKYYYRVRGGRYAVLSYLPKEEQIGKYSTRGRKYYRRKK

S6:
                                           SEQ ID NO: 16
GIINTLQKYYSRVRGGRSAVLSSLPKEEQIGKSSTRGRKSSRRKK

A6:
                                           SEQ ID NO: 17
GIINTLQKYYARVRGGRAAVLSALPKEEQIGKASTRGRKAARRKK

C(Acm)6:
                                           EQ ID NO: 18
GIINTLQKYY C(Acm)6RVRGGR C(Acm)6AVLS C(Acm)6LPKEEQ
IGK C(Acm)6STRGRK C(Acm)6C(Acm)6RRKK

C(But)6:
                                           SEQ ID NO: 19
GIINTLQKYY C(But)6RVRGGR C(But)6AVLS C(But)6LPKEEQ
IGK C(But)6STRGRK C(But)6C(But)6RRKK

C(t-Buthio)6:
                                           SEQ ID NO: 20
GIINTLQKYY C(t-Buthio)6RVRGGR C(t-Buthio)6AVLS C
(t-Buthio)6LPKEEQIGK C(t-Buthio)6STRGRK C(t-
Buthio)6C(t-Buthio)6RRKK C(BzI)6:
                                           SEQ ID NO: 21
GIINTLQKYY C(BzI)6RVRGGR C(BzI)6AVLS C(BzI)6LPKEEQ
IGK C(BzI)6STRGRK C(BzI)6C(BzI)6RRKK C(4-MeBzI)6:
                                           SEQ ID NO: 22
GIINTLQKYY C(4-MeBzI)6RVRGGR C(4-MeBzI)6AVLS C(4-
MeBzI)6LPKEEQIGK C(4-MeBzI)6STRGRK C(4-MeBzI)6C(4-
MeBzI)6RRKK C(4-MeO-BzI)6:
                                           SEQ ID NO: 23
GIINTLQKYY C(4-MeO-BzI)6RVRGGR C(4-MeO-BzI)6AVLS C
(4-MeO-BzI)6LPKEEQIGK C(4-MeO-BzI)6STRGRK C(4-MeO-
BzI)6C(4-MeO-BzI)6RRKK C(Mmt)6:
                                           SEQ ID NO: 24
GIINTLQKYY C(Mmt)6RVRGGR C(Mmt)6AVLS C(Mmt)6LPKEEQ
IGK C(Mmt)6STRGRK C(Mmt)60(Mmt)6RRKK C(Cam)6:
                                           SEQ ID NO: 25
GIINTLQKYY C(Cam)6RVRGGR C(Cam)6AVLS C(Cam)6LPKEEQ
IGK C(Cam)6STRGRK C(Cam)6C(Cam)6RRKK WT C-terminus:
                                           SEQ ID NO: 37
RGRKCCRRKK

W2:
                                           SEQ ID NO: 38
RGRKWWRRKK

F2:
                                           SEQ ID NO: 39
RGRKFFRRKK

Y2:
                                           SEQ ID NO: 40
RGRKYYRRKK

L2:
                                           SEQ ID NO: 41
RGRKLLRRKK

I2:
                                           SEQ ID NO: 42
RGRKIIRRKK

V2:
                                           SEQ ID NO: 43
RGRKVVRRKK

H2:
                                           SEQ ID NO: 44
RGRKHHRRKK

C2 or C(Acm)2:
                                           SEQ ID NO: 45
RGRKC(Acm)C(Acm)RRKK
```

DETAILED DESCRIPTION OF THE INVENTION

Bibliographic references mentioned in the present specification are for convenience listed in the form of a list of references and added at the end of the examples. The whole content of such bibliographic references is herein incorporated by reference.

In the present invention, a series of linear analogs of hBD3 were designed, and synthesised, and the influence of the overall hydrophobicity, charge distribution/density, the ratio of the positively charged surface regions to hydrophobic ones on the antibacterial activity, cytotoxicity and hemolytic activity were investigated. It was found that the linear backbone structure of hBD3 analogs with different overall hydrophobicity in presence of any disulfide bridge is a key structural determinant to decrease cytotoxicity to mammalian cells, particularly epithelial cells. This provided defensin derivative antibiotics with increased bactericidal activity and with reduced mammalian cell cytotoxicity. The present invention therefore relates to an isolated antimicrobial peptide.

According to a first aspect, the present invention provides an isolated antimicrobial peptide, wherein the peptide is a linear analog of hBD3 or a fragment thereof, provided that the analog is not SEQ ID NO:28 and the fragment is not any one of SEQ ID NOs:31 to 36.

"Peptide" as used herein refers to and encompasses any amino acid molecule, a peptide or polypeptide. The "peptide" can be obtained as a gene product, a purified and/or isolated product, an expression product, from fragmentation of protein(s) or a synthetic peptide. An "isolated peptide" encompasses naturally occurring, a gene expression product and a synthetic peptide. Peptide Production—peptide of the invention may be produced by any method known in the art. One method of producing the disclosed peptides is to link two or more amino acid residues together by protein chemistry techniques. For example, peptides are chemically synthesized using currently available laboratory equipment using either Fmoc (9-fluorenylmethyloxycarbonyl) or Boc (tert-butyloxycarbonoyl) chemistry (Applied Biosystems, Inc., Foster City, Calif.). A peptide can be synthesized and not cleaved from its synthesis resin, whereas the other fragment of a peptide or protein can be synthesized and subsequently cleaved from the resin, thereby exposing a terminal group, which is functionally blocked on the other fragment. By peptide condensation reactions, these two fragments can be covalently joined via a peptide bond at their carboxyl and amino termini, respectively, (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY). Alternatively, the peptide is independently synthesized in vivo. Once isolated, these independent peptides may be linked to form a peptide or fragment thereof via similar peptide condensation reactions.

It is contemplated that specific modifications may be made within the peptide that maintain the peptides antimicrobial properties of the claimed sequence, but also confers some additional desirable property to the peptide. It is well known in the art that certain amino acids may be substituted for other amino acids in a protein structure without appreciable loss of peptide activity. Since it is the interactive capacity and nature of a peptide that defines that peptide's biological functional activity, certain amino acid sequence substitutions can be made in a sequence and nevertheless obtain a peptide with like properties. It is thus contemplated by the inventors that various changes may be made in the sequence of the isolated antimicrobial peptide, without appreciable loss of biological activity and perhaps may enhance desired activities.

The amino acid abbreviations used herein are conventional one letter codes for the amino acids and are expressed as follows: A or Ala, alanine; B, asparagine or aspartic acid; C or Cys, cysteine; D or Asp, aspartic acid; E or Glu, glutamic acid; F or Phe, phenylalanine; G or Gly, glycine; H or His, histidine; I or Ile, isoleucine; K or Lys, lysine; L or Leu, leucine; M or Met, methionine; N or Asn, asparagine; P or Pro, proline; Q or Gln, glutamine; R or Arg, arginine; S or Ser, serine; T or Thr, threonine; V or Val, valine; W or Trp, tryptophan; Y or Tyr, tyrosine; Z, glutamine or glutamic acid.

For example, in designing peptide constructs with antimicrobial properties, substitutions may be used which modulate one or more properties of the molecule. Such variants typically contain the exchange of one amino acid for another at one or more sites within the peptide. For example, certain amino acids may be substituted for other amino acids in a peptide structure in order to enhance the interactive binding capacity of the structures. Since it is the interactive capacity and nature of a protein that defines a protein's biological functional activity, certain amino acid substitutions can be made in a protein sequence, and its underlying DNA coding sequence which potentially create a peptide with superior characteristics. Accordingly, a particular aspect of the present invention provides that the cysteine residues of hBD3 may be replaced with any other amino acid (as listed above) or a derivative thereof, or may be replaced with a protected cysteine residue or derivative thereof, or the cysteine residue may be deleted. As amino acid derivative and/or protection group, any derivative listed in Table G-2 of the User's Manual for Patentin 3.1 may be used. However, the type of amino acid derivative and/or protection group is not limited to such list.

Examples of protected cysteine residues suitable for the present invention include, but are not limited to, C(Acm), C(But), C(t-Buthio), C(Bzl), C(4-Me-Bzl), C(4-MeO-Bzl), C(Mmt) and C(Cam). Accordingly, any suitable protected cysteine residue may be used in the present invention.

The isolated peptide may comprise the amino acid sequence of any one of: SEQ ID NOs:2 to 12, or a fragment thereof, wherein any one of $X^1$, $X^2$, $X^3$, $X^4$, $X^5$ and $X^6$ is: any amino acid except cysteine; a protected cysteine residue or derivative thereof except C[Abu]; or the amino acid is not present. The isolated peptide may comprise the amino acid sequence of any one of SEQ ID NOs: 13 to 25, or a fragment thereof. In particular, the isolated peptide comprises the amino acid sequence of any one of SEQ ID NOs: 13 to 18, or a fragment thereof. Specific examples of hBD3 linear analogs according to the present invention are shown in FIG. 1.

The present invention also provides an isolated antimicrobial peptide, wherein the peptide is a linear analog of hBD3 or a fragment thereof, and comprises the amino acid sequence of any one of: SEQ ID NOs: 2 to 12 or a fragment thereof, wherein any one of $X^1$, $X^2$, $X^3$, $X^4$, $X^5$ and $X^6$ is: any amino acid except cysteine; a protected cysteine residue or derivative thereof except C[Abu]; or the amino acid is not present. The isolated peptide may comprise the amino acid sequence of any one of SEQ ID NOs: 13 to 25. According to a preferred aspect, the six cysteine residues in hBD3 were uniformly replaced by six residues with different polarity, e.g., F, W, Y, C(Acm), A and S, to form corresponding linear analogs of hBD3 [coded as F6, W6, Y6, C(Acm)6, A6 and S6] with different overall hydrophobicity Accordingly, the present invention provides at least one isolated linear peptide comprising the amino acid sequence of any one of SEQ ID NOs: 13 to 18, or a fragment thereof. However, fragments and peptide comprising the amino acid sequence of SEQ ID NOs: 26-36 are excluded from the scope of protection of the present invention.

It is further provided that the isolated peptide according to any aspect of the present invention has a reduced cytotoxicity to at least one cell of any cell type compared to the wild type hBD3.

According to another aspect of the present invention, an isolated polynucleotide is provided, wherein the polynucleotide encodes at least one peptide according to any aspect of the invention, or fragment thereof.

Polynucleotide, as used herein, refers to cDNA, DNA, mRNA or RNA of genomic or synthetic origin which may be single- or double-stranded. Single-stranded DNA or RNA may be the coding strand, also known as the sense strand, or it may be the non-coding strand, also referred to as the antisense strand. Polynucleotide also includes nucleic acid molecules. Isolated polynucleotide refers to a nucleic acid molecule, DNA or RNA, which has been removed from its natural environment.

The antimicrobial peptides of the present invention may be expressed by a prokaryotic or eukaryotic expression vector. The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism.

Additionally, the present invention also provides a vector comprising the polynucleotide or the nucleic acid encoding any one or more of the peptides described herein. In certain embodiments, the invention provides a vector comprising a nucleic acid encoding at least one of the peptides of the present invention. The vector can be a viral vector, a plasmid vector, a cosmid vector, an adenoviral vector, a phage vector, a retroviral vector, an adeno-associated viral (AAV) vector, or any other vector capable of including a nucleic acid encoding a peptide of the invention, which would be known to a skilled person. The vector can be an expression vector that is intended and capable of integrating into a cell genome. Useful vectors and their construction are disclosed in Sambrook and Russel, (2001) Molecular Cloning: A Laboratory Manual, Cold Spring Harbor Laboratory Press, US.

The invention also provides a host cell comprising the polynucleotide, polypeptide, peptide, and/or the vector of the invention. Such a host cell may be a eukaryotic cell or a prokaryotic cell. In the case of eukaryotic cells, retrovirus or adenovirus based vectors can be used to put the polynucleotide of the invention into the host cell. Methods known to one with skill in the art to insert the nucleic acids or polypeptides in host cells are encompassed within this invention. The following are non-limiting examples of such methods: naked DNA transfection, lipofectin-mediated transfer, transformation, micro-injection of nucleic acid into a cell, or calcium-phosphate precipitation transfection methods. Host cells can be obtained from commercial sources such as the American Type Culture Collection (ATCC), 10801 University Boulevard, Manassas, Va. 20110-2209.

Host cells can be grown in liquid media culture or on tissue culture plates. The growth conditions will be dependent upon the specific host cells used and such conditions would be known to one with skill in the art. Transfection and growth of host cells is described in Sambrook and Russel, id. The invention provides for a recombinant cell expressing a nucleic acid encoding the polypeptide of the claimed invention. The invention also provides for a recombinant cell producing the polypeptide of the invention.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

Another aspect of the present invention is a pharmaceutical composition comprising at least one antimicrobial peptide or fragment thereof as described herein. The present invention also provides an anti-microbial composition comprising at least one antimicrobial peptide according to any aspect of the present invention, or a fragment thereof, and at least one non-peptide antimicrobial agent.

The composition may further comprise a pharmaceutically or pharmacologically acceptable carrier. The phrases "pharmaceutically or pharmacologically acceptable" refer to molecular entities and compositions that do not produce an adverse, allergic or other untoward reaction when administered to an animal, or a human, as appropriate. The compositions of the present invention may be an aqueous composition, comprising an effective amount of the antimicrobial peptide, dissolved or dispersed in a pharmaceutically acceptable carrier or aqueous medium.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

Where the antimicrobial peptide is to be provided to a subject, the nature of the peptides facilitates a number of alternate routes of administration. The durability of the peptides facilitates not only internal administration but also application in a topical formulation. Where the peptides are to be given internally, a variety of means of delivery are possible. For example, the peptides are diluted in a suitable composition for delivery by inhalation for the treatment or prevention of infections. It is further contemplated that the nucleic acid sequence of the peptides may be delivered to cells by an appropriate vector or DNA delivery vehicle in the context of gene therapy.

Accordingly, the pharmaceutical composition or antimicrobial composition of the present invention may be formulated for topical, oral or parental administration. For example, the compositions may be formulated for administration by injection or for administration by inhalation. The active compounds will generally be formulated for parenteral administration, e.g., formulated for injection via the intravenous, intramuscular, sub-cutaneous, intralesional, topical and/or even intraperitoneal routes. The preparation of an aqueous composition that contains the antimicrobial peptide as an active component or ingredient will be known to those of skill in the art in light of the present disclosure. Typically, such compositions may be prepared as injectables, either as liquid solutions or suspensions; solid forms suitable for using to prepare solutions or suspensions upon the addition of a liquid prior to injection can also be prepared; and the preparations can also be emulsified. Topical application for mucosal surfaces such as the eye and mouth can be prepared in liquid solutions or suspensions.

Examples of pharmaceutical compositions or antimicrobial compositions of the present invention suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form should be sterile and should be fluid to the extent that easy syringeability exists. It should also be stable under the conditions of manufacture and storage and be able to be preserved against the contamination of microorganisms, such as bacteria and fungi. The pharmaceutical composition may also be in the form of salts.

The pharmaceutically acceptable carrier can also be a solvent or dispersion medium containing, for example, water, ethanol, polyol (for example, glycerol, propylene glycol, and liquid polyethylene glycol, and the like), suitable mixtures thereof, and vegetable oils.

The preparation of more, or highly, concentrated solutions for direct injection is also provided, where the use of DMSO as solvent may result in extremely rapid penetration, delivering high concentrations of the active compound of the pharmaceutical and antimicrobial composition to a small affected area.

In addition to forms of parenteral administration, such as intravenous or intramuscular injection, other acceptable forms of administering the pharmaceutical composition or the antimicrobial composition include, but not limited to: tablets or other solids for oral administration; liposomal formulations; time release capsules; and any other form currently used, including creams.

One may also use nasal solutions or sprays, aerosols or inhalants in the present invention. Nasal solutions are usually aqueous solutions designed to be administered to the nasal passages in drops or sprays. In addition, antimicrobial preservatives, similar to those used in ophthalmic preparations, and appropriate drug stabilizers, if required, may be included in the formulation.

Additional formulations which are suitable for other modes of administration include vaginal suppositories and pessaries. A rectal pessary or suppository may also be used. Suppositories are solid dosage forms of various weights and shapes, usually medicated, for insertion into the rectum, vagina or the urethra.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. For oral therapeutic administration, the active compounds of the pharmaceutical composition or antimicrobial composition may be incorporated with excipients and used in the form of ingestible tablets, buccal tables, troches, capsules, elixirs, suspensions, syrups, wafers, and the like.

In particular, the pharmaceutical composition or the antimicrobial composition according to any aspect of the present invention may be for topical administration and may be suitable for treatment of skin and/or mucous membrane(s). The pharmaceutical composition or the antimicrobial composition may also be in the form of eye drop(s) composition or solution.

The compositions of the present invention may be administered in a manner compatible with the dosage formulation and in such amount as is therapeutically effective. The formulations may be easily administered in a variety of dosage forms, such as injectable solutions, but any other suitable form may also be used, for example, drug release capsules.

The purified isolated antimicrobial peptides may be used without further modifications or may be diluted in a pharmaceutically acceptable carrier. As the peptides are stable, the peptides according to any aspect of the present invention, may be administered to humans or animals, included in food preparations, pharmaceutical preparations, medicinal and pharmaceutical products, cosmetic products, hygienic products, cleaning products and cleaning agents, as well as any material to which the peptides could be sprayed on or adhered to wherein the inhibition of microbial growth on such a material is desired.

The present invention also provides a contact lens solution comprising at least one pharmaceutical composition; at least one antimicrobial composition; and/or at least one peptide or fragment thereof, each as described above.

Additionally, the present invention provides a contact lens comprising at least one polymer and at least one peptide; at least one pharmaceutical composition; and/or at least one antimicrobial composition, each as described above.

While the invention encompasses administration of peptides to a subject for therapeutic or prophylactic benefit, it also is envisioned that the peptides will have other uses. However, the isolated peptides may also be included in antiseptic or antimicrobial preparations for application or introduction into environments in which one wishes to prevent or suppress microbial growth.

Accordingly, the present invention provides a mixture for application to a surface, such as a work surface or a surgical instrument, contact lens, a contact lens solution or devices used with contact lenses, for the prevention and/or suppression of microbial growth.

In particular, the present invention provides a device coating, wherein the coating comprises at least one pharmaceutical composition; at least one antimicrobial composition; or at least one peptide or fragment thereof, each as described above. The device coating may be a medical device coating.

The present invention also provides a device coated with at least one coating according to any aspect of the invention. The device may be a medical device. In the context of medical devices, the peptides of the present invention in their pure form or combined with other antimicrobial peptides or agents, could be sprayed on, coated on, or adhered to any surface of a medical device wherein the inhibition of microbial growth on such a surface is desired. Examples of such medical devices include, but are not limited to, an endotracheal tube, a catheter, a vascular catheter, an urinary catheter, a nephrostomy tube, a biliary stent, a peritoneal catheter, an epidural catheter, a central nervous system catheter, an orthopedic device, a prosthetic valve, a needle, a sheath, a stent and a medical implant.

The present invention also provides a kit comprising: at least one antimicrobial peptide; at least one pharmaceutical composition; and/or at least one antimicrobial composition, each as described above, disposed in at least one suitable container. The kit may further comprise at least one additional antimicrobial agent.

The antimicrobial peptides of the present invention may be used alone. However, they can also be used in adjunct therapy, in combination with another antimicrobial agent and/or antibiotic. In terms of killing or inhibiting a bacterium, one would contact the bacterium with an effective amount of an antibiotic in combination with an amount of an antimicrobial peptide effective to inhibit growth and/or proliferation in the bacterium. Accordingly, the present invention provides a method of inhibiting and/or reducing the growth of at least one microorganism comprising contacting the microorganism with: at least one antimicrobial peptide; at least one pharmaceutical composition; and/or at least one antimicrobial composition, each as described above.

The microorganism, e.g., bacterium, or population thereof, may be contacted either in vitro or in vivo. Contacting in vivo may be achieved by administering to a subject that has, or is suspected to have a microbial or bacterial infection, a therapeutically effective amount of pharmacologically acceptable antimicrobial peptide formulation alone or in combination with a therapeutic amount of a pharmacologically acceptable formulation of an antibiotic agent or other antimicrobial peptide. The invention may thus be employed to treat both systemic and localized microbial and bacterial infections by introducing the combination of agents into the general circulation or by applying the combination, e.g., topically to a specific site, such as a wound or burn, or to the eye, ear or other site of infection.

The present invention also provides a method of inhibiting and/or reducing the growth in a host of at least one microorganism comprising administering to or applying onto the host: at least one antimicrobial peptide; at least one pharmaceutical composition; and/or at least one antimicrobial composition, each as described above.

Also provided is a method of treating at least one microbial infection comprising administering to a subject: at least one antimicrobial peptide; at least one pharmaceutical composition; and/or at least one antimicrobial composition, each as described above. The present invention further provides a method of treating at least one multi-drug resistant microorganism comprising treating the microorganism with: at least one antimicrobial peptide; at least one pharmaceutical composition; and/or at least one antimicrobial composition, each as described above.

The term "microorganism" is used for simplicity and it will be easily understood that the invention is suitable for use against a population of microorganisms, i.e., "bacteria". In the context of bacterial or microbial infections, a person of ordinary skill would recognize the wide variety of potential pathogens. Examples of microorganisms include any one of the following, but are not limited to: *B. pseudomallei, Staphylococcus aureus, Escherichia coli, Pseudomonas aeruginosa* and *Bacillus cereus* as well as viruses and fungi.

The present invention also provides a drug screening method comprising administering at least one analog of hBD3 or a fragment thereof to at least one cell, and determining whether the analog or fragment thereof has reduced cytotoxicity to the cell compared to the wild type hBD3.

Another aspect of the present invention is a method of designing a peptide analog or fragment thereof comprising deleting any residue of cysteine, replacing any residue of cysteine with any other amino acid or a derivative thereof or with a protected cysteine residue or derivative thereof, administering to a cell, and determining a reduced cytotoxicity. The peptide may be at least one analog to hBD3. The design principle may be (but not limited to) the following: the decreased cytotoxicity to human cells can be controlled by the rational design of linear analogs of defensins peptides by molecular modeling and theory calculation in terms of overall hydrophobicity and charge density. Overall hydrophobicity is a basic physiochemical property of peptide as a result of folding in water. The overall hydrophobicity (the change of free energy, $\Delta G$, kcal/mol) was calculated based on the hydrophobicity scale of Wilmley and White. Greater hydrophobicity is represented by a more positive $\Delta G$. The overall hydrophobicity and charge density are associated with 3D structure of the peptides.

Having now generally described the invention, the same will be more readily understood through reference to the following examples which are provided by way of illustration, and are not intended to be limiting of the present invention.

Materials and Methods
Solid-Phase Peptide Synthesis (SPPS)

Fluorenylmethoxycarbonyl (Fmoc)-protected L-amino acids and resin were purchased from Advanced ChemTech (now advanced automated peptide protein TECHNOLOGIES, aappTEC) (KY, U.S.A.) and were used with the following side-chain protective groups: Arg (pbf)[1] or Arg(pmc), Lys(Boc), Tyr(But), Trp(Boc), Thr(But), Ser(But), Gln(Trt), Glu(OBut), Asn(Trt), Cys(Acm), and Fmoc-Lys(Boc)-Wang resin (substitution 0.72 mmol/g). Syntheses of six linear analogs of hBD3 were carried out on Apex 396 by Fmoc-chemistry. Acylation (coupling reaction) was carried out with HBTU-HOBT (HBTU is N-[1H-benzotriazol-1-yl)-(dimethylamino)methylene]-N-methylmethanaminium hexafluorophosphate N-oxide, and HOBT is N-hydroxybenzotriazole) in DMF (N,N-Dimethylformamide) at a synthesis scale of 0.04 mmol. Fmoc deprotection was carried out with 20% piperidine in DMF. The resulting peptidyl resins were treated with a freshly prepared mixture of trifluoroacetic acid (TFA)/triisopropylsilane (TIS)/phenol/Thionisole/water (90/1/2.5/5/1.5, the ratio of volume percent) for 2-3 h at room temperature. The crude peptides were precipitated by filtration into ice-cold diethyl ether, separated by centrifugation, washed three times with ice-cold ether and dried by automated evaporation of ether and other remaining/residual solvents in crude solid products in fume hood or dried under vacuum at room temperature. For further purification, the crude products were dissolved into mixture solvents of 5% CAN, 0.1% TFA in $H_2O$, and loaded onto a semi-preparative column (Waters, a Delta PAK C18, 300 mm×7.8 mm, 15 µm, 100 Å, flow rate 3 ml/min; eluant A, 0.01% TFA in DI water; eluant B, 0.01% TFA in CAN; gradient 20-35% of eluant B in 20 min; UV detection at 210 nm (Waters 2695 separations module with an auto-sampler and 996 photodiode array detector (PDA). Purified peptides were characterized by analytical HPLC-MS coupled system (Micromass Platform LCZ, Waters Associates using a Delta PAK C18, 150 mm×3.9 mm, 5 µm, 100 Å, flow rate 0.2 ml/min; gradient 18-38% of eluant B in 32 min. The molecular weight characterization by use of Mass Spectrometry of six linear analogs is provided in FIGS. 8-13.

Molecular Hydrophobicity

Molecular hydrophobicity of peptides was measured by HPLC-MS at the same experimental conditions, e.g., the same peptide concentration (500 or 100 µg/ml), loading (5 µl) and flow rate of 0.2 ml/min in the same gradient 18-38% of eluant A in 32 min and relatively compared in term of retention time (Rt) of product peak.

CD Spectroscopy

Figure 2A:
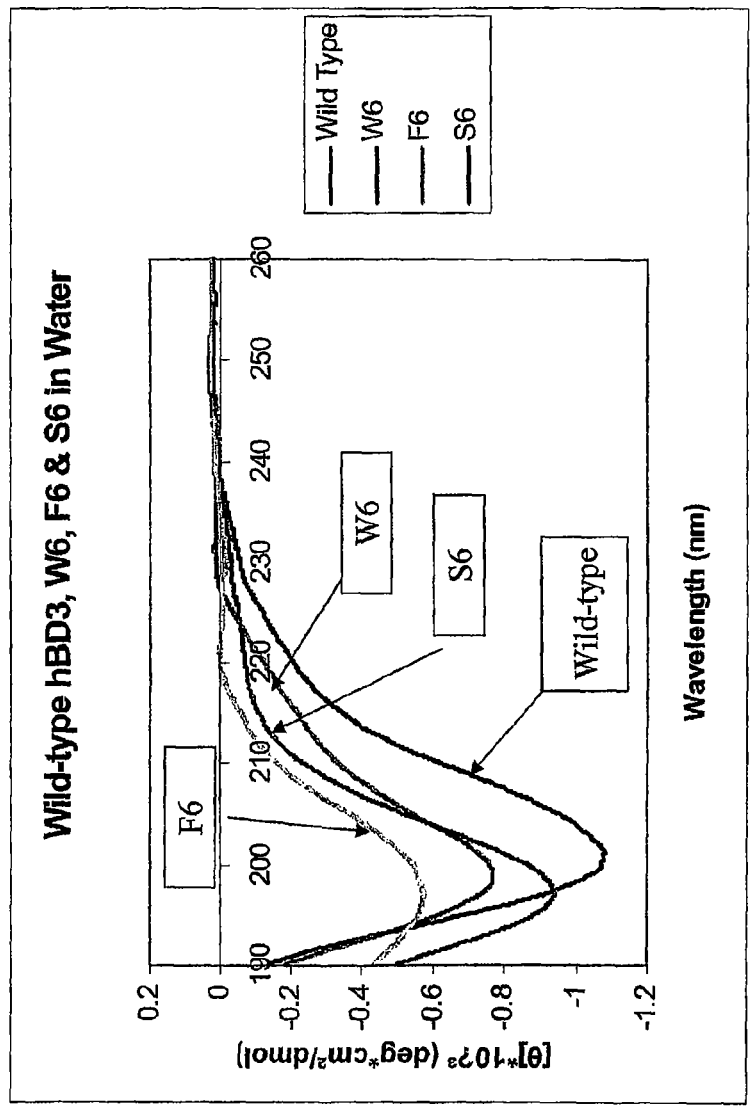
FIGS. 2(A, B) show CD (circular dichroism) spectra of wild type hBD3 and hBD3 linear analogs in water. The reference to the compound C6 in FIG. 1B, is meant to indicate the analog C(Acm)6.
Figure 2B:
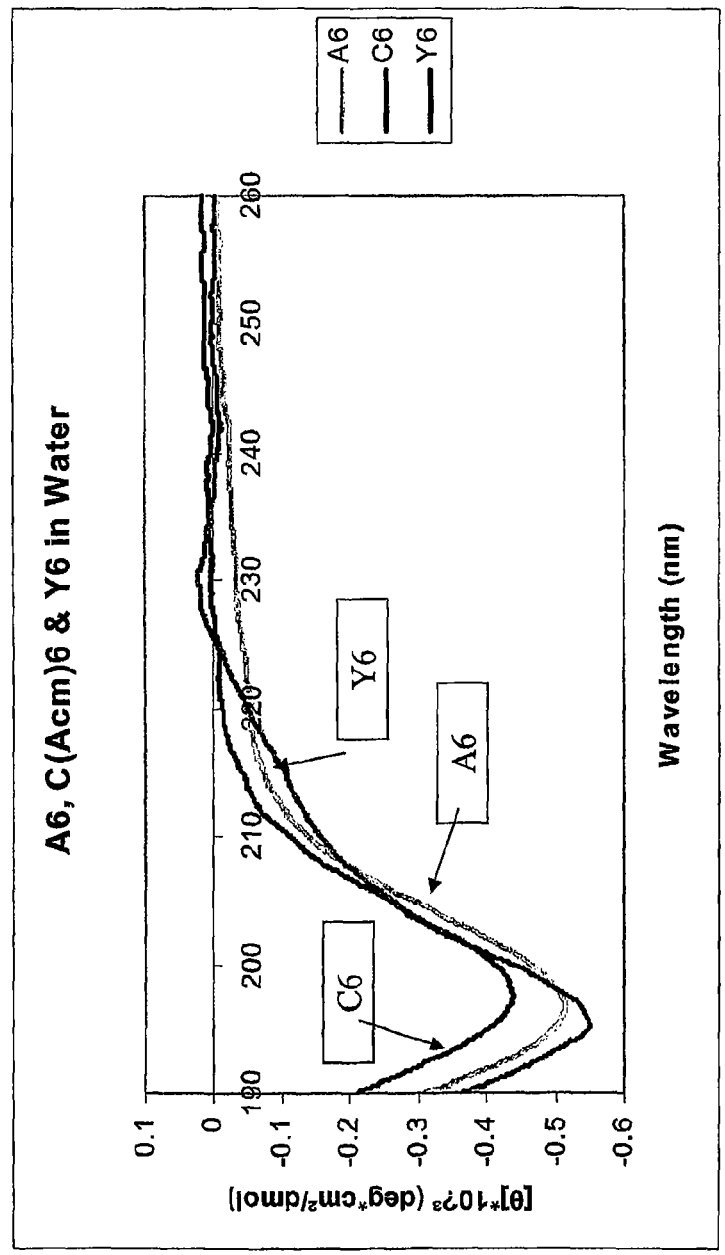
Figure 3A:
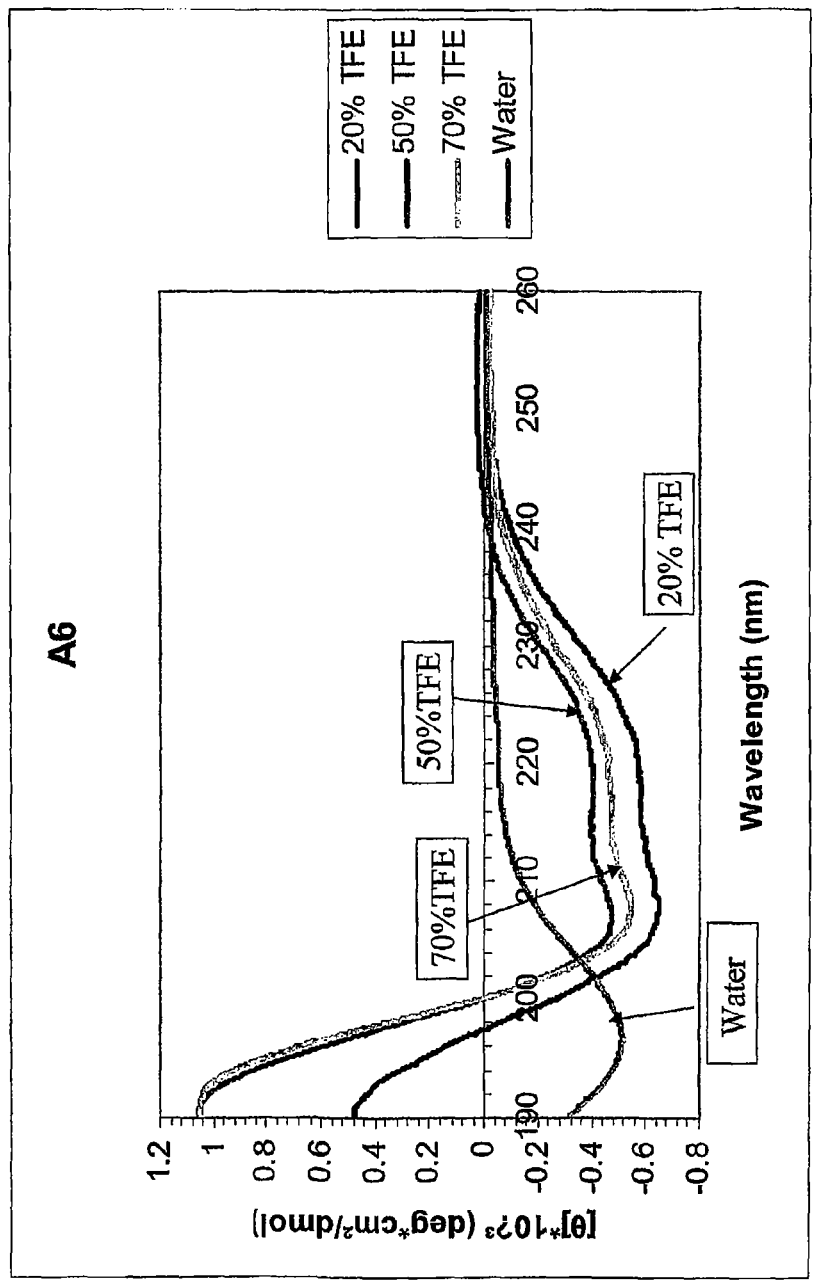
FIGS. 3(A-G) show CD (circular dichroism) spectra of wild type hBD3 and hBD3 linear analogs in TFE.
Figure 3B:
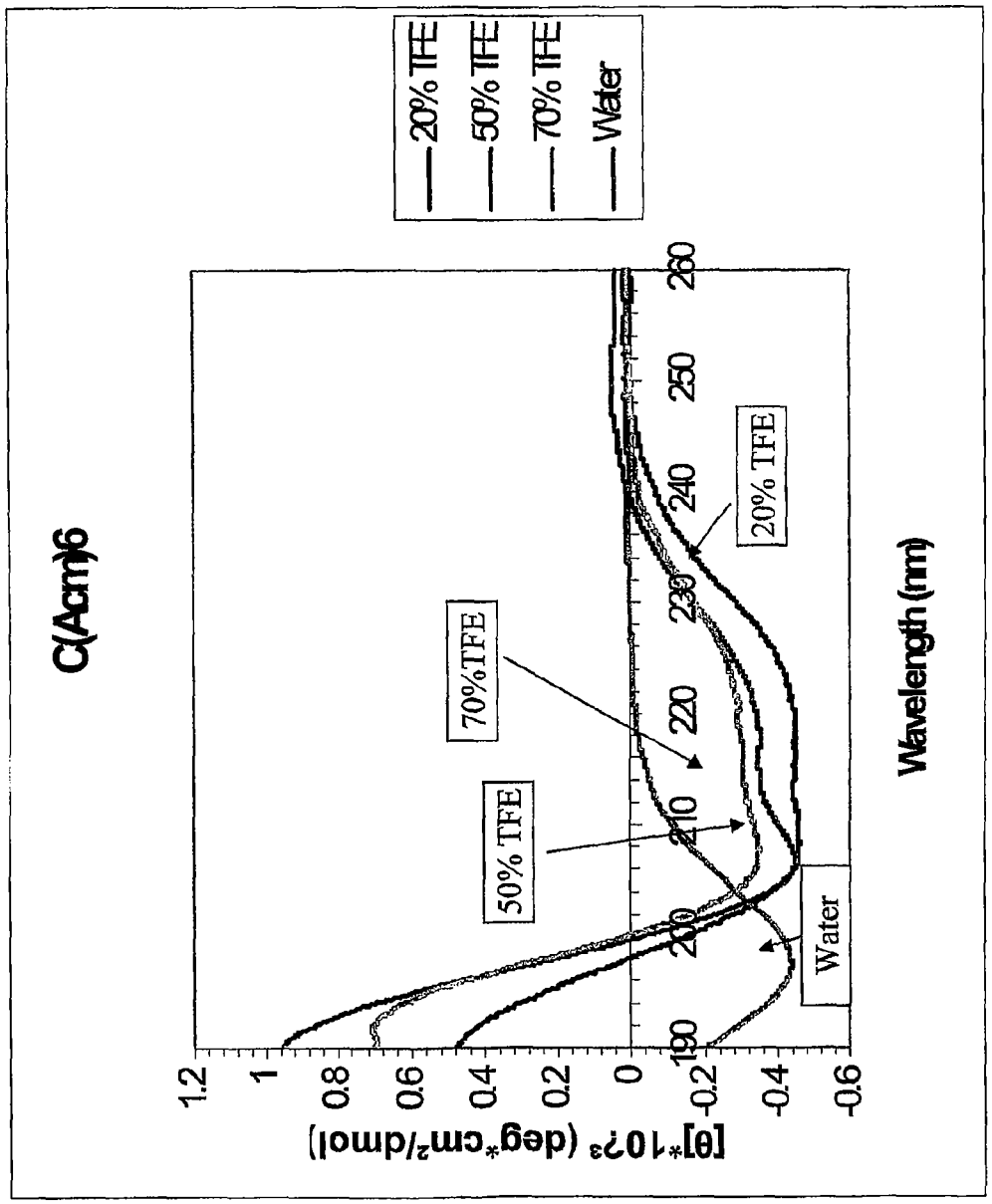
Figure 3C:
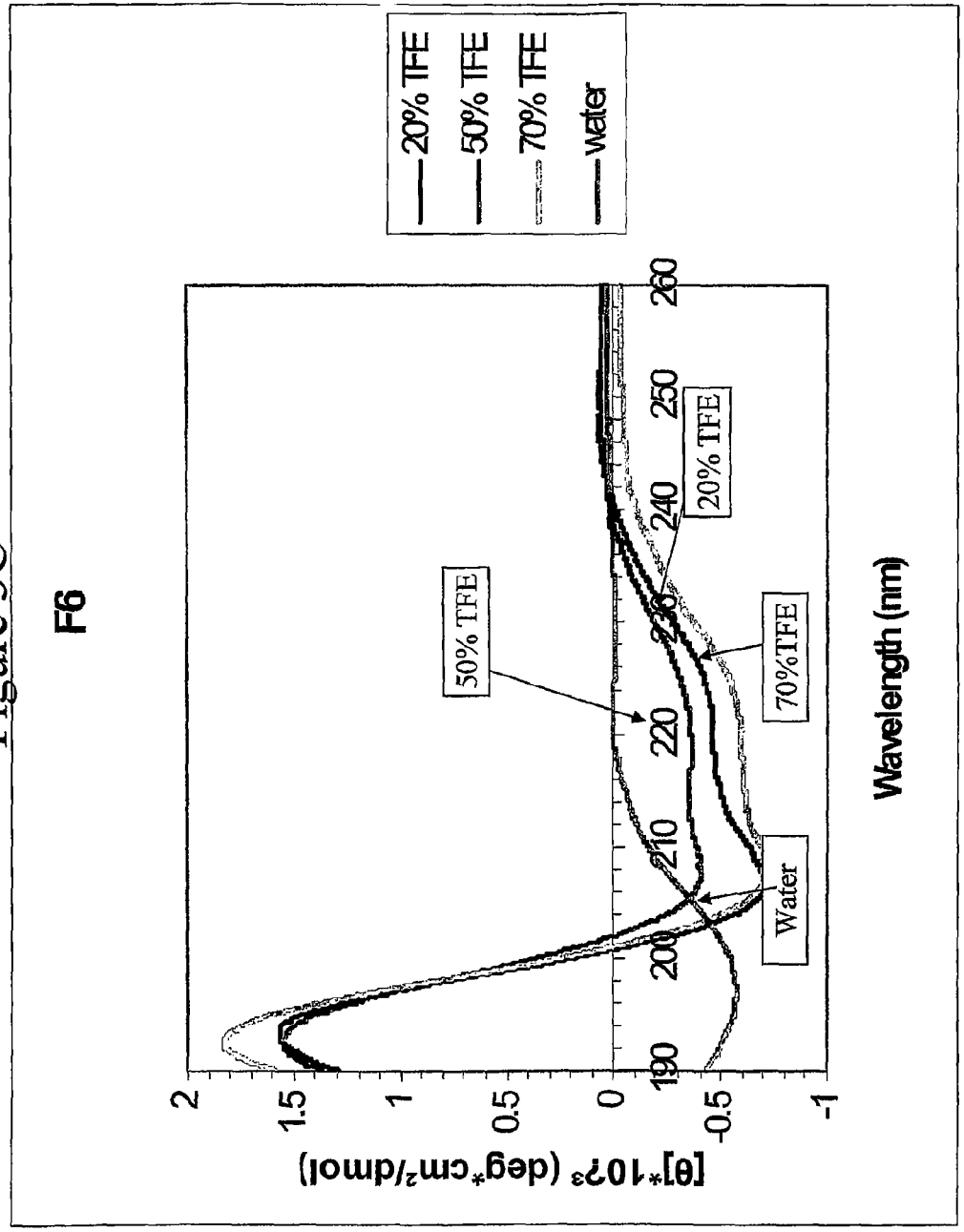
Figure 3D:
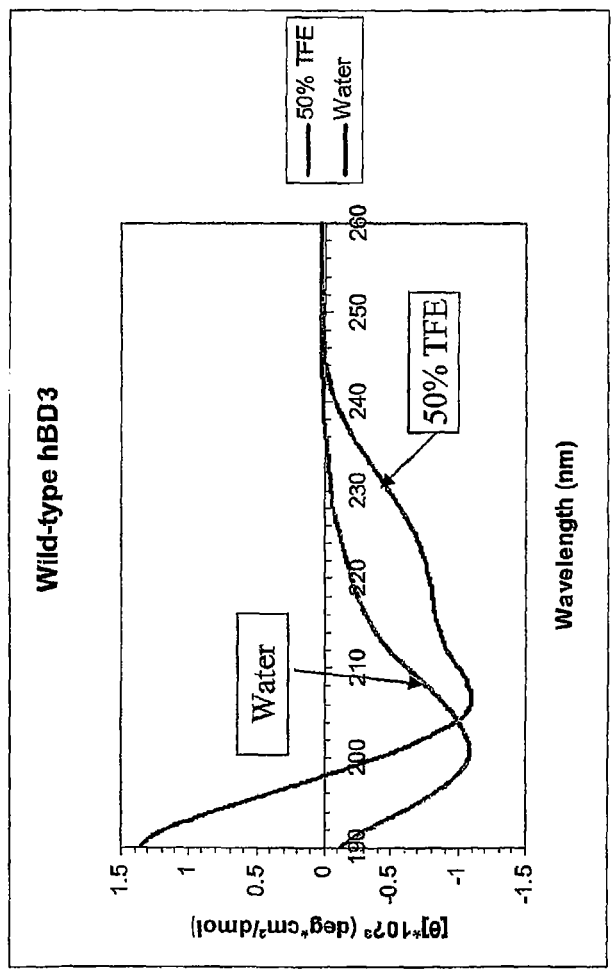
Figure 3E:
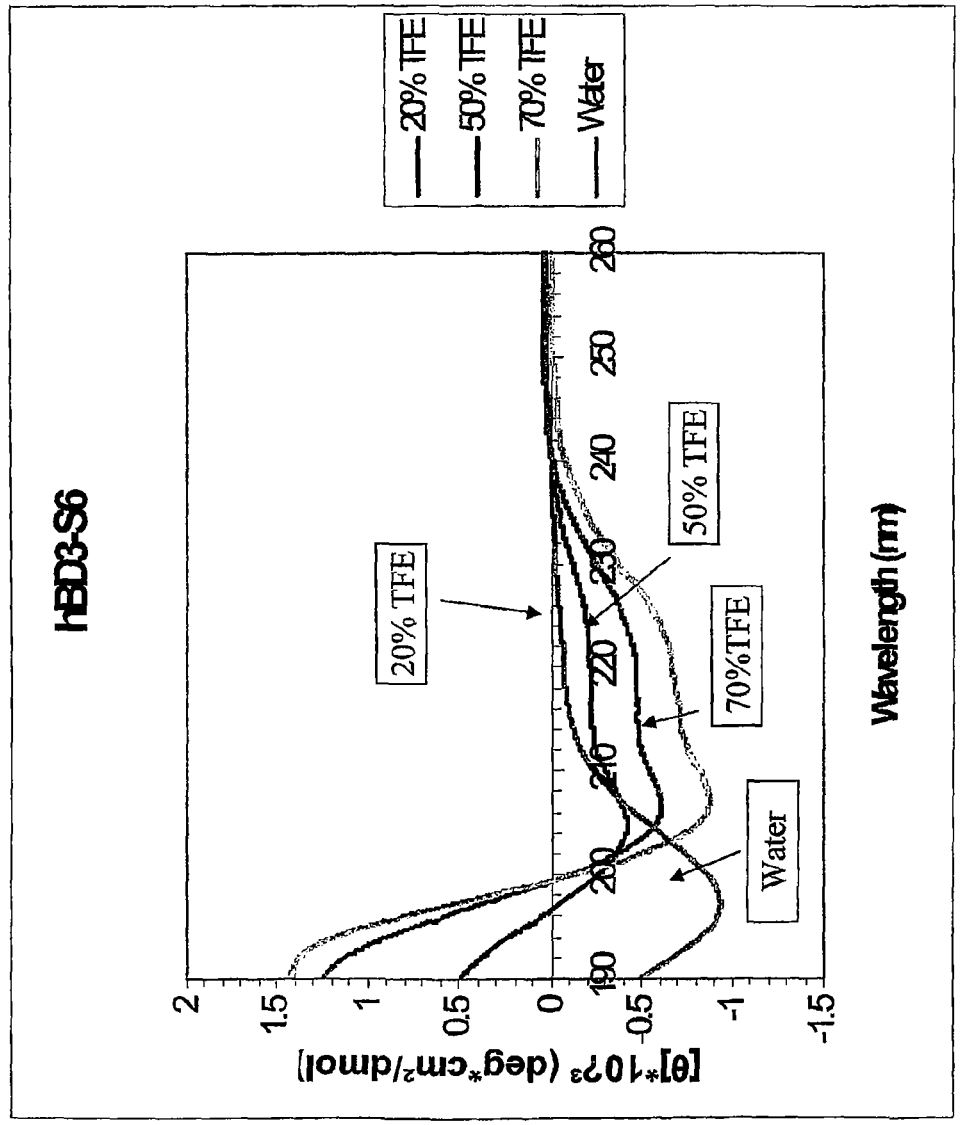
Figure 3F:
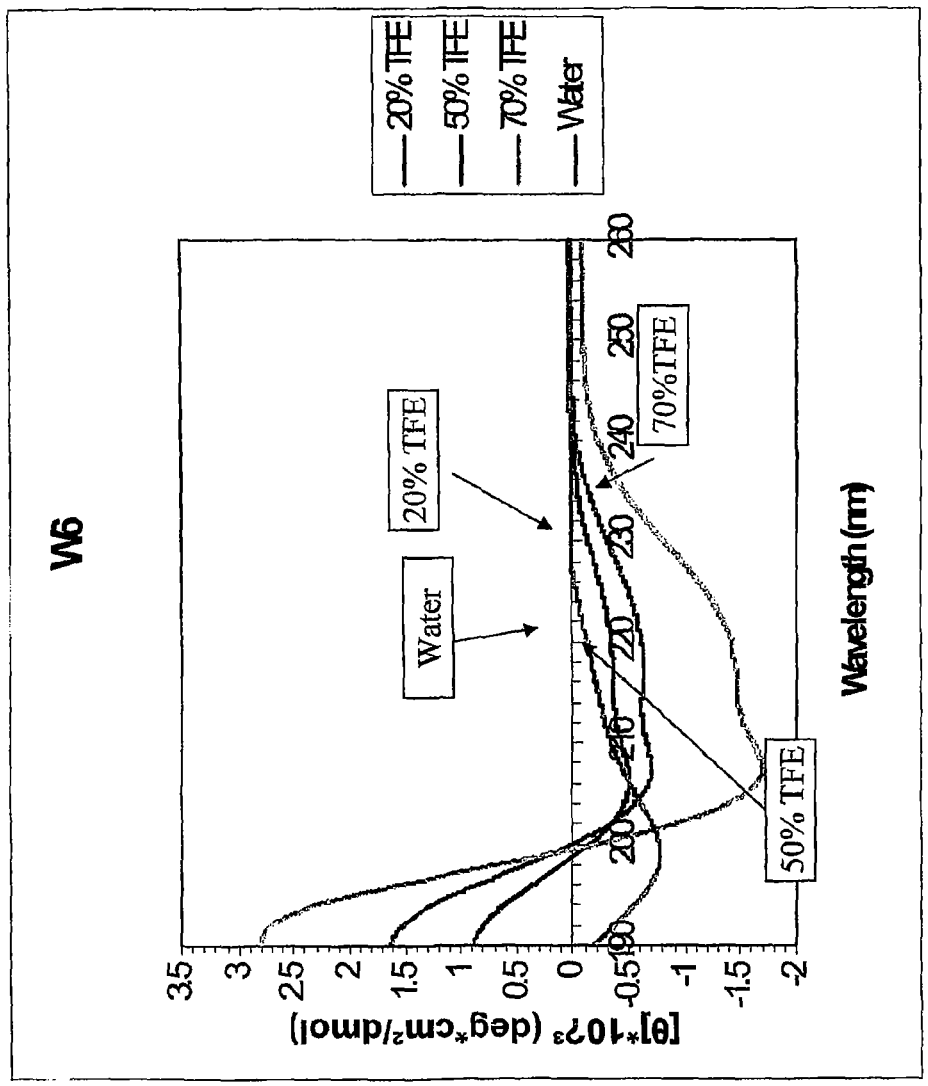
Figure 3G:
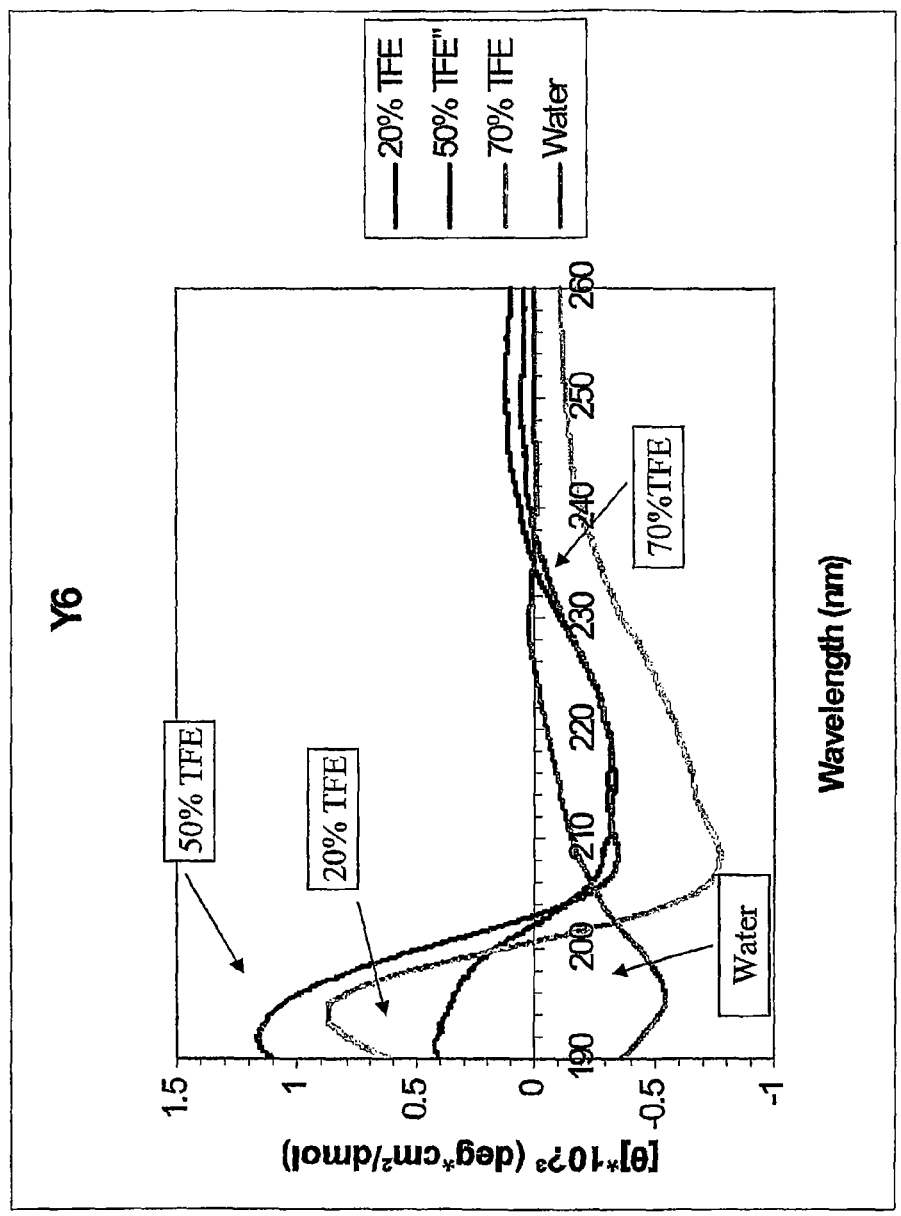
Figure 4A:
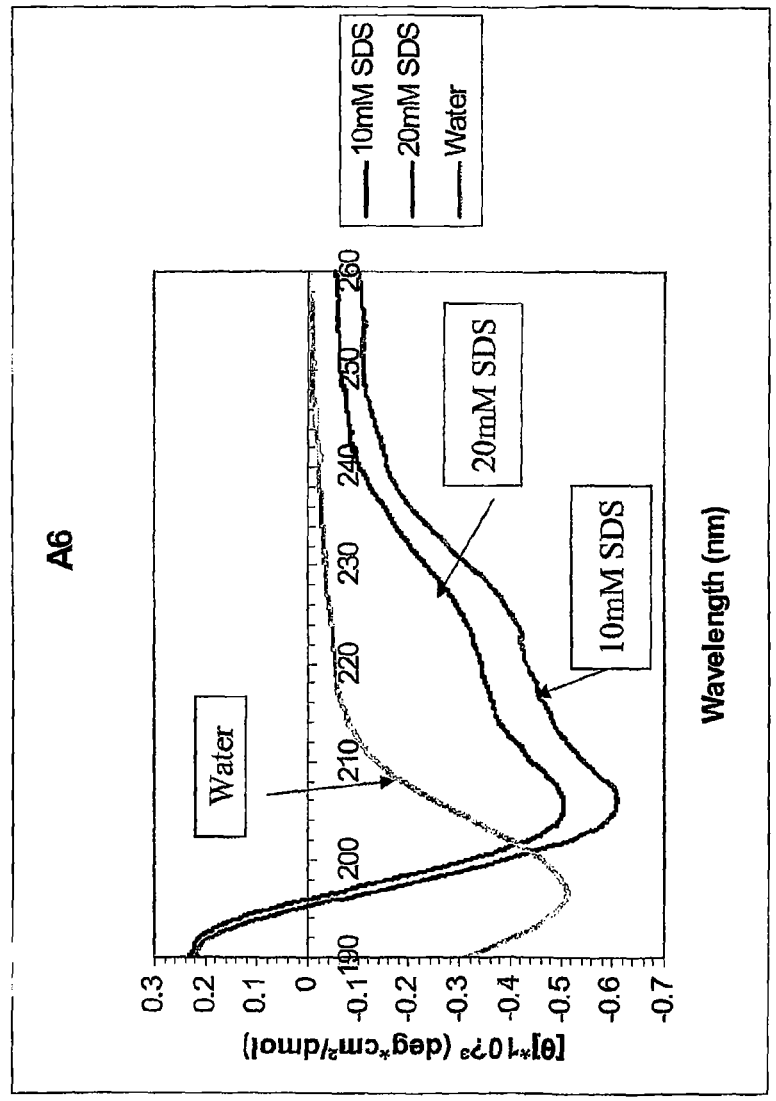
FIGS. 4(A-G) show CD (circular dichroism) spectra of wild type hBD3 and hBD3 linear analogs in SDS micelle.
Figure 4B:
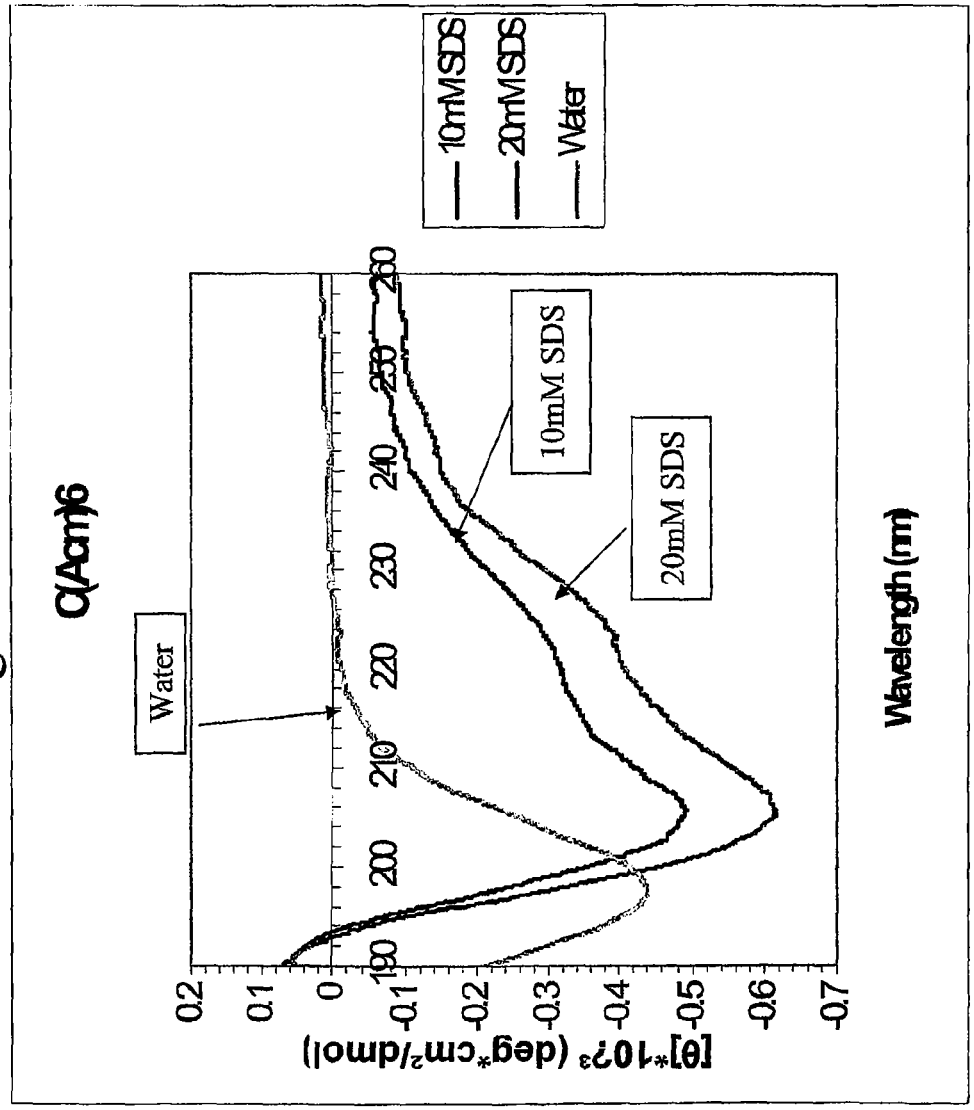
Figure 4C:
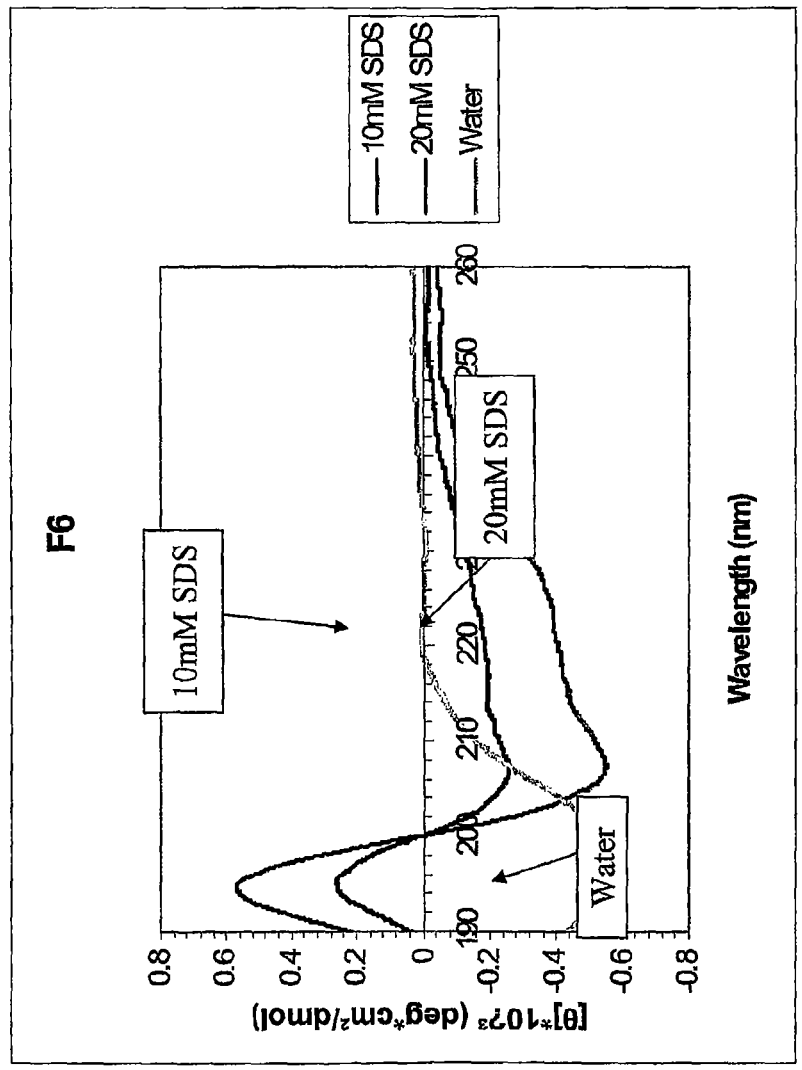
Figure 4D:
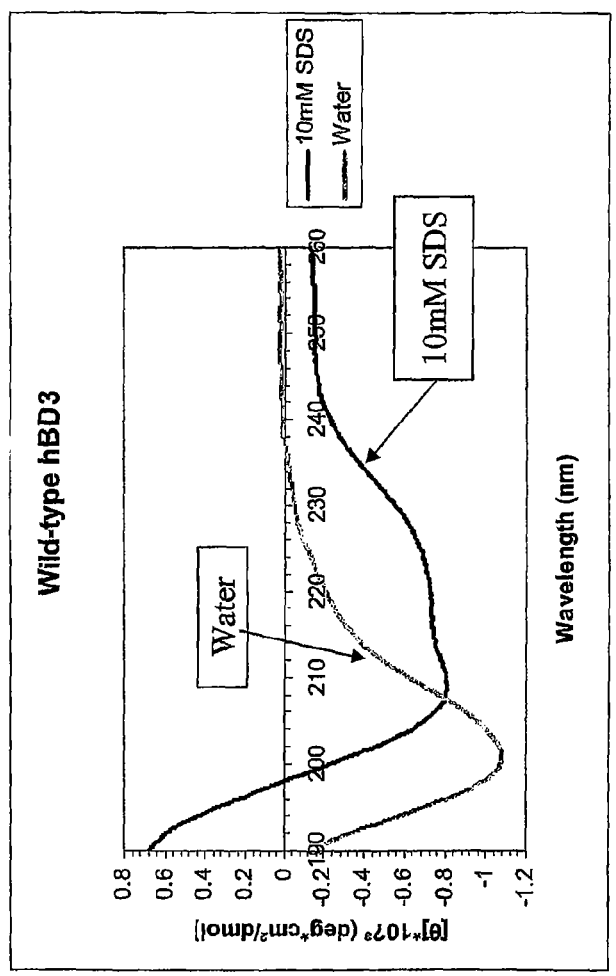
Figure 4E:
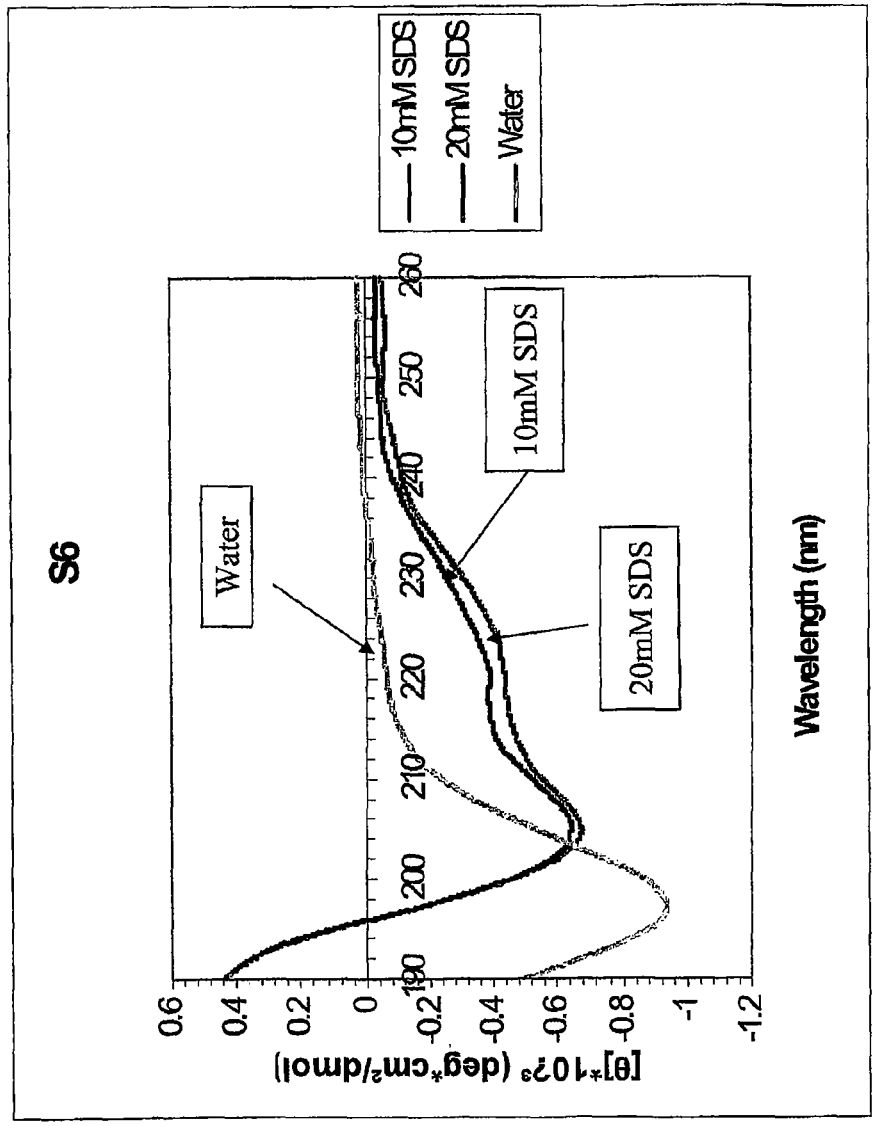
Figure 4F:
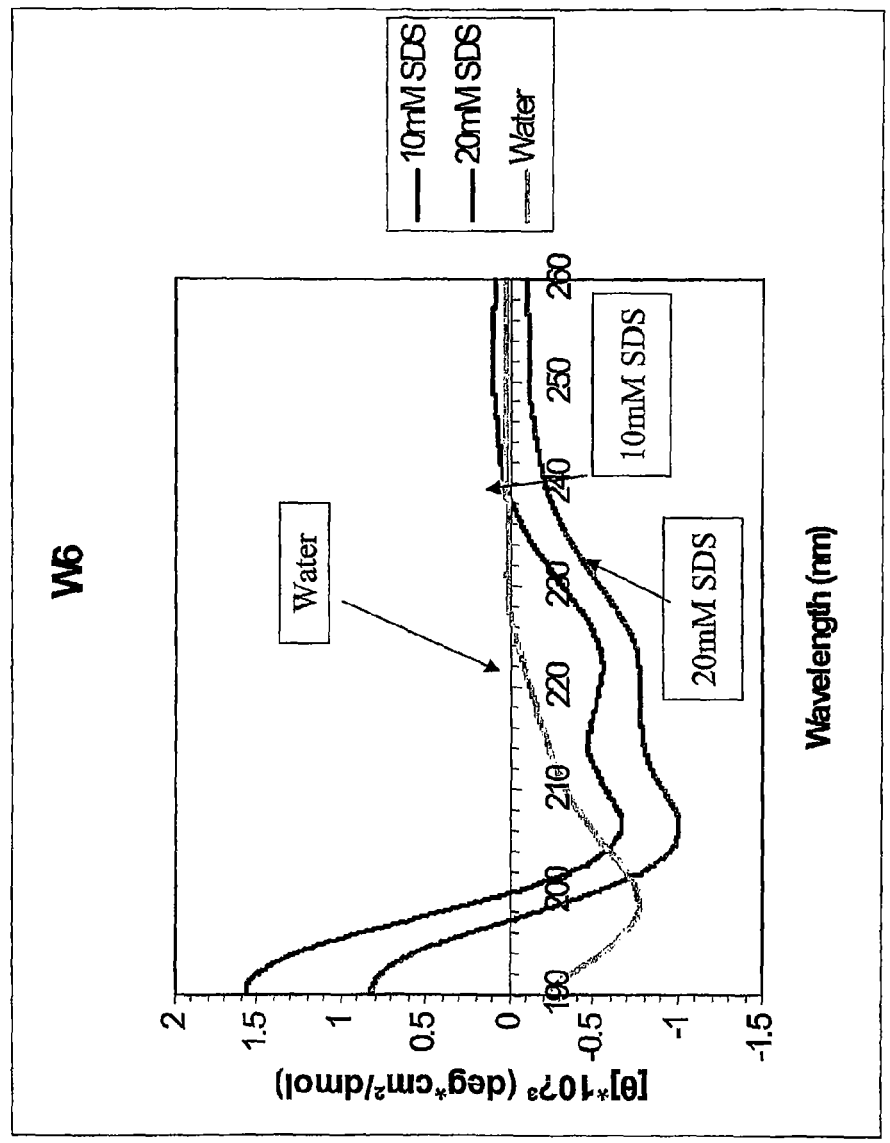
Figure 4G:
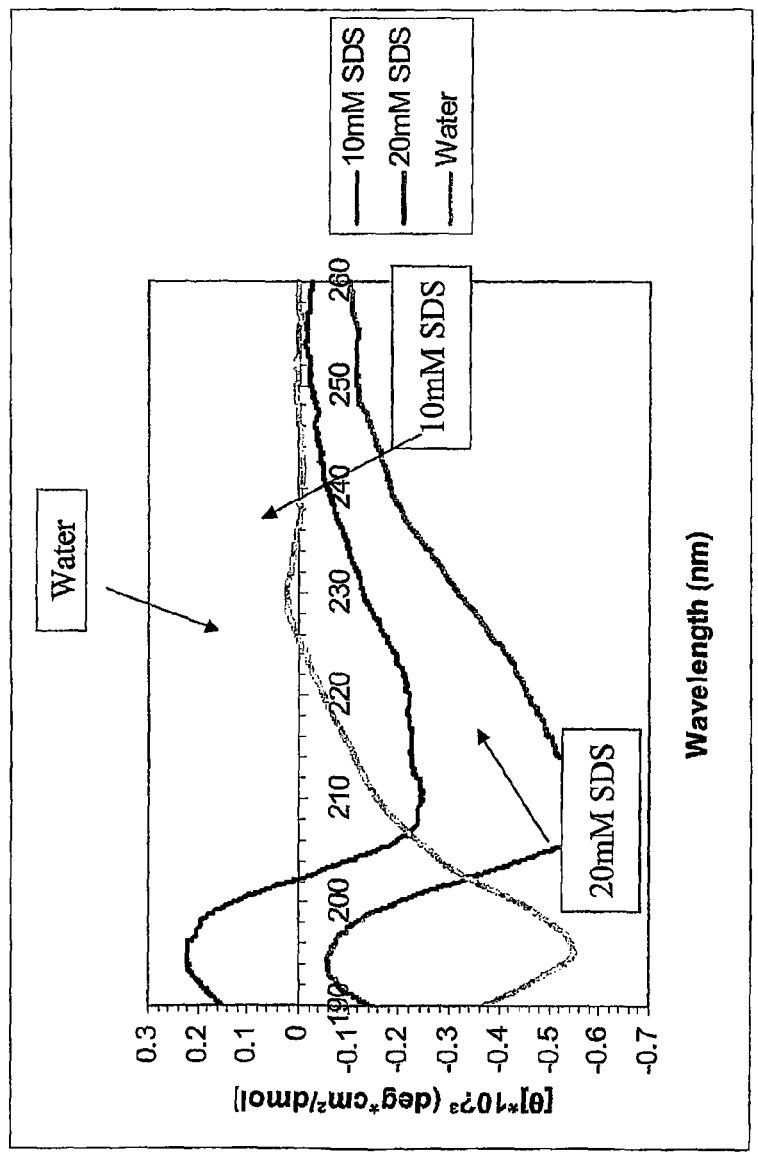

Circular dichroism spectroscopy was conducted on Jasco J-810 spectropolarimeter in aqueous solution (pH of 5.0-5.5) and other different media, e.g., 10 mM and 20 mM SDS, 20, 50, 70% (volume) TFE in DI water. The six analogs were at the concentration of 125 µg/ml and wild-type hBD3 was in 100 µg/ml. CD measurements were performed at 27° C. within a wavelength range of 196-260 nm. Every sample and solvent was scanned three times and CD of solvent was deducted from that of sample solution. The results are shown in FIGS. 2, 3 and 4.

Antimicrobial Assay for Defensins Analogs
Materials

The bacteria assayed included *Escherichia coli* ATCC 25922, *Staphylococcus aureus* ATCC 25923, *Pseudomonas aeruginosa* ATCC 27853, *Bacillus cereus* NCTC 2599. Sterile flat-bottom, 96-well tissue culture plates (92096, TPP) was used for assay. The inner surface of microplate cover was treated with 0.05% Triton X-100 in 20% ethanol to prevent condensation of water droplets. Growth kinetics in 96-well microplates was monitored (as turbidity) with the Tecan Genios Plus microplate reader using software Magellan v5.03 and 620-nm filter. Seed culture was monitored on Pharmacia Biotech Ultrospec 2000 UV/Visible spectrophotometer using 600-nm wavelength. Antibacterial activities of the analogs and wild-type hBD3 were determined for *E. coli, B. cereus, S. aureus* and *P. aeruginosa* by measuring bacteria growth in liquid broth in the presence of the serially diluted peptides. The $LD_{50}$ is the concentration of peptide at which 50% of the viable cells are killed. The results are reported in FIGS. 7(A,B,C and D).

Calibration

The bacteria were grown to mid-logarithmic phase in Mueller-Hinton Broth (MHB) from overnight plate culture. The cell suspension was diluted to OD 0.1 (600 nm, Pharmacia Biotech Ultropec 2000 UV/Visible spectrophotometer) in mixture of 10 mM Pot Phos buffer/MHB (equal volume (PMH). This cell suspension gave a concentration of $10^7$ CFU/ml. Colony count was done for confirmation. A 10-fold dilution series of this suspension ranging from $10^7$ to $10^1$ CFU/ml was made in PMH (in sextuplicate for *Staphylococcus aureus* ATCC 25923 and *Bacillus cereus* NCTC 2599; in quadruplicate for *Escherichia coli* ATCC 25922 and in triplicate for *Pseudomonas aeruginosa* ATCC 27853). The final volume per well was 200 ul. For negative control well, 200 ul of uninoculated PMH was added.

Cytotoxicity Assay

Figure 5:
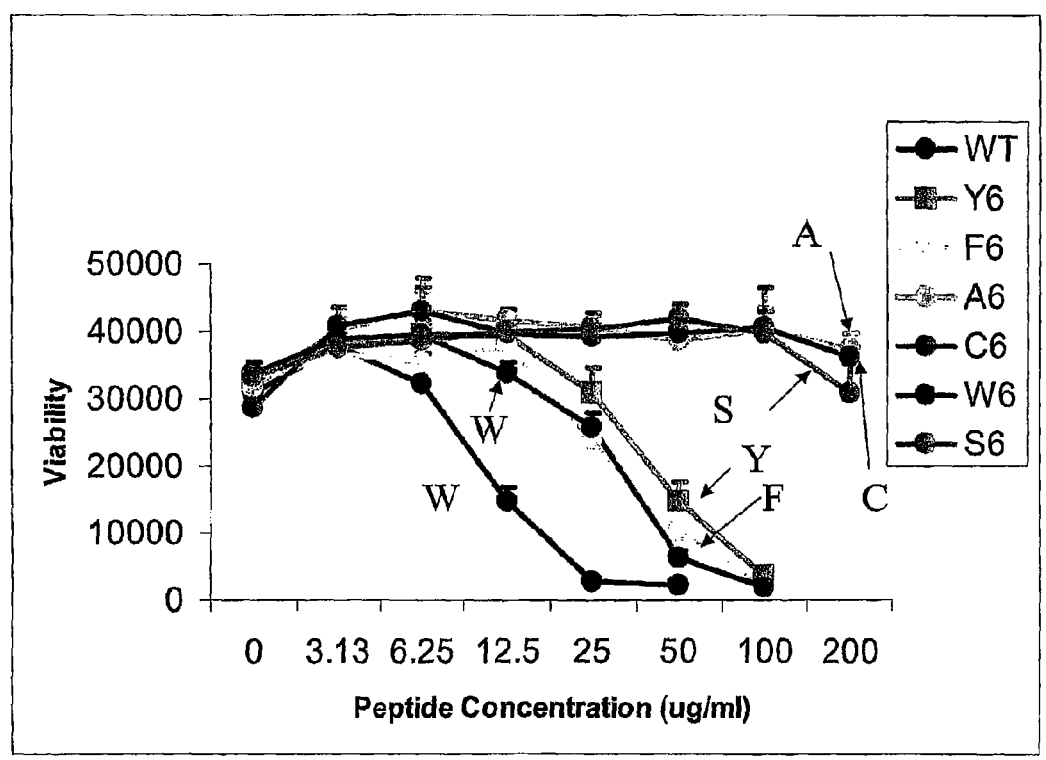
FIG. 5 shows the viability of human conjuctiva epithial cells on the concentration of hBD3 analogs.

Cytotoxicity of these analogs was analyzed on primary cultured human normal conjunctiva epithelial cells by measuring cell viability using CellTiter-blue. Wild type hBD3 was used as a control in all analyses. FIG. 5.

Hemolysis Assay

Figure 6:
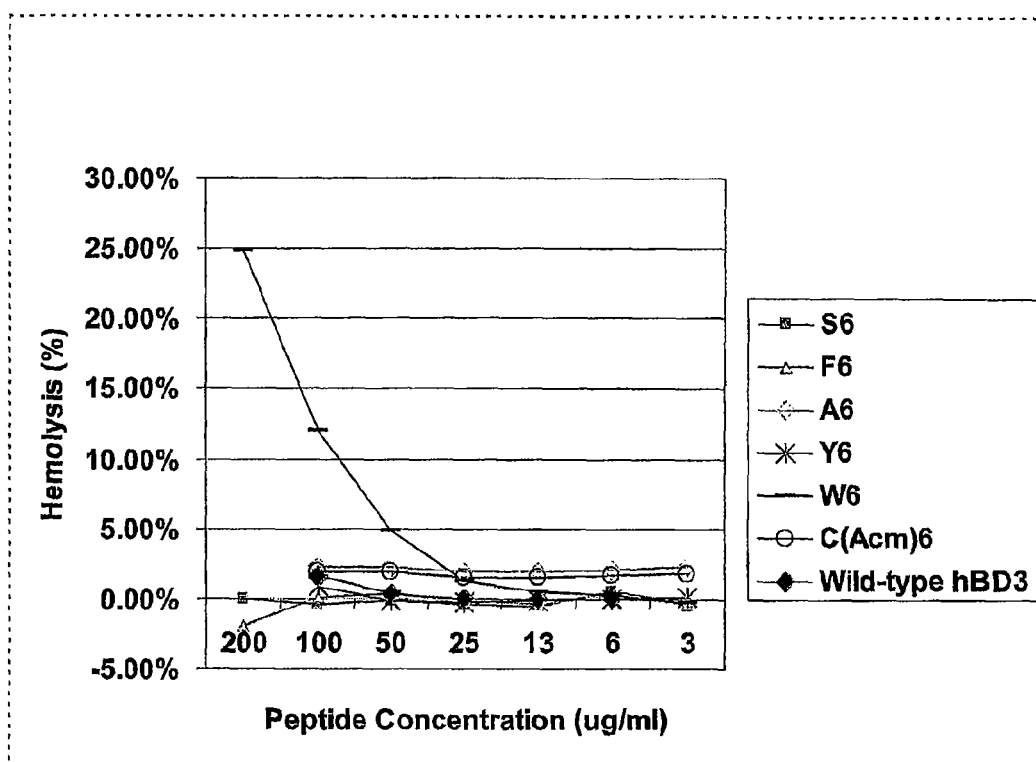
FIG. 6 shows the concentration dependence of the hemolytic effects of hBD3 analogs.
Figure 7A:
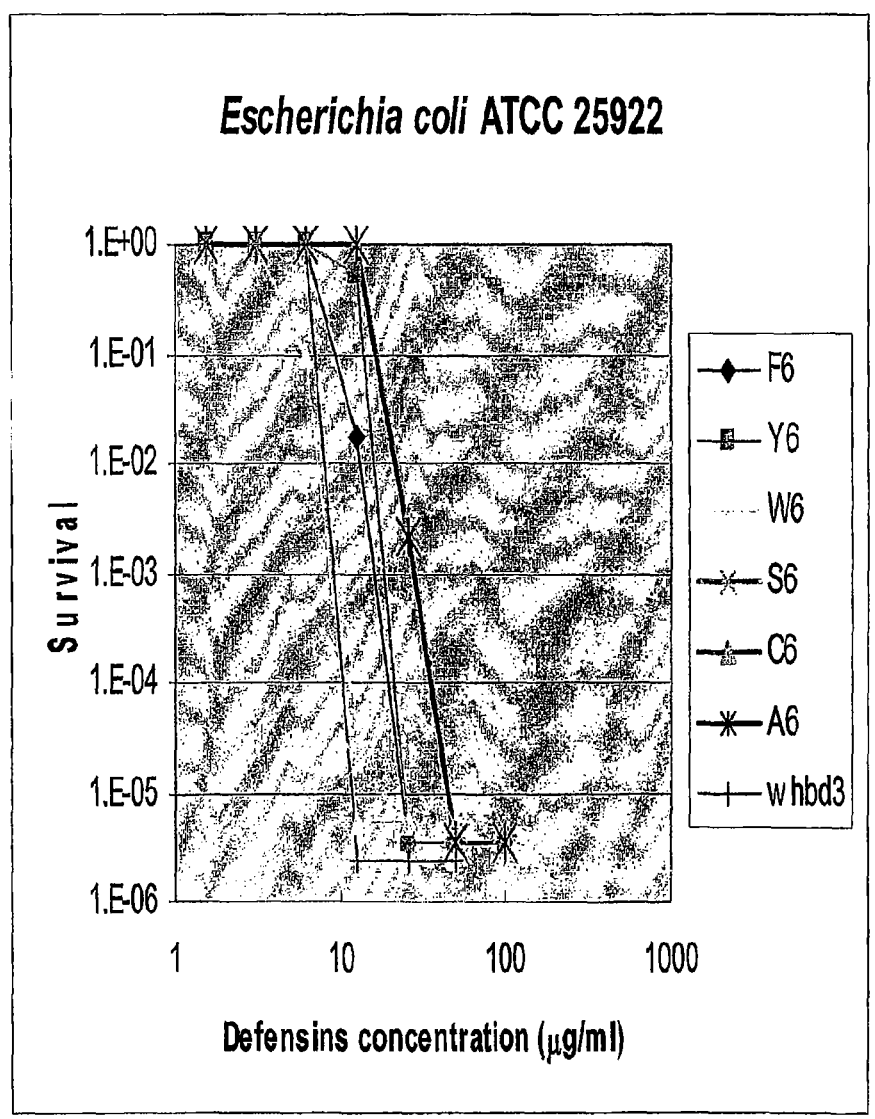
FIGS. 7(A-D) show the antibacterial activity of the hBD3 analogs.
Figure 7B:
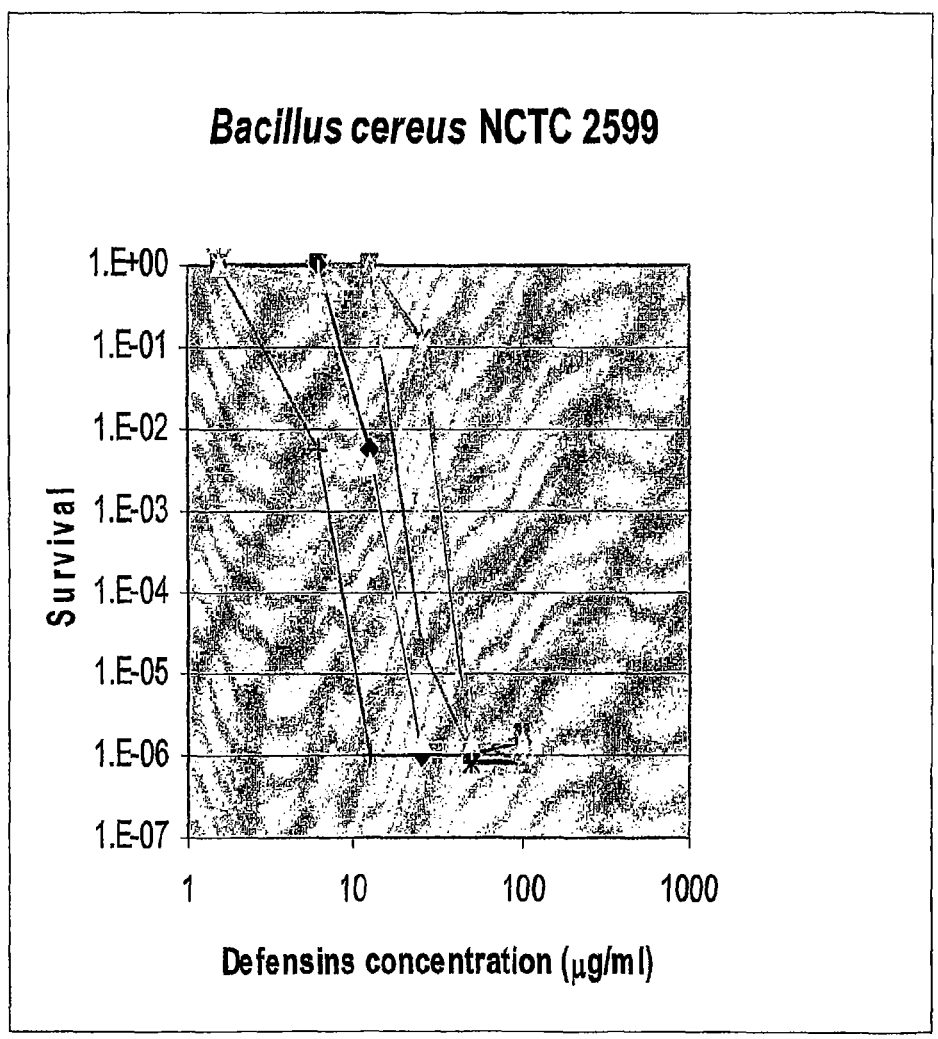
Figure 7C:
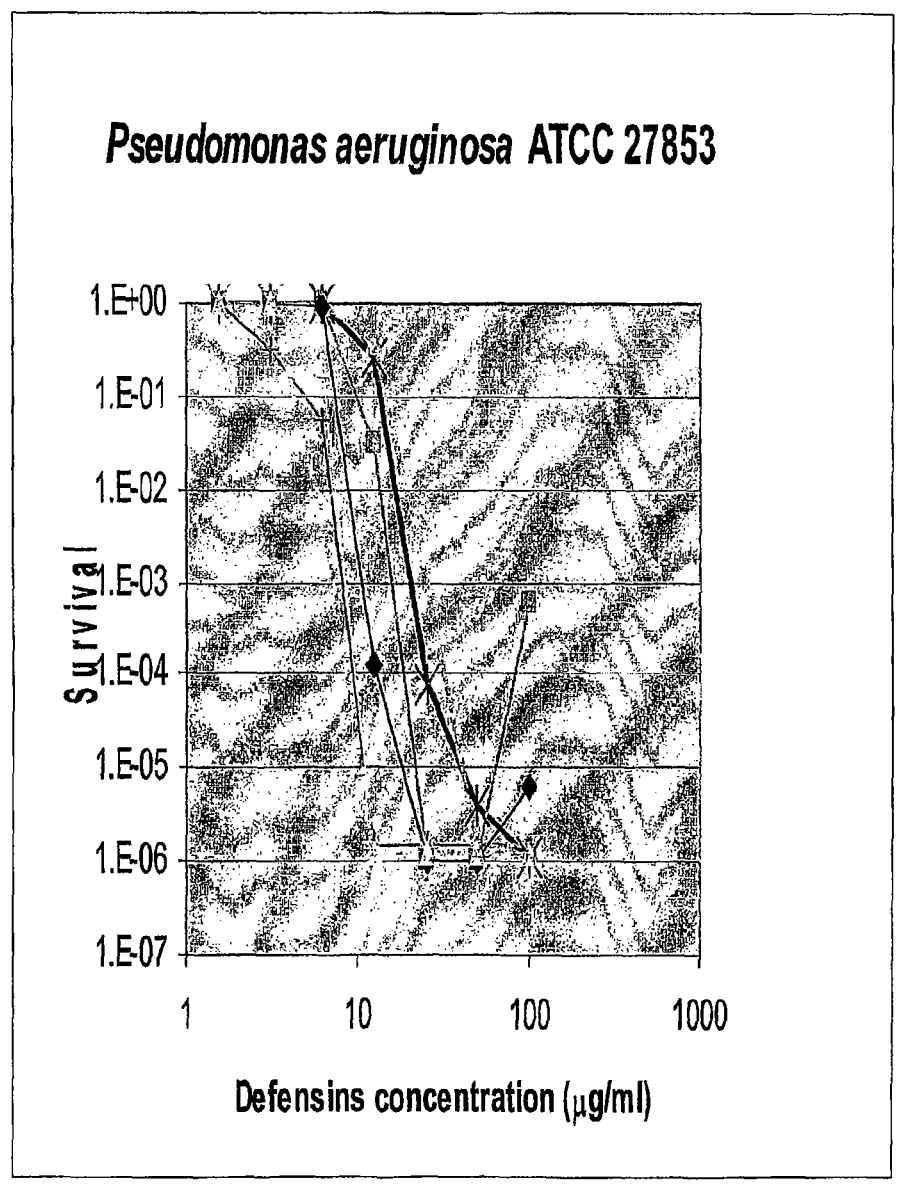
Figure 7D:
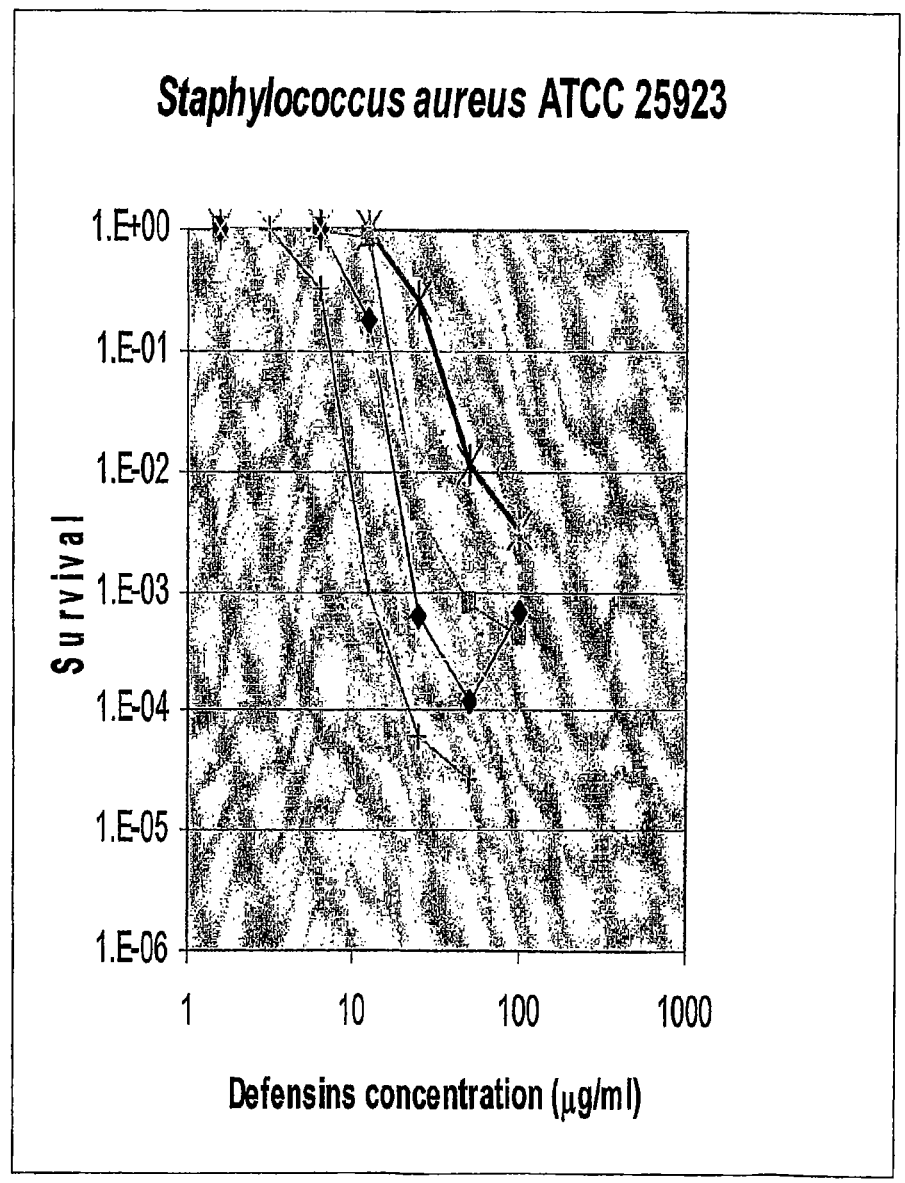

The release of hemoglobin from fresh rabbit erythrocytes was used as a measurement for the membranolytic activity of tested peptides. FIG. 6.

Results

Example 1

Linear Analogs with 45 Residues of hBD3

Synthesis of analogs of hBD3. The solid-phase synthesis of six linear analogs with 45 residues of hBD3 was performed using Fmoc-chemistry as described in detailed in Table 1. (sequence, total residue, hydrophobicity, net charge, overall hydrophobicity). Yields of crude product and pure product based on synthesis scale was reported, see supporting information Table 1.

TABLE 1 the basic physicochemical property of peptides

| Variant | Number of residues | | Net charge | Overall hydrophobicity (kcal/mol)$^a$ | Relative hydro-phobicity$^b$ |
| --- | --- | --- | --- | --- | --- |
| | Total | Hydrophobic (aromatic) | | | |
| Wt | 45 | 14 (2) | 11 | −12.65 | 20.5 |
| S6 | 45 | 14 (2) | 11 | −14.87 | 28.3 |
| C(Acm)6 | 45 | 14 (2) | 11 | (>−12.65) | n.c. |
| A6 | 45 | 14 (2) | 11 | −15.11 | 23.5 |
| F6 | 45 | 14 (8) | 11 | −7.31 | 11.5 |
| Y6 | 45 | 14 (8) | 11 | −8.45 | 12.7 |
| W6 | 45 | 14 (8) | 11 | −2.99 | 6.1 |

$^a$The overall hydrophobicity (ΔG, kcal/mol) was calculated based on the hydrophobicity scale of Wimley and White, 1996. Greater hydrophobicity is represented by a more positive ΔG;
$^b$Calculated by the Hopp-Woods scale (1983);
n.c., not calculated.

Molecular Hydrophobicity

In comparison with native hBD3, this series of linear analogs of hBD3 with full-length and 11 net positive charge are structurally homogenous as they are designed and synthesized only by uniform replacement of six bridging cysteine residues in hBD3 with other six residues with different hydrophobicity, e.g., A, S, C(Acm), F, Y and W. These linear analogs provide a well-defined model for testing the effect of overall hydrophobicity, second structure and linearity/or constraint imposed by three disulfide bridges on antibacterial, cytotoxicity and hemolytic activities. We have measured the relative molecular hydrophobicity by HPLC-MS in term of retention time (tR) at 500 ug/ml and 100 ug/ml (Table 2) and overall hydrophobicity were calculated based on the hydrophobicity scale of Wilmley and White and Hopp-Woods Scale, respectively. The change trend of overall hydrophobicity, which is calculated based on two different scale, generally fits well, and the HPLC result matches the calculations very well. The general order for the relative molecular hydrophobicity of peptides is as following: W6>F6>Y6>native hBD3>A6>S6>C(Acm)6. However the order for the hydrophobicity of replacement residue is as following: Phe>Tyr=Trp>Cys>Ala>Ser (the data for C(Acm) is unavailable) [Black, S. D. and Mould, D. R. (1991)], the trend of overall hydrophobicity of peptides does not always match that of replacement residues due to the peptide folding in aqueous solution. In the following sections, we will discuss the effect of overall hydrophobicity of peptide on biological activities.

TABLE 2

Relative hydrophobicity of peptides in term of retention time (Rt) in HPLC-MS

| Variant | Fragment | 1st Try | 2nd Try | 3rd Try | Average | Standard Deviation STDEV |
| --- | --- | --- | --- | --- | --- | --- |
| | | Retention Time (500 ug/ml) | | | | |
| W6 | 809.4 | 29.3 | 29.3 | 29.19 | 29.26 | 0.06 |
| | 944.2 | 29.31 | 29.31 | 29.25 | 29.29 | 0.03 |
| | 1132.9 | 29.26 | 29.32 | 29.26 | 29.28 | 0.03 |
| F6 | 905.2 | 27.51 | 27.77 | 27.67 | 27.65 | 0.13 |
| | 1086 | 27.46 | 27.71 | 27.76 | 27.64 | 0.16 |
| Y6 | 921.2 | 23.68 | 23.89 | 23.99 | 23.85 | 0.16 |
| | 1105.3 | 23.64 | 23.84 | 23.94 | 23.81 | 0.15 |
| Wild-type hBD3 | 860.2 | 23.22 | 23.27 | 23.22 | 23.24 | 0.03 |
| | 1032.2 | 23.28 | 23.33 | 23.23 | 23.28 | 0.05 |
| A6 | 829.2 | — | 22.41 | 22.31 | 22.36 | 0.07 |
| | 994.8 | 22.45 | 22.36 | 22.36 | 22.39 | 0.05 |
| S6 | 845.1 | 20.62 | 20.21 | 20.16 | 20.33 | 0.25 |
| | 1013.9 | 20.58 | 20.17 | 20.12 | 20.29 | 0.25 |
| C(Acm)6 | 799.3 | 19.9 | 20.35 | 20.12 | 20.12 | 0.22 |
| | 932.4 | 19.96 | 20.35 | 20.13 | 20.15 | 0.19 |
| | 1118.8 | 19.96 | 20.3 | 20.08 | 20.11 | 0.17 |
| | | Retention Time (100 ug/ml) | | | | |
| W6 | 809.4 | 29.59 | 29.7 | 29.7 | 29.66 | 0.06 |
| | 944.2 | 29.99 | 29.65 | 29.7 | 29.78 | 0.18 |
| | 1132.9 | 29.71 | 29.6 | 29.71 | 29.67 | 0.06 |
| F6 | 905.2 | — | — | — | — | |
| | 1086 | 28.12 | 28.32 | 28.32 | 28.25 | 0.12 |
| Y6 | 921.2 | 24.4 | 24.45 | 24.35 | 24.4 | 0.05 |
| | 1105.3 | 24.3 | 24.4 | 24.35 | 24.35 | 0.05 |
| Wild-type hBD3 | 860.2 | 24.14 | 24.4 | 24.29 | 24.28 | 0.13 |
| | 1032.2 | 24.61 | 24.15 | 24.1 | 24.29 | 0.28 |
| A6 | 829.2 | — | — | — | — | |
| | 994.8 | 22.66 | 22.1 | 22.31 | 22.36 | 0.28 |
| S6 | 845.1 | 20.47 | 20.57 | 20.27 | 20.44 | 0.15 |
| | 1013.9 | — | — | — | — | |
| C6 | 799.3 | — | — | — | — | |
| | 932.4 | — | — | — | — | |
| | 1118.8 | 20.7 | 21.09 | 21.03 | 20.94 | 0.21 |

The increase in antibacterial and hemolytic activity with increasing hydrophobicity is in accordance with literature reports that predict large hydrophobic groups will have stronger interactions with the inner core of cell membranes leading to loss of selectivity. [Ilker, et al., JACS, 2004, 126, 15870-75, see also ref 1, 4 cited in this publication]. In many instances, hydrophobic interactions have been reported to control hemolytic activities; whereas electrostatic interactions are suggested to be more important for antibacterial activity (Harder et al., 2001). These results show that the presence of proper hydrophobic residues, e.g. W, F and S, and balance of hydrophobic to hydrophilic surface area are key structural determinants which indicate the antibacterial and hemolytic activities.

CD Spectroscopy and Peptide Secondary Structure

Previous X-ray and NMR studies [some publications, including hBD2, Sawai et al., Biochemistry, 2001, 40, 3810-16; hBD3, Schibli et al., JBC 2002, 277(10), 8279-89] have shown that the tertiary structures of human β-defensins (hBD1-3) are similar with a short α-helical segment proceeding a triple-stranded anti-parallel β-sheet held rigidly by three disulfide bonds. However, in the absence of constraints imposed by three disulfide bonds, linear analogs of hBD3 are likely to be flexible and random in aqueous solution, adopting conformations dictated by the environment. Therefore, it was of interest to systemically determine the solution conformations of the linear peptides by CD spectroscopy. An analysis of the structural characteristics of hBD3 derivatives was performed by CD spectrometry in an aqueous solution and in the presence of the organic modifier trifluoroethanol (TFE) or membrane mimetic SDS micelle. (FIGS. 2-4). TFE has been widely used in protein structure study since it can induce the adoption of stable, protein-like conformations from otherwise unstructured/random peptides in aqueous solution. The CD spectra of six linear analogs and wild-type hBD3 in aqueous solution are very similar, and agree very well with the CD spectrum of native hBD3. All analogs and wild-type hBD3 in water had a strong minima at 196-200 nm in accordance with a predominantly unordered structure, showing largely random coil structure in aqueous solution. This result shows that the existence of three disulfide bonds or their absence and the type of replacement for the amino acid residues has no significant effect on the secondary structure of hBD3 derivatives, thus, the secondary structure seems to be dictated independently of the presence of multiple disulfide bridges or the replacement residues of the six cysteine residues. In the presence of different amounts of an organic modifier, TFE, in water, e.g., 20, 50, 70% (only CD spectra in 50% TFE was reported here), all analogs and native hBD3 undergo a marked conformational transition, their CD spectra were red-shifted with clearly observable double minima at wavelengths of 205-222 nm and a strong positive peak at around 190-193 nm. Such a spectrum is characteristic of α-helical structures and therefore it is possible to conclude that the presence of TFE increases the proportion of helical conformation in these peptides solutions. The α-helix content of the six analogs and wild-type hBD3, especially for W6, S6, F6, wild-type hBD3 and Y6, greatly increased in the presence of THF, which is known to stabilize this type of conformation, their difference in α-helix content may arise from possible stacking of aromatic ring side groups of residues in W6, F6, Y6, or possible hydrogen-bonding between side groups of residues in A6 or the stabilization force of three disulfide bonds to the well-defined conformations of α-helix in/for wt-hBD3. In some cases (W6, S6, C(Acm)6), the higher the concentration of TFE, the higher α-helix content. This CD transition also occurs in 10 mM and 20 mM SDS micelles, which better mimic the anisotropic lipid environment of membranes, the α-helix content of the six analogs and wild-type hBD3, especially for W6, S6, wild-type hBD3, F6 and Y6, also increased to some extent due to the same effect of structural determinants as they do in the presence of TFE. In most cases, especially for W6 and Y6, α-helix content is higher at 10 mM rather than 20 mM SDS. Furthermore, if the molecule is rigid, it would be expected to be resistant to any major solvent-induced conformational changes. However, in the presence of TFE and SDS, the CD spectrum appears to change dramatically, indicating the strong interactions of the peptides with the solvents.

The molecular weight of six linear analogs was characterized by use of Mass Spectrometry according to standard technique known to any skilled person in the art. The results are reported in FIGS. 8-13.

It was reported that no correlation has been generally been observed between degree of helicity and antibacterial activity; high helicity often correlates with high hemolytic properties, albeit not with antibacterial activity [Oren et al., Biochemistry, 1997, 36, 1826-35]. The correlation between helicity and antibacterial activity, cytotoxicity and hemolytic activity will be discussed in the following sections.

Antibacterial Activity

LD50, LD90, LD99 and LD99.9 of wild-type hBD3 and its linear analogs were determined against two Gram-negative (E. Coli and P. aeruginosa) and two Gram-positive (B. cereus, S. aureus) (Table 3). See also FIGS. 7(A, B, C and D).

Table 3 shows the pathogen(s) killing ability of the wt hBD3 and its linear analogs.

| Peptide | vLD50 (µg/ml) | vLD90 (µg/ml) | vLD99 (µg/ml) | vLD99.9 (µg/ml) |
|---|---|---|---|---|
| P aeruginosa, ATCC27853 | | | | |
| whbd3 | 2.7 | 5.7 | 11.4 | 12.4 |
| F6 | 9.2 | 11.8 | 12.4 | 12.5 |
| A6 | 10.3 | 20.2 | 24.5 | 24.9 |
| C6 | 11.2 | 21.7 | 24.7 | 25 |
| Y6 | 9.4 | 12.1 | 21.5 | 24.5 |
| S6 | 4.7 | 5.9 | 6.2 | 11.4 |
| W6 | 5.1 | 9.5 | 12.2 | 12.5 |
| Staph aureus, ATCC25923 | | | | |
| whbd3 | 5.5 | 10.7 | 12.2 | 12.5 |
| F6 | 10.1 | 18 | 24.4 | 24.9 |
| A6 | 20.8 | 41 | 50 | >100 |
| C6 | 25 | 46.8 | 91 | >100 |
| Y6 | 17.7 | 23.6 | 24.9 | 48.4 |
| S6 | 9.8 | 15.1 | 24.5 | >100 |
| W6 | 1.5 | 5.6 | 10.4 | 12.4 |
| E coli, ATCC25922 | | | | |
| whbd3 | 9.3 | 11.8 | 12.4 | 12.5 |
| F6 | 9.4 | 12 | 17.7 | 24.3 |
| A6 | 18.7 | 23.8 | 24.9 | 38.5 |
| C6 | 18.7 | 23.8 | 24.9 | 42 |
| Y6 | 13 | 22.6 | 24.8 | 25 |
| S6 | 9.3 | 11.8 | 12.4 | 12.5 |
| W6 | 4.8 | 6.2 | 11.9 | 12.5 |
| B cereus, NCTC2599 | | | | |
| whbd3 | 3.9 | 5.8 | 6.2 | 6.2 |
| F6 | 9.4 | 11.9 | 12.5 | 12.5 |
| A6 | 19.6 | 29 | 47.9 | 49.8 |
| C6 | 19.6 | 28.3 | 47.8 | 49.8 |
| Y6 | 18.7 | 23.75 | 24.8 | 25 |
| S6 | 11.3 | 22.25 | 24.75 | 25 |
| W6 | 7.4 | 11.5 | 12.4 | 12.5 |

Our result of full-length linear hBD3 analogs shows that the replacement of the six cysteine residues by alanine (A), serine (S), cysteine protected by Acm [C(Acm)], tryptophan (W), tyrosine (Y), and phenylalanine (F), respectively, has some effect on antibacterial activity. W6, S6 and F6 are the most potent analogs in comparison with hBD3, while Y6, C(Acm)6 and A6 have relatively less potency. W6 has lower LD50, being lower than 5 µg/ml, against E. coli and S. aureus and it has comparable LD50, being less than 8 µg/ml, against P. aeruginosa and B. cereus. S6 and F6 also have comparable level LD50s (less than 10 µg/ml) against the four pathogens. For C6, Y6 and A6, most LD50s against pathogens are in the range of 10-20 µg/ml. The result show this series of linear analogs, especially W6, S6 and F6 have high activity to kill E. coli, P. aeruginosa and S. aureus compared with the cyclic or noncylic 40-reside hBD3 derivatives [Enno Kluver et al., Biochemistry, 2005], which were measured in terms of the minimum inhibition concentration (MIC). LD90s of S6, W6 and F6 are in the range of 5-20 µg/ml, they have comparable activity in comparison with wt hBD3 and other cyclic or linear hBD3 analogs, which have most potent activity [Hoover et al., Antimicrobial Agents and chemotherapy, 2003, 47(9), 2804-09].

The fact that the 45-residue full-length linear variants are as active as their wild type hBD3 with multi disulfide bridges shows that the presence of three disulfide bonds is not a necessary requirement for antimicrobial activity. In contrast, reduced hBD2 was earlier reported to be inactive as a antimicrobial [Enno Kluver et al., Biochemistry, 2005]. The tryptophan-rich derivative, W6, is the most potent antimicrobial. This high activity can be assigned to the presence of six tryptophan residues. The tryptophan-rich variant can be compared with other tryptophan-containing antimicrobial peptides such as tachyplesin W4, tritrpticin, indolicidin and lactoferricin, in which tryptophan has been reported to be an essential constituent. The aromatic indolyl side chain of tryptophan is capable of $\pi$-$\pi$ stacking interactions and can participate in hydrogen bonding, particularly in an interfacial environment. For tyrosine- and phenylalanine-rich variants Y6 and F6 may also be capable of $\pi$-$\pi$ stacking interactions and/or can participate in hydrogen bonding, just as the tachyplesin derivatives, Y4 and F4 were found.

The antimicrobial activity of hBD3 derivatives depends on their ability to contact the pathogen cell membrane by electrostatic interactions between cationic hBD3 analogs and negative membrane of the pathogen, and for the anti-microbial molecule to insert into the membrane by hydrophobic interactions. The major determining structural factors are the net positive charge and the overall hydrophobicity. The overall hydrophobicity of peptides was calculated and measured by HPLC. Among the linear analogs and wild type hBD3, the most hydrophobic W6 and most hydrophilic S6 are potent antimicrobials, it shows that the third key structural determinant, the balance between hydrophilic surface area and hydrophobic surface area, thus maintaining an amphiphilic conformation, is of importance to maintaining high antibacterial activity.

In medium of low ionic strength, three linear 45-reside hBD3 derivatives were of similar potency compared to their disulfide bridged counterparts. No dependence on substitution of the cysteine residues was found, that is the replacement of cysteine by alanine (A), tryptophan (W) or carboxamidomethylated cysteine [C(Cam)] did not significantly change antibacterial activity compared to that of fully disulfide-bridged hBD3 peptides.

Cytotoxicity to Mammalian Cells and Hemolytic Activity

The potent anti-microbial linear analogs and wild-type hBD3 were tested regarding their cytotoxicity to human cells. Cytotoxicity of these analogs was analyzed on primary cultured human normal conjunctiva epithelial cells by measuring cell viability using CellTiter-blue. See FIG. 5. Wild type hBD3 was used as a control in all analyses. It is well established that cationic peptides not only interact with pathogen cells, but can also display toxic potential to mammal cells and eukaryotic cells. Microbial cell membranes consist of anionic phosphatidylcholine glycerol as a major component, however, eukaryotic cell membranes contain mainly zwitterionic, phosphatidylcholine and phosphatidylethanolamine susceptible to hydrophobic interactions [Yeaman and Yount, Biochemistry, 2005]. Therefore, it has been proposed that hemolytic activity of cationic antimicrobial peptides are directly connected with the hydrophobicity of peptides. [Hwang and Vogel, Biochemistry, 2005]. The cytotoxicity of each of the six linear peptides was much lower than that of wild-type hBD3 in the concentration of 6-100 ug/ml. The result clearly shows that it does not matter too much if the hydrophobicity of linear hBD3 analogs is high or low, they have decreased cytotoxicity in comparison with wild type hBD3. As the main 1-dimensional structural difference between linear analogs and the wild type hBD3 lies in the cyclic structure formed by disulfide bonds or its linearity due to the replacement of six cysteine residues by other residues, thus, it means the natural three disulfide-bond pattern in wild type hBD3 should be the main structural determinant for its high cytotoxicity. In other words, the linear polypeptide backbone is a key structural factor to the reduced cytotoxicity of the analogs. The difference in cytotoxicity and hemolytic activity of linear analogs are due to the sequence, which led different hydrophobicity. A6 S6 and C(Acm)6 with low hydrophobicity had the lowest cytotoxicity at a high concentration of 25-100 ug/ml, Y6 with medium hydrophobicity had mid-level cytotoxicity while F6 and W6 with high hydrophobicity had relatively the highest cytotoxicity. As there is no obvious difference in second structural conformation in pure water, the effect of second structural parameters of hBD3 and its derivatives on cytotoxicity and hemolytic activity is minor.

As human $\beta$ defensin 3 (hBD3) are structurally characteristic of being cationic amphiphilic with three dimensional folding and even quaternary structures, many structural determinants (1D, 2D, 3D and quaternary structural factors, e.g., highly net positive charge, sequence and residue distribution, amphiphilic conformation, hydrophobicity, 3D folding and dimmers formation) on antimicrobial activity, cytotoxicity and hemolytic activity. We have designed and synthesized a series of structurally homogenous full-length linear analogs of hBD3, providing a good model to further investigate effect of native three disulfide bonds pattern, amino acid residue with different hydrophobicity and molecular hydrophobicity of peptide on antimicrobial activity, cytotoxicity and hemolytic activity of peptides. Our results of hBD3 derivatives show that high antimicrobial activity, especially for W6 and S6 and F6, have been achieved and the decreased cytotoxicity to human cells was found for the six linear analogs and it can be controlled by the design of peptides in term of hydrophobicity, it shows that the native three disulfide bonds pattern in human $\beta$ defensins is a key structural determinant to it high cytotoxicity. This finding provides an alternative and new design concept of antimicrobial peptide, and have implication for academic and even commercial research and development of defensins peptides antibiotics, which can be produced at relatively low cost on large scale as the selective formation of disulfide bonds and complicated separation of defensins analogs with three disulfide bonds can be avoided or unnecessary. Correspondingly, potent antimicrobial defensins derivatives with little or no toxic effects on host cells might be designed and developed. As these analogs are potent anti-microbials but have low mammalian cell cytotoxicity they have diverse applications, for example, they may be added to contact lens solutions to prevent infections or added to OTC eye care solutions to give them more potency in warding off infections.

Example 2

C Terminal Fragment Analogs (10 Residues) of hBD3

The two cysteine residues at the C-terminus of the 10-residue fragment of native hBD3 were uniformly replaced by residues of differing hydrophobicity, viz., phenylalanine, tryptophan, tyrosine, leucine, isoleucine, valine, cysteine and histidine, to form the corresponding short peptides, the second series of hBD3 analogs, [coded as W2, F2, Y2, L2, I2, C2 (or C(Acm)2)] with varying overall hydrophobicities.

| | | |
|---|---|---|
| RGRKCCRRKK | 10-residue C-terminus fragment of hBD3 | SEQ ID NO: 37 |
| RGRKWWRRKK | W2 | SEQ ID NO: 38 |
| RGRKFFRRKK | F2 | SEQ ID NO: 39 |

-continued

| | | |
|---|---|---|
| RGRKYYRRKK | Y2 | SEQ ID NO: 40 |
| RGRKLLRRKK | L2 | SEQ ID NO: 41 |
| RGRKIIRRKK | I2 | SEQ ID NO: 42 |
| RGRKVVRRKK | V2 | SEQ ID NO: 43 |
| RGRKHHRRKK | H2 | SEQ ID NO: 44 |
| RGRKC(Acm)C(Acm)RRKK | C2 [or C(Acm)2] | SEQ ID NO: 45 |

This series of engineered short peptides are designed, synthesized and structurally characterized by mass spectra and molecular hydrophobicity analysis using experimental and theoretical methods as described above.

Molecular Hydrophobicity

The overall molecular hydrophobicity of the C-terminus hBD3 analogs were measured by RP-HPLC-MS in terms of retention time at 1 mg/ml (Table 4 and FIG. 14). RP-HPLC is an approach that is commonly employed for such comparisons of peptides or amino acid side chains among antibacterial peptides. Since the stationary phase of C18-modified silica is hydrophobic and the mobile phase (water-acetonitrile) is hydrophilic, longer retention times should be correlated with higher hydrophobicity. The measured order for the molecular hydrophobicity of the peptides is as follows: W2>F2>L2>I2>Y2>V2>C2>H2.

TABLE 4

The overall hydrophobicity of peptides in terms of retention time (Rt) in HPLC-MS and ACN % of peak (gradient 2-15.5% in 30 mins and then 15.5-31% in 3 mins of eluent B (ACN)

| Variant | Retention time (min) (UV peak)[a] | ACN %[a] |
|---|---|---|
| W2 | 31.92 | 25.42 |
| F2 | 28.41 | 14.78 |
| L2 | 24.19 | 12.88 |
| I2 | 22.13 | 11.96 |
| Y2 | 21.75 | 11.79 |
| V2 | 17.46 | 9.86 |
| C2 | 17.05 | 9.67 |
| H2 | 11.45 | 7.15 |

[a]Order for The order for overall hydrophobicity of peptides: W2 > F2 > L2 > I2 > Y2 > V2 > C2 > H2

The relative hydrophobicities of the peptides were also calculated based on the Hopp-Woods hydrophilicity scale (Table 5). The order for overall hydrophobicity of this series of peptides: W2>F2>Y2>L2=I2>V2>H2. This scale is a hydrophilic index where apolar residues have been assigned negative values, and is typically used to identify antigenic regions based on hydrophilic patches. For each peptide, we summed the values corresponding to each residue separately in each peptide to gauge the peptide's relative hydrophobicity with respect to the remaining analogs. The trend in hydrophobicity of peptides computed using this scale generally matches that of the experimental HPLC retention time data, except for the order for Y2, L2 and I2. C2 [C(Acm)2], was excluded as Acm does not have a corresponding value in the Hopp-Woods scale. The eight peptides show relatively high hydrophilicity, however, the overall molecular hydrophobicity varies in a large range (Table 4 and FIG. 14).

TABLE 5

The basic physicochemical property of C-Terminus fragment peptides

| Variant | Number of residues | | Net positive charge | Relatively overall hydrophobicity[a] |
|---|---|---|---|---|
| | Total | Hydrophobic (aromatic) residue | | |
| W2 | 10 | 2 (2) | 7 | 14.2 |
| F2 | 10 | 2 (2) | 7 | 16 |
| Y2 | 10 | 2 (2) | 7 | 16.4 |
| L2 | 10 | 2 (0) | 7 | 17.4 |
| I2 | 10 | 2 (0) | 7 | 17.4 |
| V2 | 10 | 2 (0) | 7 | 18 |
| Wt-fragment | 10 | 0 (0) | 7 | 19 |
| H2 | 10 | 0 (2) | 9[b] | 20 |
| C2 | 10 | 0 (0) | 7 | n.c. |

[a]The overall hydrophobicity was calculated based on the hydrophobicity scale of Hopp-Woods hydrophilicity scale. Lower value corresponds to lower hydrophilicity or higher hydrophobicity;
n.c., not calculated.
The order for overall hydrophobicity of peptides: W2 > F2 > Y2 > L2 = I2 > V2 > H2
[b]Histidine: weakly basic Cytotoxicity The cytotoxicities of native hBD3 and four of the eight new peptides {W2, Y2, V2 and L2) to human conjunctival epitheliam cells were tested. The primary results of the cytotoxicity tests (FIG. 15) show that four peptides show decreased cytotoxicity in the concentration range of 6.25-200 μg/ml in comparison with native hBD3, as did the first series of six linear full-length analogs of hBD3 [F6, W6, Y6, A6, S6 and C(Acm) 6].

Thus, when comparing Table 4 and FIG. 15, this series of peptides corroborates our earlier conclusions that hydrophobicity correlate well with cytotoxicity. We have shown the new peptide designs reduces cytotoxicity and this is particularly important, considering that these peptides will be directed to mucosal surfaces which are covered by epithelial cells.

REFERENCES

1. Ganza, T. Defensins and host defense, *Science,* 1999, 286, 420-421
2. Raj, P. A. and A. R. Dentino. Current status of defensins and their role in innate immunity and adaptive immunity, *FEMS Microbio. Lett.* 2002, 206, 9-18
3. Yang, D., O. Chertov and J. J. Oppenheim. Participation of mammalian defensins and cathelicidins in anti-microbial immunity: receptors and activities of human defensins and cathelicidin (LL-37), *J. Leukoc. Biol.,* 2001, 69, 691-697
4. Kaiser, V., and Diamond, G., *J. Leukoc. Biol.,* 2000, 68, 779-784
5. Schroder, J. M., *Cell Mol. Life Sci.,* 1999, 56, 32-46
6. Garcia J. R., A. Krause, S. Schultz, J. Rodriguez-Jimenez, E. Kluver, K. Adermann, U. Forssmann, A. Frimpong-Boateng, R. Bals, W. G. Forssmann, Human β-defensin 4: a novel inducible peptide with a specific salt-sensitive spectrum of antimicrobial activity. *FASEB J.,* 2001, 15: 1819-1821
7. Harder J., J. Bartels, E. Christophers, and J. M. Schroder, A peptide antibiotic from human skin, *Nature,* 1997, 276: 5707-5713.
8. Schibli David J., Howard N. Hunter, Vladimir Aseyev, Timothy D. Starner, John M. Wiencek, Paul B. McCray, Jr., Brian F. Tack, and Hans J. Vogel, The solution structures of the human β-defensins lead to a better understanding of the potent bactericidal activity of HBD3 against *Staphylococcus aureus*, *J. Biol. Chem.*, 2002, 277 (10), 8279-8289
9. Harder J., Bartels J., Christophers, and Schroder, J. M., *J. Biol. Chem.*, 2001, 276, 5707-5713
10. Garcia J. R., Jaumann, F. Schultz, S. Krause, A. Rodriguez-Jimenez J., Forssmann U., Adermann, K., Kluver E., Vogelmeier, C., Becker D., Hedrich R., Forssmann W. G., and Bals R., *Cell Tissue Res.*, 2001, 306, 257-264
11. Yeaman, M. R. and Yount, N. Y., Mechanisms of antimicrobial peptide action and resistance, Pharmacol. Rev. 2003, 55, 27-55
12. Hwang, P. M. and Vogel, H. J., Structure-function relationships of antimicrobial peptides, Biochem. Cell Biol., 1998, 76, 235-246.
13. Zucht, H. D., Grabowsky, J., Schrader, M., Liepke, C., Jurgens M., Schulz-Knappe, P., and Forssmann, W. G., Human β-defensin-1: a urinary peptide present in variant molecular forms and its putative functional implication, Eur. J. Med. Res., 1998, 3, 315-323
14. Wu, Z., Hoover, D. M., De Yang, Cyril Boulegue, Fanny Santamaria, Joost J. Oppenheim, jacek Lubkowski, Engineering disulfide bridges to dissect antimicrobial and chemotactic activities of human β-defensin 3, PNAS, 2003, Vol. 100, no. 15, 8880-8885.
15. Hoover D. M., Wu Z., Tucker K., Lu W., Lubkowsli J., Antimicrobial characterisation of human β-defensin 3 derivatives, 2003, Antimicrobial Agent and Chemotherapy, Vol. 47, No. 9, p. 2804-2809.
16. Gordon, Y.; G., Eric; McDermott, Alison, A Review of Antimicrobial Peptides and Their Therapeutic Potential as Anti-Infective Drugs, Current Eye Research, 2005, Vol. 30, N. 7, p. 505-15.
17. Wimley William C. and White Stephen H., Experimentally determined hydrophobicity scale for proteins at membrane interfaces, Nature Structural Biology 3, 842-848 (1996).
18. Hopp, T. P. and Woods, K. R. (1983). A computer program for predicting protein antigenic determinants. *Mol Immunol*, 20(4):483-489.
19. Black, S. D. and Mould, D. R. (1991) *Anal. Biochem.* 193, 72-82.
20. Ilker, M. F.; Nusslein, K.; Tew, G. N.; Coughlin, E. B. Tuning the Hemolytic and Antibacterial Activities of Amphiphilic Polynorbornene Derivatives, *J. Am. Chem. Soc.*; 2004; 126(48); 15870-15875.
21. Sawai, M. V.; Jia, H. P.; Liu, L.; Aseyev, V.; Wiencek, J. M.; McCray, P. B., Jr.; Ganz, T.; Kearney, W. R.; Tack, B. F., The NMR Structure of Human β-Defensin-2 Reveals a Novel-Helical Segment, *Biochemistry*; 2001; 40(13); 3810-3816.
22. Oren, Z.; Shai, Y., Selective Lysis of Bacteria but Not Mammalian Cells by Diastereomers of Melittin: Structure-Function Study, *Biochemistry*; 1997; 36(7); 1826-1835.
23. Enno Kluver, Sandra Schulz-Maronde, Svenja Scheid, Bernd Meyer, Wolf-Georg Forssmann, and Knut Adermann, Structure-activity relationship of human β-defensin 3: Influence of disulfide bonds and cysteine substitution on antimicrobial activity and cytotoxicity, Biochemistry, 2005, 44, 9804-9816.

---

The invention claimed is:

1. An isolated antimicrobial peptide, wherein the peptide is a linear analog of human β-defensin 3 of length 10 amino acid (aa) residues consisting of SEQ ID NO:37, SEQ ID NO:38, SEQ ID NO:39, SEQ ID NO:40, SEQ ID NO:41, SEQ ID NO:42, SEQ ID NO:43, SEQ ID NO:44, or SEQ ID NO:45.

2. The isolated peptide according to claim 1, wherein the peptide has a reduced cytotoxicity to at least one epithelial cell compared to the wild type human β-defensin 3.

3. A pharmaceutical or antimicrobial composition comprising at least one antimicrobial peptide, wherein the peptide is a linear analog of human β-defensin 3 of length 10 amino acid (aa) residues consisting of SEQ ID NO:37, SEQ ID NO:38, SEQ ID NO:39, SEQ ID NO:40, SEQ ID NO:41, SEQ ID NO:42, SEQ ID NO:43, SEQ ID NO:44, or SEQ ID NO:45, optionally in combination with at least one non-peptide antimicrobial agent.

4. The pharmaceutical composition according to claim 3, wherein the composition is for topical administration and is suitable for treatment of skin and/or mucous membrane(s).

5. The pharmaceutical or antimicrobial composition according to claim 3, wherein the composition is in the form of an eye drop(s) composition and/or solution.

6. A contact lens solution and/or an eye drop composition and/or solution comprising at least one peptide, wherein the peptide is a linear analog of human β-defensin 3 of length 10 amino acid (aa) residues consisting of SEQ ID NO:37, SEQ ID NO:38, SEQ ID NO:39, SEQ ID NO:40, SEQ ID NO:41, SEQ ID NO:42, SEQ ID NO:43, SEQ ID NO:44, or SEQ ID NO:45.

7. A device coating, wherein the coating comprises at least one peptide, wherein the peptide is a linear analog of human β-defensin 3 of length 10 amino acid (aa) residues consisting of SEQ ID NO:37, SEQ ID NO:38, SEQ ID NO:39, SEQ ID NO:40, SEQ ID NO:41, SEQ ID NO:42, SEQ ID NO:43, SEQ ID NO:44, or SEQ ID NO:45.

8. The device coating according to claim 7, wherein the device coating is a medical device coating.

9. A kit comprising at least one antimicrobial peptide according to claim 1, disposed in at least one suitable container.

10. A method of inhibiting and/or reducing the growth, optionally in a host, of at least one microorganism comprising contacting the microorganism with or administering to or applying onto the host at least one antimicrobial peptide, wherein the peptide is a linear analog of human β-defensin 3 of length 10 amino acid (aa) residues consisting of SEQ ID NO:37, SEQ ID NO:38, SEQ ID NO:39, SEQ ID NO:40, SEQ ID NO:41, SEQ ID NO:42, SEQ ID NO:43, SEQ ID NO:44, or SEQ ID NO:45, and/or at least one antimicrobial composition according to claim 4, alone, or in combination with another antimicrobial agent and/or antibiotic.

11. A method of treating at least one microbial infection in a subject, said method comprising administering to a subject at least one isolated antimicrobial peptide according to claim 1, alone, or in combination with another antimicrobial agent and/or antibiotic.

12. A drug screening method comprising administering at least one isolated antimicrobial peptide according to claim 1 to at least one epithelial cell, and determining whether the antimicrobial peptide has reduced cytotoxicity to the cell compared to the wild type hBD3.

13. An isolated peptide according to claim 1, wherein the peptide is either SEQ ID NO:38, SEQ ID NO:39, SEQ ID NO:40, SEQ ID NO:41, SEQ ID NO:42, SEQ ID NO:43, SEQ ID NO:44, or SEQ ID NO:45.

14. A pharmaceutical or antimicrobial composition according to claim 3, wherein the peptide is either SEQ ID NO:38, SEQ ID NO:39, SEQ ID NO:40, SEQ ID NO:41, SEQ ID NO:42, SEQ ID NO:43, SEQ ID NO:44, or SEQ ID NO:45.

15. A coated lens solution and/or an eye drop composition and/or solution according to claim 6, wherein the peptide is either SEQ ID NO:38, SEQ ID NO:39, SEQ ID NO:40, SEQ ID NO:41, SEQ ID NO:42, SEQ ID NO:43, SEQ ID NO:44, or SEQ ID NO:45.

16. A device coating according to claim 7, wherein the peptide is either SEQ ID NO:38, SEQ ID NO:39, SEQ ID NO:40, SEQ ID NO:41, SEQ ID NO:42, SEQ ID NO:43, SEQ ID NO:44, or SEQ ID NO:45.

* * * * *